United States Patent
Asano et al.

(10) Patent No.: US 6,841,549 B1
(45) Date of Patent: Jan. 11, 2005

(54) CONDENSED IMIDAZOLE COMPOUNDS AND A THERAPEUTIC AGENT FOR DIABETES MELLITUS

(75) Inventors: Osamu Asano, Ibaraki (JP); Hitoshi Harada, Ibaraki (JP); Seiji Yoshikawa, Ibaraki (JP); Nobuhisa Watanabe, Ibaraki (JP); Takashi Inoue, Ibaraki (JP); Tatsuo Horizoe, Ibaraki (JP); Nobuyuki Yasuda, Ibaraki (JP); Kaya Ohashi, Ibaraki (JP); Hiroe Minami, Ibaraki (JP); Junsaku Nagaoka, Ibaraki (JP); Manabu Murakami, Ibaraki (JP); Seiichi Kobayashi, Belmont, MA (US); Isao Tanaka, Ibaraki (JP); Tsutomu Kawata, Ibaraki (JP); Naoyuki Shimomura, Ibaraki (JP); Hiroshi Akamatsu, Ibaraki (JP); Naoki Ozeki, Ibaraki (JP); Toshikazu Shimizu, Ibaraki (JP); Kenji Hayashi, Ibaraki (JP); Toyokazu Haga, Ibaraki (JP); Shigeto Negi, Ibaraki (JP); Toshihiko Naito, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 19 days.

(21) Appl. No.: 10/018,688

(22) PCT Filed: Jun. 30, 2000

(86) PCT No.: PCT/JP00/04358

§ 371 (c)(1),
(2), (4) Date: Dec. 20, 2001

(87) PCT Pub. No.: WO01/02400

PCT Pub. Date: Jan. 11, 2001

(30) Foreign Application Priority Data

Jul. 2, 1999 (JP) .......................................... 11-188484
May 16, 2000 (JP) ....................................... 2000-143495
Jun. 19, 2000 (JP) ....................................... 2000-182786

(51) Int. Cl.[7] .................. A16K 31/33; A16K 31/52; C07D 239/70; C07D 487/00; C07D 471/00
(52) U.S. Cl. ................. 514/183; 514/263.4; 514/263.1; 514/263.22; 544/253; 544/264; 544/256; 544/277; 544/255
(58) Field of Search ............................. 514/183, 263.4, 514/263.1, 263, 263.22; 544/253, 264, 256, 277, 26.4, 255

(56) References Cited

U.S. PATENT DOCUMENTS

| 4,212,876 A | 7/1980 | Houlihan |
| 4,714,762 A | 12/1987 | Hoefle et al. |
| 4,728,644 A | 3/1988 | Yuki et al. |
| 4,772,600 A | 9/1988 | Tomczuk et al. |
| 5,117,830 A * | 6/1992 | McAfee et al. ............. 600/431 |
| 5,552,426 A | 9/1996 | Lunn et al. |

FOREIGN PATENT DOCUMENTS

| EP | 0 544 445 A2 | 6/1993 |
| EP | 1 054 012 A1 | 11/2000 |
| JP | 2-306916 | 12/1990 |
| JP | 10-182636 | 7/1998 |
| JP | 11-263789 | 9/1999 |
| SU | 1 282 506 A | 12/1997 |
| WO | WO 95/18128 | 7/1995 |
| WO | WO 97/01551 | 1/1997 |
| WO | 97-33873 | 9/1997 |
| WO | WO 98/01459 | 1/1998 |
| WO | WO 98/03507 | 1/1998 |
| WO | 98-39344 | 9/1998 |
| WO | 99-57103 | 11/1999 |

OTHER PUBLICATIONS

Barlin G.B. et al,J. of Chemical Society, Section B, Physical Organic, 7, 1425–32(1971), also cited as Chemical Abstract DN 75:62924.*
Chin et al, Chemical Abstract DN 95:6196.*
Verlinde et al, J. Medicinal Chemistry, 37/21, 3605–13(1994), also cited as Chemical Abstract Dn 121:245130.*
MCafee et al, Chemical Abstract DN 120:95745.*
Verlinde et al,J.Med. Chem. 37/21,3605–13(1994), See compound with CAS RN# 158555–06–7.*

(List continued on next page.)

Primary Examiner—Richard L. Raymond
Assistant Examiner—Sudhaker B. Patel
(74) Attorney, Agent, or Firm—Birch, Stewart, Kolasch & Birch, LLP

(57) ABSTRACT

The present invention provides a preventive or therapeutic agent for diabetes mellitus and diabetic complications, which is a new type based on an adenosine A2 receptor antagonist action.

That is, it provides a novel condensed imidazole compound which has an adenosine A2 receptor antagonist action, is effective for preventing or treating diabetes mellitus and diabetic complications, and is represented by the formula (I);

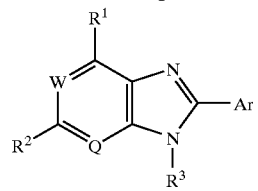

(wherein $R^1$ represents e.g. an amino group which may be substituted with an alkyl group; $R^2$ represents e.g. hydrogen atom, an alkyl group, a cycloalkyl group or an alkyl group, alkenyl group or alkynyl group which may be substituted with hydrox etc.; $R^3$ represents e.g. an optionally substituted alkyl group, alkenyl group, alkynyl group, aryl group, heteroaryl group, pyridinone group, pyrimidinone group or piperadinone group; Ar represents e.g. an optionally substituted aryl or heteroaryl group; and Q and W are the same as or different from each other and each represents N or CH), a pharmacologically acceptable salt or hydrates thereof.

34 Claims, No Drawings

OTHER PUBLICATIONS

Chorvat et al,J.Med.Chem. 42/5,833–848(1999), also cited as Chemical Abstract DN 130:209672.*

Tangi et al, Heterocycles,30/1,435–40(1990), also cioted as Chemical Abstract DN 113:114920.*

Young et al, J. Med. Chemistry, 33/8,2073–80(1990), also cited as Chemical Abstract DN 113:58784.*

Th. McKenzie et al, J. Heterocyclic Chem. 24,1551–53(1987).*

Nico et al,J. Org.Chem. 48/6,850–855(1983).*

Bergmann et al, Tetrahedron, 30, 3045–51(1974).*

R. J. Chorvat et al., (Mar. 1999) vol. 42, Nol 5, pp. 833–848.

R.C. Young et al., J. Med. Chem. (1990), vol. 33, No. 8, pp. 2073–2080.

A. Matsuda et al., (1991), vol. 263, No. 2, pp. 93–100.

G.B. Barlin et al., J. Chem. Soc. B., (1971), No. 7, pp. 1425–1432.

B.E. Tomczuk et al., J. Med. Chem. (1991), vol. 34, No. 10, pp. 2993–3006.

Hitoshi Takagi et al.; Investigative Ophthalmology & Visual Science, Jun. 1996, vol. 37, No. 7, pp. 1311–1321.

Hitoshi Takagi et al.; Investigative Ophthalmology & Visual Science, Oct. 1996, vol. 37, No. 11, pp. 2165–2176.

Bertil B. Fredholm et al.; Pharmacological Reviews; vol. 46, No. 2, pp. 143–156.

Dietrich Van Calker et al.; Journal of Neurochemistry, vol. 33, pp. 999–1005.

Robert F. Bruns et al.; Molecular Pharmacology, vol. 29, pp. 331–246.

W. Wan et al,; Journal of Neurochemistry; vol. 55, No. 5, 1990, pp. 1763–1771.

R.A. John Challis et al.; Biochem. J.; 1984; vol. 221, pp. 915–917.

R.A. John Challis et al.; European Journal of Pharmacology—Molecular Pharmacology Section; vol. 226; 1992; pp. 121–128.

Susan J. Vannucci et al.; Biochem. J.; 1992, vol. 288; pp. 325–330.

Michael G. Collis et al.; TiPS; Oct. 1993, vol. 14, pp. 360–366.

Yu. M. Yutilov et al.; English translation of Khimiya Geterotsiklicheskikh Soedinenii, No. 5, pp. 639–649, May 1987.

Yu. M. Yutilov et al., Chemical Abstracts, vol. 87, No. 9, Aug. 29, 1977, Abstract No. 68239.

Yu M. Yutilov et al.; Chemical Abstracts, vol. 98, No. 7, Feb. 14, 1983, Abstract No. 53774.

Yu M. Yutilov et al.; Chemical Abstracts, vol. 113, No. 21, Nov. 19, 1990, Abstract No. 186495.

Guido Viscardi et al.; Journal of Heterocyclic Chemistry, vol. 29, No. 4, Jul. 1992, pp. 835–839.

Spiros Grivas et al.; Journal of Heterocyclic Chemistry, vol. 32, No. 2, 1995, pp. 467–471.

Ludwik Bukowski et al.; Arch. Pharm. (Weinheim), vol. 324, No. 2, 1991, pp. 121–127.

P. Barraclough et al.; Eur. J. Med. Chem., vol. 25, No. 6, 1990, pp. 467–477.

Yu M. Yutilov et al.; vol. 25, No. 7, Jul. 1989, pp. 940–947; English translation of Khimiya Geterotsiklicheskikh Soedinenii.

Francisco Perandones et al.; Journal of Hetercyclic Chemistry, vol. 34, Sep. 1997, pp. 1459–1461.

Francisco Perandones et al.; Journal of Heterocyclic Chemistry; vol. 34, Jan. 1997, pp. 107–112.

Thomas C. McKenzie et al.; Journal of Heterocyclic Chemistry, vol. 24, Nov. 1987, pp. 1551–1553.

Nico Kos et al.; Journal of Organic Chemistry Society; vol. 48, No. 6, 1983, pp. 850–855.

F. Bergmann et al.; Tetrahedron, vol. 30, No. 17, Sep. 1974, pp. 3045–3051.

Yu M. Yutilov et al.; Russian Journal of Organic Chemistry; vol. 30, No. 3, 1994, pp. 461–463.

Ken–ichi Tanji et al.; Heterocycles, vol. 30, No. 1, 1990, pp. 435–440.

R.A. Abramovitch et al.; Journal Organic Chemistry, vol. 39, No. 13, 1974, pp. 1802–1807.

Mitsuhiro Takeshita et al.; Heterocycles, vol. 31, No. 12, 1990, pp. 2201–2204.

Imayoshi Tomonori; Patent Abstracts of Japan, vol. 010, No. 362, Dec. 4, 1986.

* cited by examiner

CONDENSED IMIDAZOLE COMPOUNDS AND A THERAPEUTIC AGENT FOR DIABETES MELLITUS

This application is the national phase under 35 U.S.C. § 371 of PCT International Application No. PCT/JP00/04358 which has an International filing date of Jun. 30, 2000, which designated the United States of America and was published in English.

FIELD OF THE INVENTION

The present invention relates to a novel purine compound having a hypoglycemic action and a glucose tolerance improving action on the basis of an inhibitory action on glucose production and a promoting action on glucose utilization at the periphery and to a preventive or therapeutic agent for diabetes mellitus and diabetic complications comprising the purine compound. More specifically, it relates to a novel purine compound which is an adenosine A2 receptor antagonist and to a preventive or therapeutic agent for diabetes mellitus and diabetic complications on the basis of an adenosine A2 receptor antagonist action.

PRIOR ART

With regard to therapeutic agents for diabetes mellitus, various biguanide compounds and suflonylurea compounds have been used. However, the biguanide compounds induce lactic acidosis and, therefore, their use is limited while the sulfonylurea compounds often result in severe hypoglycemia due to their strong hypoglycemic action and, therefore, their use is to be careful.

Diabetic complications are recognized in the eyes, kidney, nervous system, cardiovascular system, skin etc., and frequently occurring complications specific to diabetes mellitus include retinopathy, nephrosis and neuropathy. It is considered that these complications are reduced generally by achieving blood sugar controlled at the normal level or thereabout ("Saishin Igaku Daijiten" (Newest Medical Large Dictionary) published in 1988 by Ishiyaku Shuppan). A major factor for diabetic retinopathy (particularly proliferating retinopathy) is angiogenesis, and activation of an adenosine A2 receptor promotes angiogenesis in the retina due to low oxygen (Takagi, H. et al., Invest. Ophthalmol. Vis. Sci., 37, 1311-1321 and 2165-2176 (1996)).

Adenosine is a nucleoside widely existing in living body and has a physiological action on the cardiovascular system, central nervous system, respiratory system, kidney, immune system, etc. The action of adenosine is achieved via at least four receptors —A1, A2a, A2b and A3— in which G protein participates (Fredholm, B. B. et al., Pharmacol. Rev., 46, 143–156, 1994). In 1979, adenosine receptor was at first classified into A1 and A2 on the basis of their pharmacological action and participation in adenylate cyclase (Van Calker, D. et al., J. Neurochem., 33, 999–1003, 1979). Then A2 receptor has classified into the subtypes of A2a and A2b on the basis of high and low affinity for adenosine and for adenosine A2 agonists, i.e. NECA and CGS-21680 (Burns, R. F. et al., Mol. Pharmacol., 29, 331–346, 1986; Wan, W. et al., J. Neurochem., 55, 1763–1771, 1990). Although gradually, physiological and pathological significance of those receptors has been clarified in the central nervous system, circulatory system, etc.

With regard to glucose metabolism, the following reports have been available. In an experiment using skeletal muscles, adenosine lowers the insulin sensitivity due to an agonistic action on the A1 receptor suppressing the glucose uptake while an A1 receptor antagonist increases the insulin sensitivity (Challis, R. A., Biochem., J., 221, 915–917, 1984; Challis, R. A., Eur. J. Pharmacol., 226, 121–128, 1992). In adipocytes, adenosine enhances the sensitivity of insulin via an A1 receptor, whereby glucose uptake is promoted (Vannucci, S. J., Biochem. J., 288, 325–330, 1992). Further, WO 95/18128 and WO 98/03507 disclose a therapeutic agent for diabetes mellitus comprising an A1 receptor antagonist. Thus, there have been many reports on an A1 receptor. With regard to an adenosine A2 receptor, there is a simple description in WO 97/01551 suggesting a therapeutic agent for diabetes mellitus comprising the A2a receptor antagonist although any ground is not mentioned at all. In TIPS., 14, 360–366, 1993, participation of the adenosine A2 receptor in the promotion of gluconeogenesis in hepatic cells is suggested but there is no specific description at all. On the contrary, WO 98/01459 describes a therapeutic agent for diabetes mellitus comprising the A2 receptor agonist but there is no description of the adenosine A2 receptor antagonist at all. As such, the positioning of the adenosine A2 receptor antagonist as a therapeutic agent for diabetes mellitus has been in a chaotic state.

The object of the present invention is to provide a preventive or therapeutic agent for diabetes mellitus and diabetic complications on the basis of a new action mechanism which is different from that of conventional biguanide compounds and sulfonylurea compounds having several limitations in actual use.

DISCLOSURE OF INVENTION

As a result of extensive study, the present inventors found that an adenosine receptor antagonist serves as a new type of a preventive or therapeutic agent for diabetes mellitus. That is, hyperglycemia in spontaneous diabetic mice was improved by the adenosine receptor antagonist. This action was estimated to attributable to the inhibitory action of the antagonist on both glycogenolysis reaction and gluconeogenesis in the liver promoted by endogenous adenosine. On the basis of this finding, they searched for compounds having an excellent hypoglycemic action and glucose tolerance improving action as a preventive or therapeutic agent for diabetes mellitus, and as a result, they found novel condensed imidazole compounds represented by the following formula (I). As a result of further extensive study for their action mechanism, they found that among adenosine receptor antagonism, an adenosine A2 receptor antagonism is an essential factor for the hypoglycemic action and glucose tolerance improving action, and they arrived at use of the adenosine A2 receptor antagonist as a new type of a preventive or therapeutic agent for diabetes mellitus and diabetic complications, and the present invention was thereby completed.

The novel condensed imidazole compound of the present invention is a condensed imidazole compound represented by the following formula (I):

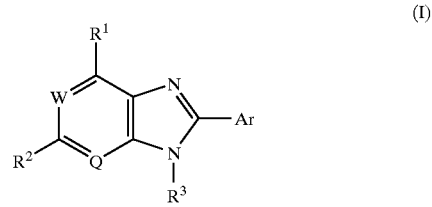

(wherein $R^1$ represents 1) hydrogen, 2) hydroxyl, 3) a halogen atom, 4) an optionally substituted C1–C8 alkyl group or 5) formula —NR⁴R⁵ (wherein R⁴ and R⁵ are the same as or different from each other and each represents hydrogen, a C1–C8 alkyl group, a C3–C8 cycloalkyl group, or a C2–C5 saturated cyclic amino group which is formed with the nitrogen to which they bind, whereupon this ring may contain oxygen, sulfur or nitrogen other than the nitrogen and may be substituted with a C1–C4 alkyl group which may be substituted with a halogen atom; $R^2$ represents 1) hydrogen, 2) a halogen atom, 3) formula —NR⁶R⁷ (wherein R⁶ and R⁷ are the same as or different from each other and each represents hydrogen, a C2–C5 acyl group, a C1–C8 alkyl group or a C3–C8 cycloalkyl group, or R⁶ and R⁷ represent a C2–C5 saturated cyclic amino group which is formed with the nitrogen to which they bind, whereupon this ring may contain oxygen, sulfur or nitrogen other than the said nitrogen and may be substituted with a C1–C4 alkyl group which may be substituted with a halogen atom), 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group, 6) a C1–C8 alkyl group which may be substituted with a halogen atom, hydroxyl ora C1–C4 alkyl group or7) a C1–C8 alkoxy group which may be substituted with a halogen atom, hydroxyl or a C1–C4 alkyl group $R^3$ resents 1) a C3–C8 alkynyl group which may be substituted with a halogen atom, hydroxyl ora C1–C4 alkyl group, 2) a C3–C8 alkenyl group which may be substituted with a halogen atom, hydroxyl or a C1–C4 alkyl group, 3) a C1–C8 alkyl group which may be substituted with a halogen atom, hydroxy or a C1–C4 alkyl group, 4) an optionally substituted aryl group, 5) an optionally substituted heteroaryl group, 6) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group or 8) a dihydroxo- or tetrahydrodioxopyrazinyl group which may be substituted with a) a halogen atom or a C1–C6 alkyl group, and whose nitrogen atom is further substituted with b-i) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group; Ar represents 1) an optionally substituted aryl group, 2) an optionally substitutedheteroaryl group, 3) an oxopyridyl group which may be substituted with a halogen atom or a C1–C6 alkyl group, and whose nitrogen atom is further substituted with a C1–C6 alkyl group or a C3–C6 cycloalkyl group or 4) an oxopyrimidyl group which may be substituted with ahalogen atomora C1–C6 alkyl group, and whose nitrogen atom is further substituted with a C1–C6 alkyl group or a C3–C6 cycloalkyl group; and Q and W are the same as or different from each other and each represents N or CH, provided that when $R^2$ is 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group or 6) a C1–C8 alkyl group which may be substituted with a halogen atom, hydroxyl or a C1–C4 alkyl group, $R^3$is not 3) a C1–C8 alkyl group which may be substituted with a halogen atom, hydroxyl or a C1–C4 alkyl group or 4) an optionally substituted aryl group), apharmacologically acceptable salt thereof or hydrates thereof;

the above-mentioned condensed imidazole compound, a pharmacologically acceptable salt thereof or hydrates thereof, wherein $R^2$ is hydrogen atom;

the above-mentioned condensed imidazole compound, a pharmacologically acceptable salt thereof or hydrates thereof, wherein $R^3$ represents 1) an optionally substituted heteroaryl group, 2) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 3) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl, or an optionally protected carboxyl group, b-2) an optionally substituted C3–C6 cycloalkyl-C1–C4 alkyl group or b-3) a C3–C6 cycloalkyl group, or 4) a dihydroxo or tetrahydrodioxopyrazinyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group, or b-3) a C3–C6 cycloalkyl group;

the above-mentioned condensed imidazole compound, a pharmacologically acceptable salt thereof or hydrates thereof, wherein $R^3$ represents 1) an optionally substituted pyridyl group, 2) an optionally substituted pyrimidyl group, 3) a 1,2-dihydro-2-oxopyridyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group; b-2) an optionally substituted C3–C6 cycloalkyl-C1–C4 alkyl group; or b-3) an optionally substituted C3–C6 cycloalkyl group, or 4) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group; b-2) an optionally substituted C3–C6 cycloalkyl-C1–C4 alkyl group; or b-3) a C3–C6 cycloalkyl group;

the above-mentioned condensed imidazole compound, a pharmacologically acceptable salt thereof or hydrates thereof, wherein Ar is an optionally substituted aryl;

the above-mentioned condensed imidazole compound, a pharmacologically acceptable salt thereof or hydrates thereof, wherein Ar is a phenyl substituted with a halogen atom;

the above-mentioned condensed imidazole compound, a pharmacologically acceptable salt thereof or hydrates thereof, wherein $R^1$ is represented by the formula —NR⁴R⁵ (wherein R⁴ and R⁵ are the same as or different from each other and each represents hydrogen, a C1–C8 alkyl group or a C3–C8 cycloalkyl group, or a C2–C5 saturated cyclic amino group which is formed with a nitrogen atom to which they bind, whereupon this ring may contain oxygen, sulfur or nitrogen other than the nitrogen and may be substituted with a C1–C4 alkyl group which may be substituted with a halogen atom;

the above-mentioned condensed imidazole compound, a pharmacologically acceptable salt thereof or hydrates thereof, wherein $R^1$ is amino;

the above-mentioned condensed imidazole compound, a pharmacologically acceptable salt thereof or hydrates thereof, wherein $R^1$ is amino; $R^2$ is hydrogen; and $R^3$ is 1) a pyridyl group which may be substituted with hydroxyl or a C1–C6 alkyl group or 2) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group; b-2) an optionally substituted C3–C6 cycloalkyl-C1–C4 alkyl group; or b-3) an optionally substituted C3–C6 cycloalkyl group;

the above-mentioned condensed imidazole compound, a pharmacologically acceptable salt or hydrates thereof, wherein Q or W is N;

the above-mentioned condensed imidazole compound, a pharmacologically acceptable salt thereof or hydrates thereof, wherein $R^1$ is amino, $R^2$ is hydrogen, and $R^3$ is a 1,2-dihydro-2-oxopyridyl group whose nitrogen may be substituted with a C1 to C6 alkyl group which may be substituted with a halogen atom;

the above-mentioned condensed imidazole compound, a pharmacologically acceptable salt thereof or hydrates thereof, wherein $R^1$ is amino, $R^2$ is a C2 alkynyl group which is substituted with a hydroxy-C4–C6 cycloalkyl group, $R^3$ is a C3 alkenyl group, and Ar is a phenyl substituted with a halogen atom; and the above-mentioned condensed imidazole compound, which is selected from the following group:
1) 5-[6-amino-8-(3-fluorophenyl)-9H-9-purinyl)-1-methyl-1, 2-dihydro-2-pyridinone; and
2) 1-{2-[6-amino-8-(3-fluorophenyl)-9-(2-propenyl)-9H-2-purinyl]-1-ethynyl}-1-cyclobutanol,
a pharmacologically acceptable salt thereof or hydrates thereof.

The present invention provides the condensed imidazole compound of the above formula (I), a pharmacologically acceptable salt thereof or hydrates thereof, which is a purine compound wherein each of Q and W is a nitrogen atom. Further, the present invention provides the condensed imidazole compound of the above formula (I), a pharmacologically acceptable salt thereof or hydrates thereof, which is a benzoimidazol compound wherein each of Q and W is —CH. Further, the present invention provides the condensed imidazole compound of the above formula (I), a pharmacologically acceptable salt thereof or hydrates thereof, which is an imidazopyridine compound wherein one of Q and W is N, and the other is —CH.

The present invention provides an agent for preventing or treating diabetes mellitus, which comprises the above condensed imidazole compound, a pharmacologically acceptable salt thereof or hydrates thereof as the active ingredient; an agent for preventing or treating diabetic complications, which comprises the above condensed imidazole compound, a pharmacologically acceptable salt thereof or hydrates thereof as the active ingredient; an agent for preventing or treating diseases against which the above condensed imidazole compound, a pharmacologically acceptable salt thereof or hydrates thereof is effective; an agent for preventing or treating diabetic retinopathy, which comprises the above condensed imidazole compound, a pharmacologically acceptable salt thereof or hydrates thereof as the active ingredient; an adenosine A2 receptor antagonist comprising the above condensed imidazole compound, a pharmacologically acceptable salt thereof or hydrates thereof; and a pharmaceutical composition comprising the above condensed imidazole compound, a pharmacologically acceptable salt thereof or hydrates thereof and a pharmacologically acceptable carrier.

The present invention provides a method of preventing or treating diabetes mellitus, diabetic complications, diabetic retinopathy or diseases against which the above-mentioned condensed imidazole compound, a pharmacologically acceptable salt thereof or hydrates thereof is effective, or diseases against which an adenosine A2 receptor antagonism is effective, by administering a pharmacologically effective amount of the above-mentioned condensed imidazole compound, a pharmacologically acceptable salt thereof or hydrates thereof.

Further, the present invention provides use of the above-mentioned condensed imidazole compound, a pharmacologically acceptable salt thereof or hydrates thereof which is used for producing a preventive or therapeutic agent for diabetes mellitus, diabetic complications, diabetic retinopathy or diseases against which the above-mentioned condensed imidazole compound, a pharmacologically acceptable salt thereof or hydrates thereof is effective, or an adenosine A2 receptor antagonist.

The present invention relates to a useful intermediate for synthesis of the compound of the present invention, that is, 5-amino-1-methyl-2 (1H)-pyridone oxalate represented by the following formula:

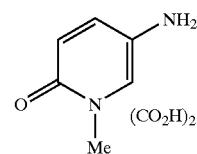

processes for producing the compound of the present invention and a synthetic intermediate of the compound of the present invention, that is, a process for producing an acylaminopyridine compound, acylaminopyrimidine compound or acylaminobenzene compound (A3) represented by the following formula:

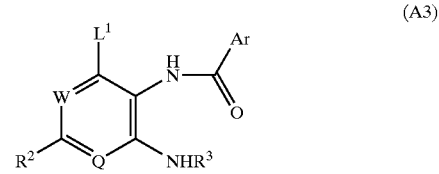

(wherein $L^1$, $R^2$, $R^3$, Ar, Q and W have the same meanings as defined below, respectively), a salt thereof or hydrates thereof, which comprises allowing an aminopyridine compound, aminopyrimidine compound or aminobenzene compound (A2) represented by the following formula:

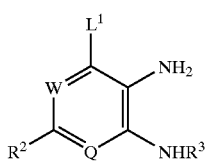

(A2)

(wherein L¹ represents a halogen atom; R² represents 1) hydrogen, 2) a halogen atom, 3) formula —NR⁶R⁷ (wherein R⁶ and R⁷ are the same as or different from each other and represent hydrogen, a C2–C5 acyl group, a C1–C8 alkyl group or a C3–C8 cycloalkyl group, or R⁶ and R⁷ represent a C2–C5 saturated cyclic amino group which is formed with a nitrogen atom to which they bind, whereupon this ring may contain an oxygen atom, a sulfur atom or a nitrogen atom other than the nitrogen atom and may be substituted with a C1–C4 alkyl group which may be substituted with a halogen atom), 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group, 6) a C1–C8 alkyl group which may be substituted with a halogen atom, hydroxyl or a C1–C4 alkyl group, or 7) a C1–C8 alkoxy group which may be substituted with a halogen atom, hydroxyl or a C1–C4 alkyl group; R³ represents 1) a C3–C8 alkynyl group which may be substituted with a halogen atom, a hydroxyl group or a C1–C4 alkyl group, 2) a C3–C8 alkenyl group which may be substituted with a halogen atom, a hydroxyl group or a C1–C4 alkyl group, 3) a C1–C8 alkyl group which may be substituted with a halogen atom, a hydroxyl group or a C1–C4 alkyl group, 4) an optionally substituted aryl group, 5) an optionally substituted heteroaryl group, 6) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group, and whose nitrogen atom is further substituted with b-1) a C1–C6 alkyl group which may be protected carboxyl group, b-2) an optionally substituted C3–C6 cycloalkyl-C1–C4 alkyl group or b-3) a C3–C6 cycloalkyl group or 8) a dihydroxo or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxy, b-2) an optionally substituted C3–C6 cycloalkyl-C1–C4 alkyl group, or b-3) a C3–C6 cycloalkyl group; and Q and W are the same as or different from each other and each represents N or CH), to react with an acyl compound represented by the formula ArCOX (wherein X represents a halogen atom; and Ar represents 1) an optionally substituted aryl group, 2) an optionally substituted heteroaryl group, 3) an oxopyridyl group which may be substituted with a halogen atom or a C1–C6 alkyl group and whose nitrogen atom is substituted with a C1–C6 alkyl group or a C3–C6 cycloalkyl group, or 4) an oxopyrimidyl group which may be substituted with a halogen atom or a C1–C6 alkyl group and whose nitrogen atom is substituted with a C1–C6 alkyl group or a C3–C6 cycloalkyl group);

a process for producing an acylaminopyridine compound, acylaminopyrimidine compound or acylaminobenzene compound (A3) represented by the following formula:

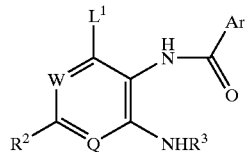

(A3)

(wherein L¹, R², R³, Ar, Q and W have the same meanings as defined above, respectively), a salt thereof or hydrates thereof, which comprises allowing an aminopyridine compound, aminopyrimidine compound or aminobenzene compound (A2) represented by the following formula:

(A2)

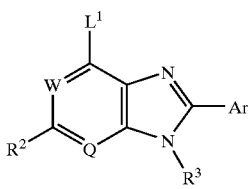

(wherein L¹, R², R³, Q and W have the same meanings as defined above, respectively) to react in the presence of pyridine with an acyl compound represented by the formula ArCOX (wherein X and Ar have the same meanings as defined above, respectively);

the above-mentioned process for producing an acylaminopyridine compound, acylaminopyrimidine compound or anylaminobenzene compound (A3), a salt thereof or hydrates thereof, wherein R³ is an N-C1–C8 alkyl-2-oxopyrimidinyl group;

a process for producing an imidazopyridine compound, imidazopyrimidine compound or imidazobenzene compound (A4), a salt thereof or hydrates thereof represented by the following formula:

(A4)

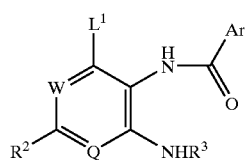

(wherein L¹, R², R³, Ar, Q and W have the same meanings as defined above, respectively), which comprises subjecting an acylaminopyridine compound, acylaminopyrimidine compound or acylaminobenzene compound (A3) represented by the following formula:

(A3)

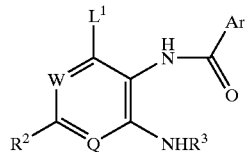

(wherein L¹, R², R³, Ar, Q and W have the same meanings as defined above, respectively) to ring-closure reaction in the presence of POCl₃;

a process for producing an imidazopyridine compound, imidazopyrimidine compound or imidazobenzene compound (A4), a salt thereof or hydrates thereof represented by the following formula:

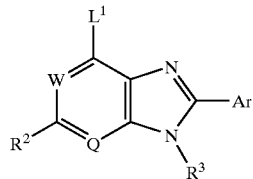

(A4)

(wherein $L^1$, $R^2$, $R^3$, Ar, Q and W have the same meanings as defined above, respectively), which comprises subjecting an acylaminopyridine compound, acylaminopyrimidine compound or acylaminobenzene compound (A3) represented by the following formula:

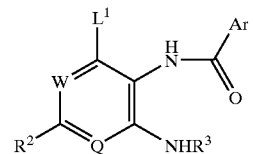

(A3)

(wherein $L^1$, $R^2$, $R^3$, Ar, Q and W have the same meanings as defined above, respectively) to ring-closure reaction in the presence of hydrochloric acid or using hydrochloride of an acylaminopyridine compound, acylaminopyrimidine compound or acylaminobenzene compound (A3);

a process for producing an imidazopyridine compound, imidazopyrimidine compound or imidazobenzene compound (A4), a salt thereof or hydrates thereof represented by the following formula:

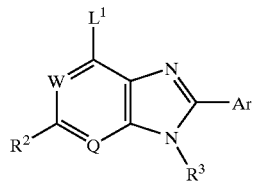

(A4)

(wherein $L^1$, $R^2{}_1$ $R^3$, Ar, Q and W have the same meanings as defined above, respectively), which comprises subjecting an acylaminopyridine compound, acylaminopyrimidine compound or acylaminobenzene compound (A3) represented by the following formula:

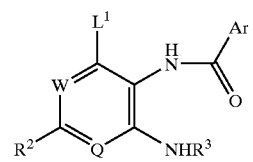

(A3)

(wherein $L^1$, $R^2$, $R^3$, Ar, Q and W have the same meanings as defined above, respectively) to ring-closure reaction in NMP (1-methyl-2-pyrrolidone) under heating;

the above-mentioned process for producing an imidazopyridine compound, imidazopyrimidine compound or imidazobenzene compound (A4), a salt thereof or hydrates thereof, wherein $R^3$ is an N-C1–C8 alkyl-2-oxopyridinyl group;

a process for producing an imidazopyridine compound, imidazopyrimidine compound or imidazobenzene compound (A4), a salt thereof or hydrates thereof represented by the following formula:

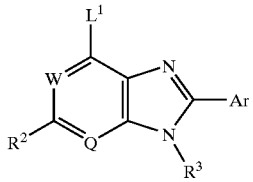

(A4)

(wherein $L^1$, $R^2$, $R^3$, Ar, Q and W have the same meanings as defined above, respectively), which comprises allowing an aminopyridine compound, aminopyrimidine compound or aminobenzene compound (A2) represented by the following formula:

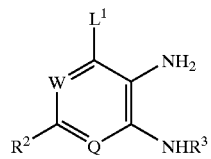

(A2)

(wherein $L^1$, $R^2$, $R^3$, Q and W have the same meanings as defined above, respectively) to react with an acyl compound represented by the formula ArCOX (wherein X and Ar have the same meanings as defined above, respectively); and then subjecting the product to ring-closure reaction;

the above-mentioned process for producing an imidazopyridine compound, imidazopyrimidine compound or imidazobenzene compound (A4), a salt thereof or hydrates thereof, wherein the aminopyridine compound, aminopyrimidine compound or aminobenzene compound (A2) is converted in one-pot reaction into the imidazopyridine compound, imidazopyrimidine compound or imidazobenzene compound (A4);

a process for producing an aminoimidazopyridine compound, aminomidazopyrimidine compound or aminoimidazobenzene compound (A5), a salt thereof or hydrates thereof represented by the formula:

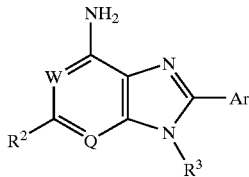

(A5)

(wherein $L^1$, $R^2$, $R^3$, Ar, Q and W have the same meanings as defined above, respectively), which comprises aminating an imidazopyridine compound, imidazopyrimidine compound or imidazobenzene compound (A4) represented by the following formula:

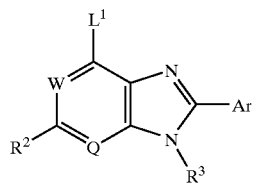

(A4)

(wherein $L^1$, $R^2$, $R^3$, Ar, Q and W have the same meanings as defined above, respectively);

the above-mentioned process for producing an aminoimidazopyridine compound, aminoimidazopyrimidine compound or aminoimidazobenzene compound (A5), a salt thereof or hydrates thereof, wherein $R^3$ is an N-C1–C8 alkyl-2-oxopyridinyl group; and a process for producing an imidazopyridine compound, imidazopyrimidine compound or imidazobenzene compound (C3), a salt thereof or hydrates thereof represented by the formula:

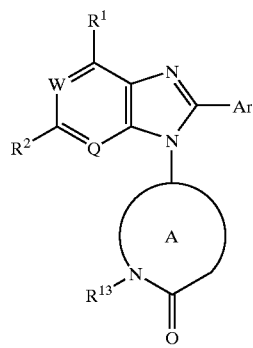

(C3)

(wherein $R^{13}$ means a C1–C6 alkyl group which may be substituted with a halogen atom, hydroxyl or an optionally protected carboxyl group, an optionally substituted C3–C6 cycloalkyl-C1–C4 alkyl group, or an optionally substituted C3–C6 cycloalkyl group; and $R^1$, the formula:

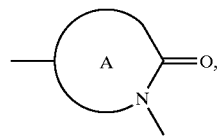

$R^2$, Ar, Q and W have the same meanings as defined above, respectively), which comprises alkylating an imidazopyridine compound, imidazopyrimidine compound or imidazobenzene compound (C2) represented by the following formula:

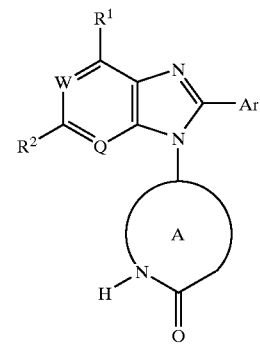

(C2)

(wherein $R^1$ represents 1) hydrogen, 2) hydroxyl, 3) a halogen atom, 4) an optionally substituted C1–C8 alkyl group or 5) formula —$NR^4R^5$ (wherein $R^4$ and $R^5$ are the same as or different from each other and each represents hydrogen, a C1–C8 alkyl group or a C3–C8 cycloalkyl group, or a C2–C5 saturated cyclic amino group which is formed with a nitrogen atom to which they bind, whereupon this ring may contain oxygen, sulfur or nitrogen other than the nitrogen atom and may be substituted with a C1–C4 alkyl group which may be substituted with a halogen atom; the formula:

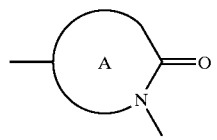

represents dihydrooxopyridinyl or -pyrimidyl, or dihydro- or tetrahydropyrazinyl; and $R^2$, Ar, Q and W have the same meanings as defined above, respectively.

In the definition of $R^1$, $R^3$ and Ar in the formula (I), the term "optionally substituted", for example an optionally substituted aryl group, an optionally substituted heteroaryl group, an optionally substituted C1–C8 alkyl group etc., means that each group may be substituted with a group selected from hydroxyl; thiol group; nitro group; cyano group; a halogen atom such as fluorine, chlorine, bromine and iodine; a C1–C8 alkyl group such as methyl, ethyl, n-propyl and isopropyl; C1–C8 alkoxy group such as methoxy, ethoxy, n-propoxy, isopropoxy and butoxy; halogenated alkyl group such as fluoromethyl group, difluoromethyl group, trifluoromethyl group and 2,2,2-trifluoroethyl group; alkyl thio group such as methyl thio group, ethyl thio group and isopropyl thio group; acyl group such as acetyl group, propionyl group and benzoyl group; hydroxyalkyl group such as hydroxymethyl group, hydroxyethyl group and hydroxypropyl group; amino group; monoalkyl amino group such as methyl amino group, ethyl amino group and isopropyl amino group; dialkyl amino group such as dimethyl amino group and diethyl amino group; cyclic amino group such as aziridinyl group, azetidinyl group, pyrrolidinyl group, piperidinyl group, perhydroazepinyl group and piperazinyl group; carboxyl; alkoxycarbonyl group such as methoxycarbonyl group, ethoxycarbonyl group and propylcarbonyl group; carbamoyl group; alkyl carbamoyl group such as methyl carbamoyl group and dimethyl carbamoyl group; acyl amino group such as acetyl amino group and benzoyl amino group; unsubstituted sulfamoyl or sulfamoyl substituted with a C1–C4 alkyl group; alkyl sulfonyl group such as methyl sulfonyl group and ethyl sulfonyl group;

unsubstituted or substituted aryl sulfonyl group such as benzene sulfonyl group and p-toluene sulfonyl group; unsubstituted or substituted aryl group such as phenyl group, tolyl group and anisolyl group; unsubstituted or substituted heteroaryl group such as pyrrole group, pyrazolyl group, imidazolyl group, triazolyl group, tetrazolyl group, thiazolyl group, pyridyl group, pyrimidyl group and pyrazinyl group; carboxyalkyl group; alkyloxycarbonyl alkyl group such as methoxycarbonyl methyl group, ethoxycarbonyl methyl group and methoxycarbonyl ethyl group; carboxyalkoxy group such as carboxymethoxy group; aryl alkyl group such as benzyl group and 4-chlorobenzyl group; heteroaryl alkyl group such as pyridyl methyl group and pyridyl ethyl group; alkylene dioxy group such as methylene dioxy group and ethylene dioxy group; and oxo group.

The halogen atom in the definition of $R^1$, $R^2$ and $R^3$ means fluorine, chlorine, bromine and iodine.

The C1–C4, C1–C6 or C1–C8 alkyl group in the definition of $R^1$, $R^2$ and $R^3$ means a linear or branched alkyl group having 1–4, 1–6 or 1–8 carbon atoms, respectively. Examples thereof include methyl group, ethyl group, n-propyl group, isopropyl group, n-butyl group, isobutyl group, sec-butyl group, t-butyl group, n-pentyl group, 1,2-dimethyl propyl group, 1,1-dimethyl propyl group, 2,2-dimethyl propyl group, 2-ethyl propyl group, n-hexyl group, 1,2-dimethyl butyl group, 2,3-dimethyl butyl group, 1,3-dimethylbutyl group, 1-ethyl-2-methylpropylgroup, 1-methyl-2-ethyl propyl group, n-heptyl group, 1,1-dimethyl pentyl group, 2-ethyl pentyl group, 1-methyl-2-ethyl butyl group, n-octyl group, 1,1-dimethyl hexyl group, 2-ethyl hexyl group, 1-methyl-2-ethyl pentyl group etc.

The cycloalkyl group in the definition of $R^1$, $R^2$ and $R^3$ means $C_{3-8}$ cycloalkyl group such as cyclopropyl group, cyclobutyl group, cyclopentyl group, cyclohexyl group, cycloheptyl group or cyclooctyl group.

The C3–C6 cycloalkyl-C1–C4 alkyl group in the definition of $R^3$ means a group having $C_{3-6}$ cycloalkyl group such as cyclopropyl group, cyclobutyl group, cyclopentyl group or cyclohexyl group bound to the above-mentioned C1–C4 alkyl group.

In the definition of $R^2$ and $R^3$, the C3–C8 alkenyl group and a linear or branched alkenylgroup include e.g. 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group etc.

The acyl group in the definition of $R^2$ includes aliphatic saturated monocarboxylic acid-derived groups such as acetyl group, propionyl group, butyryl group, valeryl group, isovaleryl group and pivaloyl group; aliphatic unsaturated carboxylic acid-derived groups such as acryloyl group, propioloyl group, methacryloyl group, crotonyl group and isocrotonyl group; carbon-cyclic-carboxylic acid-derived groups such as benzoyl group, naphthoyl group, toluoyl group, hydroatropoyl group, atropoyl group and cinnamoyl group; heterocyclic carboxylic acid-derived groups such as furoyl group, thenoyl group, nicotinoyl group and isonicotinoyl group; hydroxycarboxylic acid- or alkoxycarboxylic acid-derived groups such as glycoloyl group, lactoyl group, glyceroyl group, tropoyl group, benziloyl group, salicyloyl group, anisoyl group, vanilloyl group, piperonyloyl group, galloyl group; or groups derived from various amino acids.

In the definition of $R^3$ and Ar, the aryl group which may have a substituent group includes phenyl group, 1-naphthyl group, 2-naphthyl group, anthracenyl gtoup etc.

In the optionally substituted heteroaryl group in the definition of $R^3$ and Ar, the heteroaryl group includes groups derived from a single or fused ring containing 1 to 4 atoms selected from sulfur, oxygen and nitrogezn. Examples thereof include pyrrolyl group, thienyl group, furyl group, thiazolyl group, oxazolyl group, isothiazolyl group, isoxazolyl group, imidazolyl group, pyrazolyl group, thiadiazolyl group, oxadiazolyl group, triazolyl group, tetrazolyl group, pyridyl group, pyridazinyl group, pyrimidinyl group, pyrazinyl group, indolyl group, isoindolyl group, benzothienyl group, benzofuranyl group, isobenzofuranyl group, benzimidazolyl group, indazolyl group, benzotriazolyl group, benzothiazolyl group, benzoxazolyl group, quinolyl group, isoquinolyl group, cinnolinyl group, phthalazyl group, quinoxalyl group, naphthyridinyl group, quinazolinyl group, imidazopyridinyl group etc.

In the nitrogen-containing heteroaryl groups described above, if a hydroxyl group is bound to a carbon atom adjacent to the nitrogen atom, then the present compound encompasses its tautomer i.e. —NH— oxo derivative.

In the optionally protected carboxyl group in the definition of $R^3$, theprotective group includes e.g. C1–C8 alkyl group such as methyl group, ethyl group and tert-butyl group; C1–C8 alkyl group substituted with an optionally substituted phenyl group such as p-methoxybenzyl, p-nitrobenzyl, 3,4-dimethoxybenzyl, diphenylmethyl, trityl and phenetyl; halogenated C1–C8 alkyl group such as 2,2,2-trichloroethyl and 2-iodoethyl; C1–C8 alkanoyloxy C1–C8 alkyl group such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy C1–C8 alkyl group such as palmitoyloxyethyl, heptadecanoyloxymethyl and 1-palmitoyloxyethyl; C1–C8 alkoxycarbonyloxy C1–C8 alkyl group such as methoxycarbonyloxymethyl, 1-butoxycarbonyloxyethyl and 1-(isopropoxycarbonyloxy)ethyl; carboxy C1–C8 alkyl group such as carboxymethyl and 2-carboxyethyl; heteroaryl group such as 3-phthalidyl group; an optionally substituted benzoyloxy C1–C8 alkyl group such as 4-glycyloxybenzoyloxymethyl; (substituted dioxolene) C1–C8 alkyl group such as (5-methyl-2-oxo-1,3-dioxolene-4-yl)methyl; cycloalkyl substituted C1–C8 alkanoyloxy C1–C8 alkyl group such as 1-cyclohexylacetyloxyethyl; and cycloalkyloxycarbonyloxy C1–C8 alkylgroupsuchasl-cyclohexyloxycarbonyloxyethyl. Further, the substituent group may be various acid amides. In short, any groups which may be degraded in vivn by some means to form carboxylic acids can be used as the protective group for the carboxyl group.

In the definition of $R^4$, $R^5$, $R^6$ and $R^7$, the term "C2–C5 saturated cyclic amino group which is formed with a nitrogen atom to which they bind" refers to aziridine, azetidine, pyrrolidine, piperidine, piperazine, homopiperazine, morpholine or thiomorpholine. These rings may be substituted with a C1–C4 alkyl group which may be substituted with a halogen atom.

Q and W are the same as or different from each other and each represents N or CH, preferably a nitrogen atom.

$R^1$ represents 1) hydrogen, 2) hydroxyl, 3) a halogen atom, 4) an optionally substituted C1–C8 alkyl group or 5) formula —$NR^4R^5$ (wherein $R^4$ and $R^5$ are the same as or different from each other and each represents hydrogen, a C1–C8 alkyl group, a C3–C8 cycloalkyl group, or a C2–C5 saturated cyclic amino group which is formed with a nitrogen atom to which they bind, whereupon this ring may contain oxygen, sulfur or nitrogen other than the mentioned nitrogen atom and may be substituted with a C1–C4 alkyl group which may be substituted with a halogen atom), preferably 2) hydroxyl, 3) ahalogen atom, 4) a C1–C alkyl group which may have a substituent group, or 5) formula —NR$^4$R$^5$ (wherein R$^4$ and R$^5$ are the same as or different from each other and each represents hydrogen, a C1–C8 alkyl group, a C3–C8 cycloalkyl group or a C2–C5 saturated cyclic amino group which is formed with a nitrogen atom to which they bind, whereupon this ring may contain oxygen, sulfur or nitrogen other than the mentioned nitrogen atom and may be substituted with a C1–C4 alkyl group which may be substituted with a halogen atom), more preferably 2) hydroxyl, 4) an optionally substituted C1–C8 alkyl group or 5) formula —NR$^4$R$^5$ (wherein R$^4$ and R$^5$ are the same as or different from each other and each represents hydrogen, a C1–C8 alkyl group, a C3–C8 cycloalkyl group or a C2–C5 saturated cyclic amino group which is formed with a nitrogen atom to which they bind, whereupon this ring may contain oxygen, sulfur or nitrogen other than the mentioned nitrogen atom and may be substituted with a C1–C4 alkyl group which may be substituted with a halogen atom), further preferably 4) an optionally substituted C1–C8 alkyl group or 5) formula —NR$^4$R$^5$ (wherein R$^4$ and R$^5$ are the same as or different from each other and each represents hydrogen, a C1–C8 alkyl group, a C3–C8 cycloalkyl group or a C2–C5 saturated cyclic amino group which is formed with a nitrogen atom to which they bind, whereupon this ring may contain oxygen, sulfur or nitrogen other than the mentioned nitrogen atom and may be substituted with a C1–C4 alkyl group which may be substituted with a halogen atom, and further more preferably 5) formula —NR$^4$R$^5$ (wherein R$^4$ and R$^5$ are the same as or different from each other and each represents hydrogen, a C1–C8 alkyl group, a C3–C8 cycloalkyl group, or a C2–C5 saturated cyclic amino group which is formed with a nitrogen atom to which they bind, whereupon this ring may contain oxygen, sulfur or nitrogen other than the mentioned nitrogen atom and may be substituted with a C1–C4 alkyl group which may be substituted with a halogen atom).

R$^2$ represents 1) hydrogen, 2) a halogen atom, 3) formula —NR$^6$R$^7$ (wherein R$^6$ and R$^7$ are the same as or different from each other and each represents hydrogen, a C2–C5 acyl group, a C1–C8 alkyl group or a C3–C8 cycloalkyl group, or R$^6$ and R$^7$ represent a C2–C5 saturated cyclic amino group which is formed with a nitrogen atom to which they bind, whereupon this ring may contain oxygen, sulfur or nitrogen other than the above-mentioned nitrogen and may be substituted with a C1–C4 alkyl group which may be substituted with a halogen atom, 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group, 6) a C1–C8 alkyl group which may be substituted with a halogen atom, hydroxyl or a C1–C4 alkyl group, or 7) a C1–C8 alkoxy group which may be substituted with a halogen atom, hydroxyl group or a C1–C4 alkyl group, preferably 1) hydrogen, 2) a halogen atom, 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group, 6) a C1–C8 alkyl group which maybe substituted with a halogen atom, hydroxyl ora C1–C4 alkyl group, or 7) a C1–C8 alkoxy group which may be substituted with a halogen atom, hydroxyl or a C1–C4 alkyl group, more preferably 1) hydrogen atom, 2) a halogen atom, 4) a C2–C8 alkynyl group which may be substituted with a halogen atom, hydroxyl, a C1–C4 alkyl group or a C3–C6 cycloalkyl group, 6) a C1–C8 alkyl group which may be substituted with a halogen atom, hydroxyl or a C1–C4 alkyl group, or 7) a C1–C8 alkoxy group which may be substituted with a halogen atom, hydroxyl or a C1–C4 alkyl group, further preferably 1) hydrogen, 4) a C2–C8 alkynyl group which may be substituted with a halogen atom, hydroxyl, a C1–C4 alkyl group or a C3–C6 cycloalkyl group, 6) a C1–C8 alkyl group which may be substituted with a halogen atom, hydroxyl or a C1–C4 alkyl group, or 7) a C1–C8 alkoxy group which may be substituted with a halogen atom, hydroxyl or a C1–C4 alkyl group, more preferably 1) hydrogen, 4) a C2–C8 alkynyl group which may be substituted with a halogen atom, hydroxyl, a C1–C4 alkyl group or a C3–C6 cycloalkyl group, or 6) a C1–C8 alkyl group which may be substituted with a halogen atom, hydroxyl or a C1–C4 alkyl group, still more preferably 1) hydrogen or 6) a C1–C8 alkyl group which maybe substituted with a halogen atom, hydroxyl ora C1–C4 alkyl group, and most preferably hydrogen.

R$^3$ represents 1) a C3-C8 alkynyl group which may be substituted with ahalogen atom, hydroxyl ora C1–C4 alkyl group, 2) a C3–C8 alkenyl group which may be substituted with a halogen atom, hydroxyl or a C1–C4 alkyl group, 3) a C1–C8 alkyl group which may be substituted with a halogen atom, hydroxyl or a C1–C4 alkyl group, 4) an optionally substituted aryl group, 5) an optionally substituted heteroaryl group, 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, a hydroxyl or an optionally protected carboxyl group, b-2) an optionally substituted C3–C6 cycloalkyl-C1–C4 alkyl group or b-3) a C3–C6 cycloalkyl group, preferably 2) a C3–C8 alkenyl group which may be substituted with a halogen atom, hydroxyl or a C1–C4 alkyl group, 3) a C1–C8 alkyl group which may be substituted with a halogen atom, hydroxyl or a C1–C4 alkyl group, 4) an optionally substituted aryl group, 5) an optionally substituted heteroaryl group, 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, a hydroxyl or an optionally protected carboxyl group, b-2) an optionally substituted C3–C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, more preferably 2) a C3–C8 alkenyl group which may be substituted with a halogen atom, hydroxyl or a C1–C4 alkyl group, 5) an optionally substituted heteroaryl group, 6) a 1,2-dihydro-2-oxopyridyl group which may be substituted with a) a halogen atom or a C1–C6 alkyl group and whose nitrogen atom may further be substituted with b-1) a C1–C6 alkyl group which maybe substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3-C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with halogen atom, hydroxyl or an optionally protected carboxyl group, b-2) an optionally substituted C3–C6 cycloalkyl-C1–C4 alkyl group or b-3) a C3–C6 cycloalkyl group, further preferably 5) an optionally substituted heteroaryl group, 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, further more preferably 6) a 1,2-dihydro-2-oxopyridyl group which may be substituted with a) a halogen atom or a C1–C6 alkyl group and whose nitrogen atom may further be substituted with b-1) a C1–C6 alkyl group which maybe substituted with ahalogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, a hydroxyl or an optionally protected carboxyl group, b-2) an optionally substituted C3–C6 cycloalkyl-C1–C4 alkyl group or b-3) a C3–C6 cycloalkyl group, more preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally protected C3–C6 cycloalkyl-C1–C4 alkyl group or b-3) an optionally substituted C3–C6 cycloalkyl group, or 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) a C3–C6 cycloalkyl-C1–C4 alkyl group which may have a substituent group or b-3) a C3–C6 cycloalkyl group, still further preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, still further more preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, and most preferably 1,2-dihydro-2-oxopyridyl group or 1-methyl-1,2-dihydro-2-oxopyridyl group.

$R^3$ has the meanings as defined above, but when $R^2$ is i) a C2–C8 alkynyl group which may be substituted with a halogen atom, hydroxyl, a C1–C4 alkyl group or a C3–C6 cycloalkyl group, ii) a C3–C8 alkenyl group which may be substituted with a halogen atom, hydroxyl or a C1–C4 alkyl group, or iii) a C1–C8 alkyl group which may be substituted with a halogen atom, hydroxyl or a C1–C4 alkyl group, R is not i) a C1–C8 alkyl group which may be substituted with ahalogen atom, hydroxyl or a C1–C4 alkyl group or ii) an optionally substituted aryl group.

In this case, when $R^2$ is i) a C2–C8 alkynyl group which may be substituted with a halogen atom, hydroxyl, a C1–C4 alkyl group or a C3–C6 cycloalkyl group, ii) a C3–C8 alkenyl group which may be substituted with a halogen atom, hydroxyl or a C1–C4 alkyl group or iii) a C1–C8 alkyl group which may be substituted with a halogen atom, hydroxyl or a C1–C4 alkyl group, $R^3$ represents 1) a C3–C8 alkynyl group which may be substituted with a halogen atom, hydroxyl or a C1–C4 alkyl group, 2) a C3–C8 alkenyl group which may be substituted with a halogen atom, hydroxyl or a C1–C4 alkyl group, 5) an optionally substituted heteroaryl group, 6) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, preferably 5) an optionally substituted heteroaryl group, 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group b-3) a C3–C6 cycloalkyl group or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl, b-2) an optionally substituted C3–C6 cycloalkyl-C1–C4 alkyl group or b-3) a C3–C6 cycloalkyl group, more preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, or 8) a dihydroxo- or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, further more preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, or 7) a dihydroxopyrimidyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group, further preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally protected carboxyl, b-2) an optionally substituted C3–C6 cycloalkyl-C1–C4 alkyl group or b-3) an optionally substituted C3–C6 cycloalkyl group, still further preferably 6) a 1,2-dihydro-2-oxopyridyl group which may be substituted with a) a halogen atom or a C1–C6 alkyl group and whose nitrogen atom may further be substituted with b-1) a C1–C6 alkyl group which may be substituted with a halogen atom, hydroxyl or an optionally a9 protected carboxyl group, and most preferably a 1,2-dihydro-2-oxopyridyl group or a 1-methyl-1,2-dihydro-2-oxopyridyl group.

Ar represents 1) an optionally substituted aryl group, 2) an optionally substituted heteroaryl group, 3) an oxopyridyl group which may be substituted with a halogen atom or a C1–C6 alkyl group and whose nitrogen atom is further substituted with a C1–C6 alkyl group or a C3–C6 cycloalkyl group or 4) an oxopyrimidyl group which may be substituted with a halogen atom or a C1–C6 alkyl group and whose nitrogen atom is further substituted with a C1–C6 alkyl group or a C3–C6 cycloalkyl group, 1) an optionally substituted aryl group, 2) an optionally substituted heteroaryl group or 3) an oxopyridyl group which may be substituted with a halogen atom or a C1–C6 alkyl group and whose nitrogen atom is further substituted with a C1–C6 alkyl group or a C3–C6 cycloalkyl group, further preferably 1) an optionally substituted aryl group or 2) an optionally substituted heteroaryl group, still further preferably an optionally substituted aryl group, and most preferably an optionally substituted phenyl group.

It goes without saying that when the compounds of the present invention have an asymmetric atom, optically active isomers thereof also fall under the scope of the present invention. Further, the present invention encompasses hydrates.

In the present invention, the pharmacologically acceptable salts include e.g. inorganic salts such as hydrochloride, hydrobromate, sulfate, and phosphate; organic acid salts such as acetate, maleate, tartrate, methanesulfonate, benzene sulfonate and toluene sulfonate, or salts with amino acids such as aspartic acid and glutamic acid.

The compound group of the present invention is also useful because of low toxicity and high safety.

When the compound of the present invention is used as the diseases described above, it can be administered orally or parenterally. The compound of the present invention can be administered in the form of tablets, powder, granules, capsules, syrups, troches, inhalations, suppositories, injections, ointments, eye ointments, eye drops, nose drops, ear drops, poultices and lotions.

Although the dose is significantly varied depending on the type of disease, the severeness of symptoms, the age and sex, the sensitivity to the chemical of a patient, the present compound is administered into a man in one portion or divided portions in a daily dose of usually about 0.03 to 1000 mg, preferably 0.1 to 500 mg, more preferably 0.1 to 100 mg. The dose of the injection is usually about 1 $\mu$g/kg to 3000 $\mu$g/kg, preferably about 3 $\mu$g/kg to 1000 $\mu$g/kg.

The compound of the present invention can be formed into a pharmaceutical preparation in a usual manner by using usual pharmaceutical carriers.

That is, when the oral solid pharmaceutical preparation is to be prepared, excipients as the major ingredient, a binder, a disintegrating agent, a lubricant, a coloring agent, flavoring agent, and an antioxidant are added to the compound of the present invention and formed in a usual manner into tablets, coated tablets, granules, powder, capsules etc.

The fillers include e.g. lactose, corn starch, white sugar, glucose, sorbitol, crystalline cellulose, silicon dioxide etc.

The binder includes e.g. polyvinyl alcohol, polyvinyl ether, ethyl cellulose, methyl cellulose, gum arabic, tragacanth, gelatin, shellac, hydroxy propyl cellulose, hydroxy propyl methyl cellulose, calcium citrate, dextrin, pectin etc., and the lubricant includes e.g. magnesium stearate, talc, polyethylene glycol, silica, hardened vegetable oil etc.

The coloring agent includes e.g. those coloring agents approved to be added to pharmaceutical preparations, and the flavoring agent include cocoa powder, menthol, aromatic powder, peppermint oil, borneol, cinnamon powder etc. The antioxidant includes ascorbic acid, α-tocopherol etc. which are approved to be added to pharmaceutical preparations. The tablets and granules may be coated as necessary with sugar coating, gelatin coating etc.

On the other hand, when the injection preparation, eye drops etc. are to be produced, a pH adjuster, a buffer, a suspension agent, a solubilizer, a stabilizer, an isotonizing agent, an antioxidant, a preservative etc. may be added to the major chemical and formed in a usual manner into the preparation. If necessary, the preparation can be formed into a freeze-dried preparation. The injection can be administered intravenously, subcutaneously or intramuscularly.

Examples of the suspension agent include methyl cellulose, Polysorbate 80, hydroxyethyl cellulose, gum arabic, tragacanth powder, sodium carboxymethyl cellulose and polyoxyethylene sorbitan monolaurate.

The solubilizer includes polyoxyethylene hardened castor oil, Polysorbate 80, nicotinic acid amide, polyoxyethylene sorbitan monolaulate.

The stabilizer includes e.g. sodium sulfite, sodium metasulfite and ether, and the preservative includes e.g. methyl p-oxybenzoate, ethyl p-oxybenzoate, sorbic acid, phenol, cresol, chlorocresol etc.

When the ointment is to be produced, the preparation can be produced in a usual manner by adding a stabilizer, an antioxidant and a preservative as necessary.

The novel purine compound of the present invention can be produced by combination of generally known methods. Hereinafter, the major conventional method of producing the compound group of the present invention is described.

Production Method A

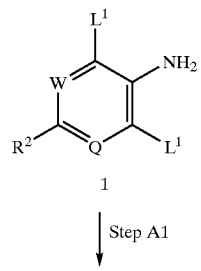

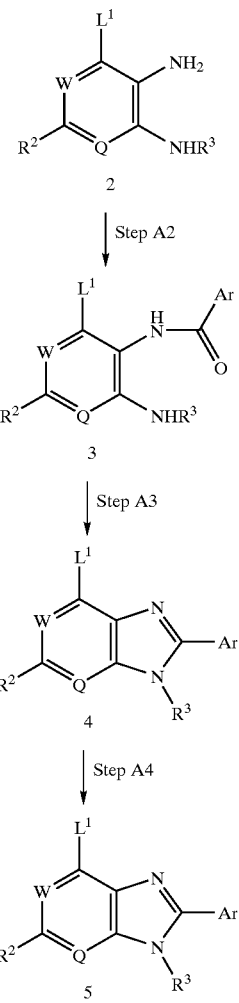

wherein $L^1$ means a halogen atom, and $R^1$, $R^2$, $R^3$, Ar, Q and W have the same meanings as defined above.

Step A1: This step is the step of allowing a compound 5-amino-4,6-dihalogeno-2-pyrimidine 1 synthesized in accordance with a known method to react in a solvent with various primary amine compounds to replace a halogen atom at the 4-position by the amine derivatives, to produce 4, 5-diaminopyrimidine derivative 2.

The reaction is carried out using an amine in excess, or in the presence of a tertiary amine such as triethylamine and diisopropyl ethylamine when the amine reacted is an alkyl amine, alkynyl amine and allyl amine, or in the presence of a catalytic amount of mineral acid, preferably with the coexistence of hydrochloric acid when the amine reacted is an aryl amine or heteroaryl amine. However, the reaction may be carried out in the absence of hydrochloric acid using carboxylate thereof.

The solvent used is not particularly limited insofar as the reaction is not inhibited and the starting material is dissolved to a certain extent, and preferable examples include NMP (1-methyl-2-pyrrolidone); ethers such as tetrahydrofuran, dioxane, dimethoxyethane and diethylene glycol dimethyl ether; halogenated hydrocarbons such as methylene chloride, chloroform and dichloroethane. When the amine reacted is an aryl amine or heteroaryl amine, a mixed solvent of alcohol and water can be used. The reaction temperature is varied depending on the reactivity of the amine derivative used, preferably from room temperature to the boiling point of each solvent, more preferably a temperature at which the reaction solution is refluxed.

Step A2: This step is the step of reacting ArCOX (wherein X is a halogen atom; and Ar has the same meaning as defined above) with 4,5-diaminopyrimidine derivative 2, to produce 5-acylaminopyrimidine derivative 3.

This reaction is carried out at a temperature ranging from 0° C. to room temperature in pyridine or in the presence of a base in a solvent not participating in the reaction such as methylene chloride, chloroform, ethyl acetate, tetrahydrofuran, dioxane, dimethoxyethane, benzene and toluene.

Step A3: This step is the step of dehydration condensation of the acyl amino group with its adjacent substituted amino group on the pyrimidine ring to form an imidazole ring, thus producing purine derivative 4.

The reaction is carried out under reflux in phosphorus oxychloride. The reaction can also be conducted in the presence of hydrochloric acid. Further, the reaction can also be conduced under heating in NMP.

The steps A2 and A3 can also proceed in one-pot reaction.

Step A4: This step is the step of allowing a halogen atom at the 6-position in the purine derivative A to react with an amine derivative, to produce 6-amino-8,9-di-substituted purine derivative 5.

When the amine derivative is gas or has a low boiling point, the reaction is carried out preferably in a sealed tube or in an autoclave.

The solvent used is not particularly limited insofar as the reaction is not inhibited and the starting material is dissolved to a certain extent, and preferable examples include alcohols such as methanol and ethanol; ethers such as tetrahydrofuran, dioxane, dimethoxyethane and diethylene glycol dimethyl ether; halogenated hydrocarbons such as methylene chloride, chloroform and dichloroethane; dimethylformamide, 1-methyl pyrrolidinone etc.

The reaction temperature is preferably 0 to 150° C., more preferably 50 to 100° C.

Production method B

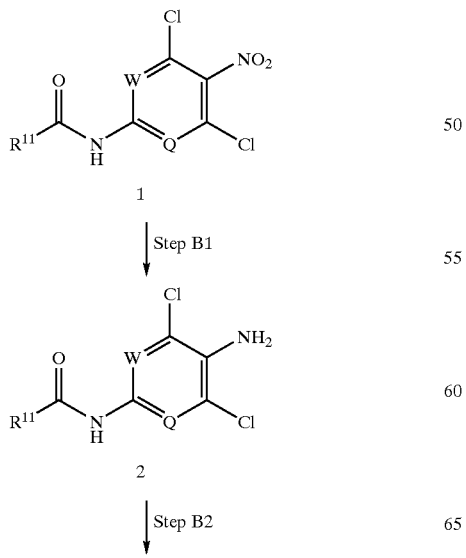

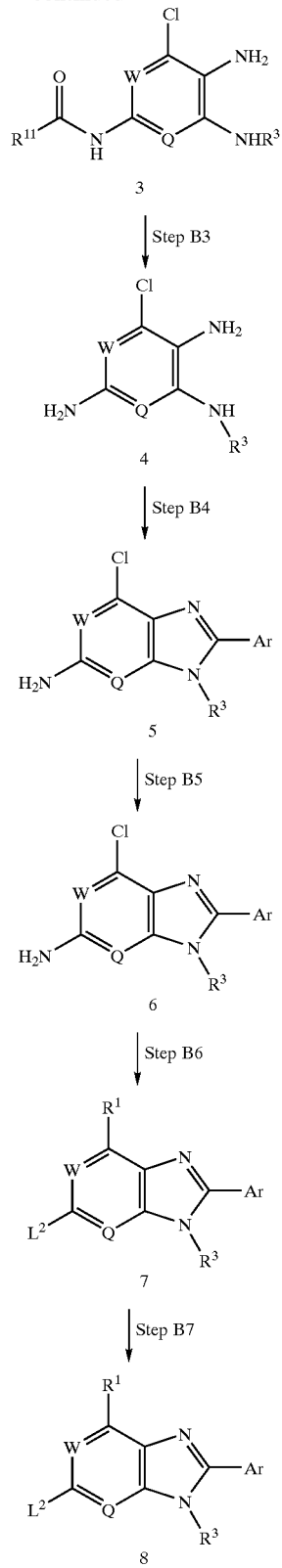

wherein $L^2$, $R^1$, $R^2$, $R^3$, Ar, Q and W have the same meanings as defined above; and $R^{11}$ means a C1–C4 alkyl group.

Step B1: This step is the step of subjecting the nitro group in 2-acylamino-4,6-dichloro-5-nitropyrimidine derivative 1 produced in a known method to catalytic reduction, reduction with a metal or a metal salt, or reduction with a metal hydride, to produce 2-acylamino-5-amino-4,6-dichloropyrimidine derivative 2.

The catalytic reduction is conducted at normal pressure or under pressure, at room temperature or under heating, in the presence of a catalyst such as Raney Ni, Pd—C or $PtO_2$ in a hydrogen atmosphere. It is conducted preferably at normal pressure and at ordinary temperature, more preferably in the presence of Raney Ni as the catalyst at normal pressure and at ordinary temperature. The solvent used is not particularly limited insofar as it dissolves the starting material to a certain extent without causing catalytic poison, and preferable examples include methanol, ethanol, tetrahydrofuran, dioxane, acetic acid, dimethylformamide or a mixed solvent thereof. The reduction with a metal or a metal salt is conducted using zinc powder-hydrochloric acid, stannouschloride-hydrochloric acid, or iron-hydrochloric acid in an alcohol such as hydrous or anhydrous methanol or ethanol or in dioxane or tetrahydrofuran as the solvent. The reduction with a metal hydride is conducted using Pd-sodium borohydride, $NiCl_2(PPh_3)_2$-sodium borohydride, or stannous chloride-sodium borohydride in a methanol, ethanol or tetrahydrofuran solvent.

Step B2: This step is the step of allowing the 2-acylamino-5-amino-4,6-dichloropyrimidine derivative 2 to react with a primary amine derivative to replace the chlorine atom at the 4-position by the amino derivative, to produce 4,5-diaminopyrimidine derivative 1.

This reaction is carried out preferably using an amine in excess, or in the presence of a tertiary amine such as triethylamine or diisopropyl ethylamine when the amine reacted is an alkyl amine, alkynyl amine and allyl amine, or in the presence of a catalytic amount of mineral acid, particularly hydrochloric acid when the amine reacted is an aryl amine or heteroaryl amine.

The solvent used is not particularly limited insofar as the reaction is not inhibited and the starting material is dissolved to a certain extent, and preferable examples include ethers such as tetrahydrofuran, dioxane, dimethoxyethane and diethylene glycol dimethyl ether; and halogenated hydrocarbons such as methylene chloride, chloroform and dichloroethane. The reaction temperature varies depending on the reactivity of the amine derivative used, preferably from room temperature to reflux temperature, more preferably reflux temperature.

Step B3: This step is the step of eliminating the acyl group i.e. a protective group for the amino group at the 2-position in the 2-acylaminopyrimidine derivative a, to produce 2-aminopyrimidine derivative 4.

The reaction is carried out by reacting with an aqueous mineral acid or alkaline solution in a solvent such as methanol, ethanol, dioxane or tetrahydrofuran. The reaction also proceeds at room temperature, but is carried out preferably under heating.

This step can be finished in the previous step B2 depending on the conditions for substitution with the amino derivative in the step B2, and in such case, this step is omitted. Step B4: This step is the step of dehydration condensation of the amino groups at the adjacent 4 and 5-position on the pyrimidine ring with an aldehyde to form an imidazole ring thereby producing a purine derivative 5.

The reaction is carried out by condensing the amino group at the 5-position with the aldehyde derivative to form a Schiff base, followed by ring closure by reaction with ferric chloride etc.

The solvent used is not particularly limited insofar as the reaction is not inhibited and the starting material is dissolved to a certain extent, and preferable examples include alcohols such as methanol and ethanol, ethers such as tetrahydrofuran, dioxane, dimethoxyethane, and diethylene glycol dimethyl ether, and dimethylformamide. The reaction is conducted at 0 to 100° C., preferably at room temperature. For production of the Schiff base, acetic acid is preferably added.

Step B5: This step is the step of converting the amino group in the 2-aminopurine derivativesby the Sandmeyer reaction into a halogen atom to produce 2,6-dihalogenopurine derivative 6.

The reaction is carried out by converting the amino group into a diazonium group by diazo reaction with a nitrite such as sodium nitrite, amyl nitrite or isoamyl nitrite and then converting the diazonium group into a halogen atom by cuprous halide. In the diazo reaction, an acid is not particularly necessary when a nitrite such as isoamyl nitrite is used, and the amino group can be converted into a halogen atom under heating by adding cuprous halide and methylene halide to a solvent such as dioxane or tetrahydrofuran. In the present invention, it is most preferable that cuprous iodide is used as cuprous halide and diiodomethane is used as methylene halide, to produce the 2-iodopurine derivative by conversion.

Step B6: This step is the step of allowing the chlorine atom at the 6-position in the 6-chloro-2-iodopurine derivative 6 to react with an amine derivative to produce 6-amino-2-iodopurine derivative 8.

When the amine derivative is gas or has a low boiling point, the reaction is carried out preferably in a sealed tube or in an autoclave.

The solvent used is not particularly limited insofar as the reaction is not inhibited and the starting material is dissolved to a certain extent, and preferable examples include alcohols such as methanol and ethanol; ethers such as tetrahydrofuran, dioxane, dimethoxyethane and diethylene glycol dimethyl ether; halogenated hydrocarbons such as methylene chloride, chloroform and dichloroethane; and dimethylformamide, 1-methyl pyrrolidinone etc.

The reaction temperature is preferably 0 to 150° C., more preferably 50 to 100° C.

Step B7: This step is the step of selectively subjecting the halogen atom at the 2-position in the 2-halogenopurine derivative 7 to coupling reaction with an ethynyl side chain, to produce 2-ethylnylene-6-halogenopurine derivative 8.

The reaction is conducted at room temperature or under heating in the presence of a catalytic amount of dichloro-bisphenyl phosphine palladium (II), cuprous iodide and a tertiary amine. The solvent used includes ethers such as tetrahydrofuran, dioxane, dimethoxyethane and diethylene glycol dimethyl ether, dimethylformamide, 1-methyl pyrrolidinone etc. The tertiary amine used includes triethylamine, diisopropylamine, DBU, dimethyl aniline etc. The reaction temperature is preferably 0 to 100° C., more preferably room temperature.

Production method C

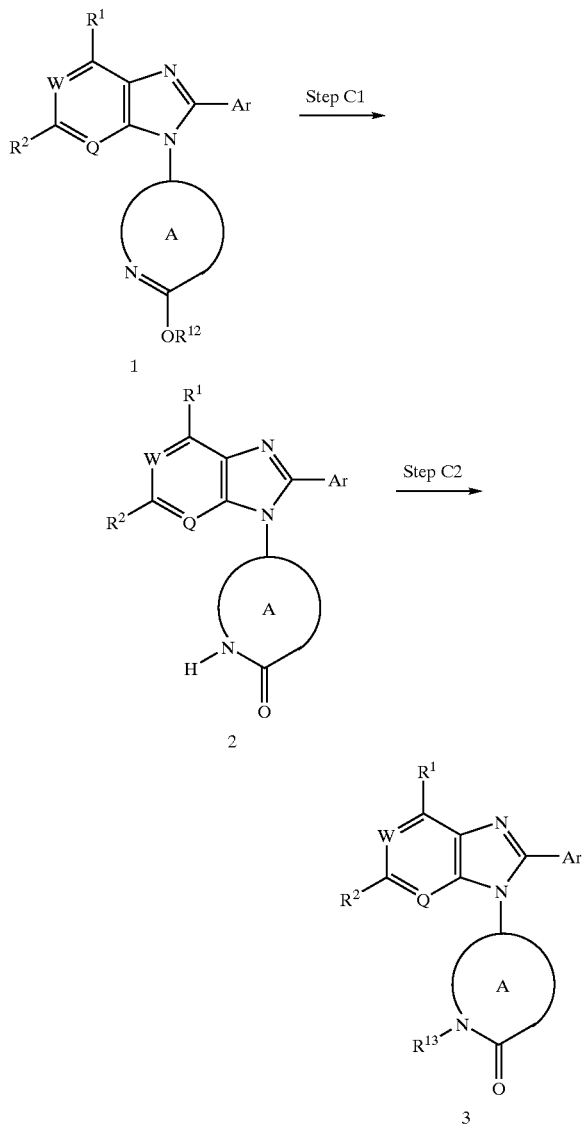

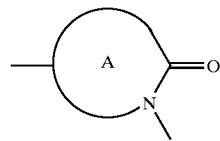

means a dihydroxopyridinyl or -pyrimidyl group, or dihydro- or tetrahydropyranydinyl group.

This production method C is a method of hydrolyzing the alkoxy group in the α-alkoxy N-containing heteroaryl compound in $R^3$ obtained in production method A or B, to produce an α-hydroxy N-containing heteroaryl derivative or to introduce a substituent group into the nitrogen atom in the ring.

Step C1: This step is the step of hydrolyzing the alkoxy group in the 9-α-alkoxy N-containing heteroaryl purine derivative 1, to produce 9-α-hydroxy N-containing heteroaryl purine derivative 2.

The reaction is carried out at room temperature to 100° C. in the presence of an aqueous solution of mineral acid such as hydrochloric acid, hydrobromic acid, sulfuric acid etc.

Step C2: This step is the step of introducing a substituent group into the nitrogen atom in the 9-α-hydroxy N-containing heteroaryl purine derivative 2 obtained above.

The reaction is carried out in the presence of a base by reaction with a halogenated alkyl compound, a halogenated fluoroalkyl compound, an alkoxycarbonyl alkyl halogen compound and various sulfonate compounds in a solvent.

The base includes sodium hydride, sodium hydroxide, potassium hydroxide, sodium bicarbonate, sodium carbonate, potassium carbonate or sodium alkoxide, and the solvent includes alcohols such as methanol and ethanol; ethers such as tetrahydrofuran, dioxane, dimethoxyethane and diethylene glycol dimethyl ether; halogenated hydrocarbons such as methylene chloride, chloroform and dichloroethane; and N,N-dimethylformamide, dimethylsulfoxide, 1-methyl pyrrolidinone etc. The reaction is carried out at a temperature of 0 to 100° C.

Production method D

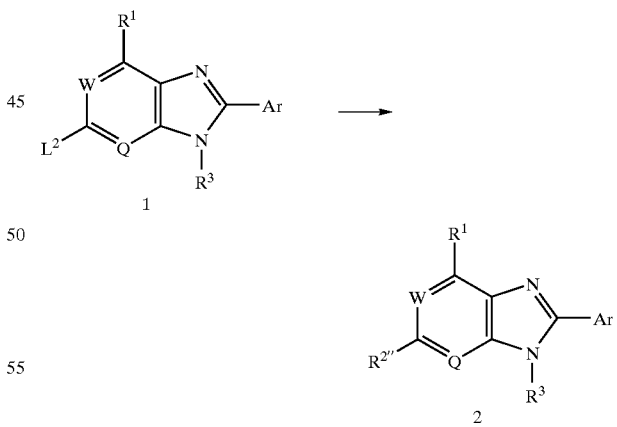

wherein $R^1$, $R^2$, Ar, Q and W have the same meanings as defined above; $R^{12}$ is a C1–C8 alkyl group; $R^{13}$ is a C1–C6 alkyl group which may be substituted with a halogen atom, hydroxyl or an optionally protected carboxyl group, an optionally substituted C3–C6 cycloalkyl-C1–C4 alkyl group or an optionally substituted C3–C6 cycloalkyl group; the formula:

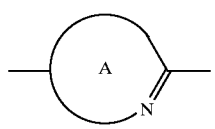

means a pyridinyl group, pyrimidyl group or pyrazinyl group; and the formula:

wherein $R^2$, means a C1–C8 alkoxy group; and $R^1$, $R^3$, $L^2$, Ar, Q and W have the same meanings as defined above.

The production method D is a method of converting the halogen atom at the 2-position in the compound 7 obtained in the production method B into a C1–C8 alkoxy group.

This reaction proceeds even if $L^2$ is any halogen atom, but bromine is preferable. By treatment with a hydrobromic acid solution, the iodine-atom derivative is easily converted into a bromine derivative.

The reaction is carried out by reacting with sodium or potassium alkoxide.

Production method E

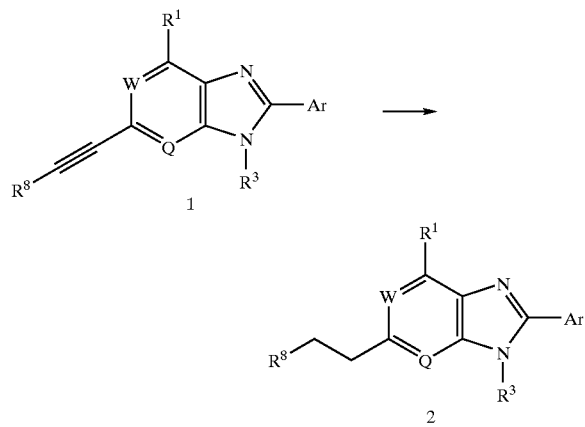

wherein $R^5$ means a C1–C4 alkyl group; and $R^1$, $R^3$, Ar, Q and W have the same meanings as defined above.

This production method is a method of subjecting the ethynylene group in the compound A obtained in the production method B to catalytic reduction, to give an alkyl derivative.

The catalytic reduction is conducted at normal pressure or under pressure, at room temperature or under heating, in the presence of a catalyst such as Raney Ni, Pd—C or $PtO_2$ in a hydrogen atmosphere. It is conducted preferably at normal pressure and at ordinary temperature, more preferably in the presence of Raney Ni as the catalyst at normal pressure and at ordinary temperature. The solvent used is not particularly limited insofar as it dissolves the starting material to a certain extent without causing catalytic poison, and preferable examples include methanol, ethanol, tetrahydrofuran, dioxane, acetic acid, dimethylformamide or a mixed solvent thereof.

Hereinafter, pharmacological experiments will be shown to explain the excellent effect of the purine compounds of the present invention.

Effect of Novel Purine Compounds

1) Adenosine A2a Receptor Binding Assay

A membrane specimen prepared by over-expression of adenosine A2a receptor was purchased from Receptor Biology Inc., and used to carry out adenosine A2a receptor binding assays. The purchased membrane specimen was suspended at a concentration of 22.2 µg/ml inan incubation buffer (20 mM HEPES, 10 mm $MgCl_2$ and 100 mM NaCl, pH 7.4). To 0.45 ml of this membrane specimen were added 0.25ml of tritium-labeled$^3$H-CGS21680 (500 nM; 30 Ci/mmol) and 0.025 ml of the test compound. The solution of the test compound was prepared by dissolving the compound at a concentration of 20 mM in DMSO and then successively diluting the solution 10-fold with the incubation buffer. The mixture was allowed to stand at 25° C. for 90 minutes, subjected to quick suction on a glass fiber filter (GF/B; manufactured by what man) and immediately washed twice with 5 ml of ice-cooled 50 mM Tris-HCl buffer. Thereafter, the glass fiber filter was transferred to a vial bottle, a scintillator was added thereto, and the radioactivity on the filter was measured by a liquid scintillation counter. The rate of inhibition of ($^3$H-CGS21680) binding to the A2a receptor by the test compound was calculated using the following equation, and from this rate of inhibition, $IC_{50}$ was calculated.

Rate of inhibition (%)=(1−{(Binding amount in the presence of drug−non-specific binding amount)/(Total binding amount−Non-specific binding amount)}×100

The total binding amount is $^3$H-CGS21680 binding radioactivity in the absence of the test compound. The non-specific binding amount is $^3$H-CGS21680 binding radioactivity in the presence of 100 AM of RPIA. The binding amount in the presence of drug is $^3$H-CGS21680 binding radioactivity in the presence of the test compound of various concentrations.

The inhibition constant (Ki value) was calculated from Cheng-Prusoff's expression.

The inhibition constants (Ki values) of the compounds in Examples 5 and 20 were 0.0032 and 0.0096, respectively.

2) Inhibitory Effect of Test Compound on NECA-stimulate cAMP Production in Adenosine A2a Receptor-expressing Cells Human adenosine A2b receptor cDNA was over-expressed in CHOK1 cells. The cells were uniformly placed on a 24-well plate at a density of $1.5 \times 10^5$ cells/well, incubated overnight and then used for the assays. Affinity of the test compound for the A2b receptor was evaluated by using, as an index, the rate of suppression of the amount of cAMP produced by stimulation of an adenosine agonist NECA (30 nM) in the presence of the test compound. Thus, the plate was washed twice with 2 ml/well of Krebs-Ringer-Bicarbonate buffer (KRB) (mM) (NaCl 118, KCl 4.8, $KH_2PO_4$ 1.2, $MgSO_4$ 1.2, $CaCl_2$ 3.4, HEPES 10, $NaHCO_3$ 25, pH 7.4) and then pre-incubated (0.5 ml/well) for 30 minutes. Thereafter, a mixed solution containing 600 µM Ro-20–1724 (phosphodiesterase inhibitor), 180 nM NECA, and a test compound at a concentration 6-times higher than in the reaction solution was added in an amount of 100 µm/well. After 15 minutes, the reaction was stopped by replacing the reaction solution by 0.1 N HCl (300 µl/well). Measurement of cAMP was carried out using an Amersham cAMP EIA Kit.

The rate of inhibition of NECA-stimulated cAMP production by the test compound was calculated using the following equation:

Rate of Inhibition (%)=[1−{(cAMP amount in the presence of NECA and test compound-Basal cAMP amount)/(cAMP amount stimulated only by NECA−Basal cAMP amount)}×100.

$IC_{50}$ was calculated from the rate of inhibition.

The $IC_{50}$ of the compound in Example 5 was 0.011 µM.

3) Inhibitory Action of Test Compound on NECA-stimulated Glucose Production in Primary Cultured Rat Hepatic Cells Hepatic cells were separated by a collagenase perfusion method from livers of male rats of Wistar strain and subjected to a primary culture in a William's Medium E containing 5% calf serum, $10^{-6}$ M insulin and $10^{-7}$ M dexamethasone. After 1 day, the hepatic cells were washed with a Krebs-Ringer Bicarbonate buffer (mM) (NaCl 118, KCl 4.8, $KH_2PO_4$ 1.2, $MgSO_4$ 1.2, $CaCl_2$ 3.4, HEPES 10, $NaHCO_3$ 25) pH 7.4 (KRB) containing 10 mM HEPES and 0.1% bovine serum albumin and KRB was added thereto, then incubated at 37° C. After 30 minutes, NECA (N-ethylcarboxamide adenosine) (final concentration: 0.1 PM) and a test compound were added thereto at the same time, the mixture was incubated for additional one hour, and the amount of glucose released into the incubation medium was measured.

IC$_{50}$ values (PM) for inhibition of NECA-stimulated glucose release by the compounds in Examples 5 and 20 were 0.0076 and 0.0084, respectively.

4) Artion of Test Compound on Hyperglycemia in Spontaneously Diabetic Mice (KK-A$^y$/Ta Jcl) (Single Administration)

Animals: Seven male KK-A$^y$/Ta Jcl mice for each group (purchased from Nippon Clair)

Preparation and Administration of Test Compound: A test compound in a dose as shown in Table 1 was suspended in 0.5% aqueous methyl cellulose solution and was orally administered in a volume of 10 ml/kg.

Collection of Blood Samples and Determination of Blood Sugar: Blood was collected from tail veins just before administration of the test compound and also 5 hours after the administration and blood sugar was determined.

Method: Tail vein of a mouse was injured by a razor without anesthetization to bleed slightly. The blood (15 µl) was collected and immediately mixed with 135 µl of 0.6 M perchloric acid. Glucose in the supernatant separated by centrifugation (at 1500 g for 10 minutes at 4° C. usingacooling centrifuge GS-6KR from Beckmann) was determined by Glucose CII Test Wako (Wako Pure Chemicals).

The results are shown in Table 1.

The results are shown in terms of "(% ratio of blood sugar 5 hours after the administration to the blood sugar before the administration)±(standard error)". The data were subjected to one-way layout analysis of variance and then subjected to multiple comparison of Dunnett type. Difference with p<0.05 was deemed significant.

TABLE 1

Action of test compound on hyperglycemia in spontaneously diabetic mice (KK-Ay/Ta Jcl)

| Test Compound | Dose (mg/kg) | $\dfrac{\text{Blood sugar level 5 hr after the administration}}{\text{Blood sugar level just before the administration}} \times 100$ (%) | Statistical significance |
|---|---|---|---|
| Control | | 72.5 ± 3.7 | |
| Example 5 | 10 | 47.3 ± 7.2 | ** |

(**; p < 0.01 vs. control)

As described above, the compound of the present invention had an adenosine A2 receptor antagonism and showed a clear effect on the pathological models of diabetes mellitus. In addition, the compound of the present invention also showed an improving action in investigation for impaired glucose tolerance in a glucose tolerance test, and was confirmed to act not only in the liver but also in the peripheral tissues.

EXAMPLES

Hereinafter, the processes for synthesizing the novel purine compounds of the present invention are exemplified, but as a matter of course, these Examples are shown for the purpose of facilitating the understanding of the present invention and not intended to limit the present invention.

Example 1

8-(3-Fluoruphenyl)-9-(6-methoxy-3-pyridyl)-9H-6-purineamine

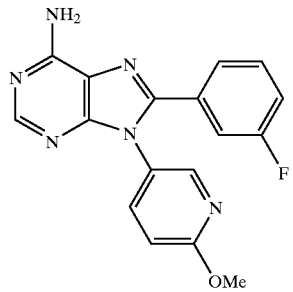

(1) Synthesis of N4-(6-methoxy-3-pyridyl)-6-chloro-4,5-pyrimidinediamine hydrocloride 5-Amino-2-methoxypyridine (8.7 g, 70.1 mmol) and conc. hydrochloric acid (1.5 ml) were added successively to a suspension of 5-amino-4,6-dichloropyrimidine (10.0 g, 45.2 mmol, produced by Tokyo Kasei Co., Ltd.) in water (100 ml)/ethanol (15 ml) at room temperature, and the mixture was heated under reflux for 3 hours. After cooling as it was, the resulting solid was collected by filtration, washed with water and air-dried at 50° C., to give the title compound (6.6 g, 72%) as a reddish brown solid.

$^1$H NMR (400 MHz, DMSO-d$_6$) δ ppm; 3.84 (3H, s), 6.84 (1H, d, J=9.6 Hz), 7.82 (1H, s), 7.99 (1H, dd, J=2.8, 9.6 Hz), 8.39 (1H, d, J=2.8 Hz), 8.78 (1H, s).

2) Synthesis of N1-[4-chloro-6-[(methoxy-3-pyridyl)amino]-5-pyrimidinyl]-3-fluorobenzamide 3-Fluorobenzoyl chloride (9.6 ml, 79.0 mmol) was added dropwise over 80 minutes in a nitrogen atmosphere at 0 to 5° C. to a pyridine (66 ml) suspension of the compound (6.6 g, 22.9 mmol) obtained in (1), and the mixture was stirred as such for 5 hours. The reaction solution was diluted with water and ethyl acetate. The organic layer was washed with 1 N hydrochloric acid (×1). After the 1N hydrochloric acid layer was extracted with ethyl acetate (×2), the combined organic layers were washed with a saturated aqueous sodium bicarbonate solution (×1), dried over anhydrous sodium sulfate and concentrated. The residue was suspended in diethyl ether, and the solid was collected by filtration and washed with diethyl ether, to give the title compound (6.5 g, 76%) as a colorless solid.

$^1$H NMR (400 MHz, DMSO-d$_6$) δ ppm 3.84 (3H, s), 6.84 (1H, d, J=8.8 Hz), 7.47–7.54 (1H, m), 7.59–7.66 (1H, m), 7.81–7.94 (3H, m), 8.26 (1H, d, J=2.4 Hz), 8.33 (1H, s), 9.38 (1H, s), 10.16 (1H, s).

(3) Syntheis of 6-chloro-8-(3-fluorophenyl)-9-(6-methoxy-3-pyridyl)-9H-purine

A suspension of the compound (435 mg, 1.16 mmol) obtained in (2) in phosphorus oxychloride (30 ml) was heated under reflux for 4.5 hours in a nitrogen atmosphere. After cooling as it was, the reaction solution was concentrated. The residue was diluted with ethyl acetate, washed with water (×3), a saturated aqueous sodium bicarbonate solution (×2) and brine (×1), dried over anhydrous sodium sulfate and concentrated. The residue was suspended in diethyl ether, and the solid was collected by filtration and washed with diethyl ether, to give the title compound (248 mg, 60%) as a colorless solid.

$^1$H NMR (400 MHz, DMSO-d$_6$) δ ppm 3.93 (3H, s), 7.05 (H, d, J=8.8 Hz), 7.38–7.48 (3H, m), 7.50–7.56 (1H, m), 7.90 (1H, dd, J=2.8,8.8 Hz), 8.35 (1H, d, J=2.8 Hz), 8.79 (1H, s).

(4) Synthesis of 8-(3-fluorophenyl)-9-(6-methoxy-3-pyridyl)-9H-6-purineamine

A suspension of the compound (1.0 g, 2.81 mmol) obtained in (3) in 1,2-dimethoxyethane (40 ml)/conc. ammonia water (20 ml) was stirred for 11 hours in an autoclave at 70° C. After cooling as it was, the reaction solution was diluted with a saturated ammonium chloride solution and ethyl acetate. The organic layer was washed with a'saturated aqueous ammonium chloride solution (×1), dried over anhydrous sodium sulfate and concentrated. The residue was suspended in diethyl ether, and the solid was collected by filtration and washed with diethyl ether, to give the title compound (928 mg, 98%) as a colorless solid.

$^1$H NMR (400 MHz, DMSO-d$_6$) δ ppm 3.91 (3H, s), 6.99 (1H, d, J=8.8 Hz), 7.26–7.33 (2H, m), 7.34–7.38 (1H, m), 7.43–7.49 (1H, m), 7.50 (2H, br s), 7.81 (1H, dd, J=2.8, 8.8 Hz), 8.14 (1H, s), 8.23 (1H, d, J=2.8 Hz).

Example 2

5-[6-Amino-8-(3-fluorophenyl)-9H-9-pirinyl]-1,2-dihydro-2-pyridinone

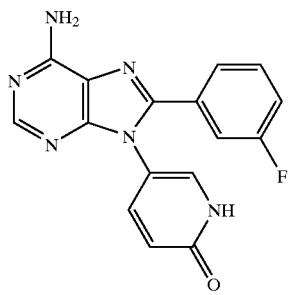

A suspension of 8-(3-fluorophenyl)-9-(6-methoxy-3-pyridyl)-9H-6-purineamine (890 mg, 2.65 mmol) obtained in Example 1 tin a conc. aqueous hydrobromic acid solution (12 ml) was stirred at 100° C. for 15 minutes. After cooling as it was, the reaction solution was neutralized with 5N aqueous sodium hydroxide solution, and the resulting solid was collected by filtration, washed with water, ethyl acetate and diethyl ether, to give the title compound (767 mg, 90%) as a colorless solid.

$^1$H NMR (400 MHz, DMSO-d$_5$) δ ppm; 6.42 (1H, d, J=9.2 Hz), 7.29–7.36 (1H, m), 7.40–7.56 (6H, m), 7.70 (1H, d, J=2.8 Hz), 8.15 (1H, s)

This compound (200 mg, 0.621 mmol) was dissolved in methanol-4N hydrochloric acid/ethyl acetate (10 drops) and concentrated. After the residue was crystallized from methanol/ethyl acetate/diethyl ether, the solid was collected by filtration and washed with diethyl ether, to give the hydrochloride (189 mg, 85%) as a colorless solid.

$^1$H NMR (400 MHz, DMSO-d$_6$) δ ppm; 6.47 (1H, d, J=9.6 Hz), 7.36–7.43 (1H, m), 7.44–7.60 (4H, m), 7.77 (1H, d, J=2.8 Hz), 8.47 (1H, s)

MS m/e (ESI):323 (MH$^+$).

Example 3

5-[8-(3-(Fluorophenyl)-6-(mthylamino)-9H-9-purinyl]-1,2-dihydro-2-pyridinone hydrochloride

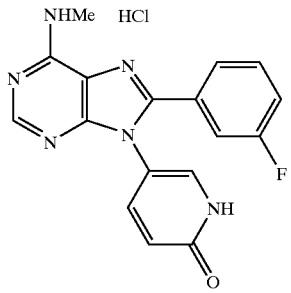

Monomethylamine was used in place of ammonia in (4) in Example 1, and synthesis was carried out in the same manner as in Example 2.

$^1$H NMR (400 MHz, DMSO-d$_6$) δ ppm; 3.10 (3H, br s), 6.47 (1H, d, J=9.2 Hz), 7.34–7.42 (1H, m), 7.42–7.60 (4H, m), 7.76 (1H, d, J=2.8 Hz), 8.41 (1H, s).

MS m/e (ESI): 337 (MH$^+$)

Example 4

5-[6-(Dimethylamino)-8-(3-fluorophenyl)-9H-9-purinyl]-1,2-dihydro-2-pyridinone hydrochloride

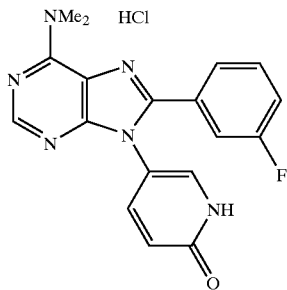

Dimethylamine was used in place of ammonia in (4) in Example 1, and synthesis was carried out in the same manner as in Example 2.

$^1$H NMR (400 MHz, DMSO-d$_6$) δ ppm; 3.56 (6H, br s), 6.46 (1H, d, J=9.2 Hz), 7.32–7.39 (1H, m), 7.42–7.57 (4H, m), 7.75 (1H, d, J=2.8 Hz), 8.32 (1H, s).

MS m/e (ESI): 351 (MH$^+$).

Example 5

5-[6-Amino-8-(3-fluorophenyl)-9H-9-purinyl]-1-methyl-1,2-dihydro-2-pyridinone hdrochloride

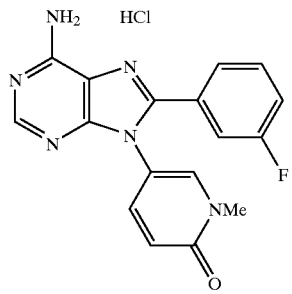

N,N-Dimethylformamide dimethylacetal (0.5 ml, 3.76 mmol) was added to a suspension of 5-[6-amino-8-(3-fluorophenyl)-9H-9-purinyl]-1,2-dihydro-2-pyridinone (1.0 g, 3.10 mmol) in Example 2 in N,N-dimethylformamide (10 ml) and stirred in a nitrogen atmosphere at room temperature. After 1 hour, N,N-dimethylformamide dimethyl acetal (0.5 ml, 3.76 mmol) was further added thereto and stirred for additionall 5 hours. The reaction solution was ice-cooled, and 60 to 70% sodium hydride (136 mg, 3.40 mmol) was added thereto at 0 to 6° C. and stirred. After 30 minutes, iodomethane (0.29 ml, 4.66 mmol) was added dropwise thereto and stirred. After 20 minutes, conc. ammonia water (10 ml) was added thereto and stirred at room temperature. After 16 hours, the reaction solution was diluted with a saturated aqueous ammonium chloride solution and ethyl acetate. The aqueous layer was extracted with ethyl acetate (×4), and the combined organic layers were washed with 1 N aqueous sodium hydroxide solution (×1) and a saturated aqueous ammonium chloride solution (×1), dried over anhydrous sodium sulfate and concentrated. The residue was suspended in ethyl acetate, and the solid was collected by filtration and washed with ethyl acetate, to give the title compound in free form (703 mg). This free compound was dissolved in methanol-4N hydrochloric acid/ethyl acetate (1.5 ml) and concentrated. The residue was crystallized from methanol/ethyl acetate/diethyl ether, and the solid was collected by filtration and washed with diethyl ether, to give the title compound (697 mg, 60%) as a colorless solid.

$^1$H NMR (400 MHz, DMSO-d$_6$) δ ppm; 3.46. (3H, s), 6.52 (1H, d, J=9.2 Hz), 7.36–7.43 (1H, m), 7.44–7.60 (4H, m), 8.15 (1H, d, J=2.8 Hz), 8.42 (1H, s)

MS m/e (ESI): 337 (MH$^+$).

Example 6

5-[6-(Dimethylamino)-8-(3-fluorophenyl)-9H-9-purinyl]-1-methyl-1,2-dihydro-2-pyridinone hydrochloride

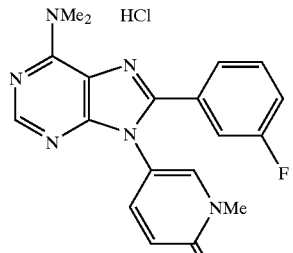

60 to 70% sodium hydride (28 mg, 0.700 mmol) was added to a suspension of 5-[6-(dimethylamino)-8-(3-fluorophenyl)-9H-9-purinyl]-1,2-dihydro-2-pyridinonehydrochloride (130 mg, 0.336 mmol) in Example 4 in N,N-dimethylformamide (3 ml), and the mixture was stirred in a nitrogen atmosphere at 0 to 6° C. After 1 hour, iodomethane (23 µl, 0.369 mmol) was added thereto and stirred. After 30 minutes, 60 to 70% sodium hydride (17 mg, 0.425 mmol) was added thereto, and 30 minutes thereafter, additional iodomethane (23 µl, 0.369 mmol) was added thereto and stirred. After 30 minutes, the reaction solution was diluted with a saturated aqueous ammonium chloride solution and ethyl acetate. The organic layer was washed with a saturated aqueous ammonium chloride solution (×1) and then extracted with 1N hydrochloric acid (×1). The 1N hydrochloric acid layer was adjusted to pH 9–10 with 1N aqueous sodium hydroxide solution and extracted with ethyl acetate (×1). The organic layer was dried over anhydrous sodium sulfate and concentrated. The residue was dissolved in methanol-4N hydrochloric acid/ethyl acetate (1.5 ml) and concentrated. The residue was crystallized from methanol/diethyl ether, and then the solid was collected by filtration and washed with diethyl ether, to give the title compound (90 mg, 67%) as a colorless solid.

$^1$H NMR (400 MHz, DMSO-d$_6$) δ ppm; 3.46 (3H, s), 3.56 (6H, s), 6.51 (1H, d, J=9.6 Hz), 7.33–7.39 (1H, m), 7.46–7.56 (4H, m), 8.14 (1H, d, J=2.4 Hz), 8.31 (1H, s).

MS m/e (ESI): 365 (MH$^+$).

Example 7

8-(3-Fluoronphenyl)-2-iodo-9-(6-methoxy-3-pyridyl)-9H-6-purineamine

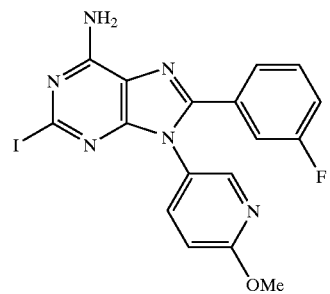

(1) Synthesis of N1-(5-amino-4,6-dichloro-2-pyrimidinyl)acetamide

N1-(4,6-Dichloro-5-nitro-2-pyrimidinyl)acetamide (100 g, 0.40 mol) and Raney nickel (100 g, wet) were suspended in methanol (1.5 L) and stirred vigorously for 5 hours in a hydrogen atmosphere, at ordinary temperature and at normal pressure. After the nickel was filtered off, the filtrate was concentrated. The residue was crystallized from methanol/ethyl acetate, and the crystals were collected by filtration and washed with ethyl acetate, to give the title compound (44.6 g, 51%) as a brown solid.

¹H-NMR(400 MHz,DMSO-d₆) δ ppm 2.05 (3H, s), 5.78 (2H, s), 10.53 (1H, s).

(2) N4-(6-Methoxy-3-pyridyl)-6-chloro-2,4,5-pyrimidine triamine

5-Amino-2-methoxypyridine (12.4 g, 99.9 mmol) and conc. hydrochloric acid (3.0 ml) were added successively to a suspension of the compound (10.0 g, 45.2 mmol) obtained in (1) in water (200 ml)/ethanol (30 ml), and the mixture was heated under reflux for 3.5 hours. After cooling asit was, the reaction solution was neutralized with a saturated aqueous sodium bicarbonate solution, and the resulting crystals were collected by filtration, washed with water and air-dried at 50° C., to give the title compound (9.25 g, 66%) as a reddish brown solid.

¹H NMR (400 MHz, DMSO-d₆) δ ppm; 3.83 (3H, s), 4.16 (2H, br s), 5.89 (2H, brs), 6.78 (1H, d, J=9.0 Hz), 8.00 (1H, dd, J=2.6, 9.0 Hz) 8.36 (1H, s), 8.56 (1H, d, J=2.6 Hz).

(3) 6-Chloro-8-(3-fluorophenyl)-9-(6-methoxy-3-pyridyl)-9H-2-purineamine

3-Fluorobenzaldehyde (3.0 g, 24.2 mmol) and acetic acid (1. 8 ml) were added successively to a suspension of the compound (6.0 g, 19.4 mmol) obtained in (2) in methanol (60 ml), and the mixture was stirred at room temperature for 15 hours. The reaction solution was concentrated and then subjected twice to azeotropic distillation with toluene. The resulting azeotropically distillated residue was suspended in ethanol (60 ml), and a solution of anhydrous iron (III) chloride in ethanol (30 ml) was added thereto at room temperature and heated under reflux for 3.5 hours. After cooling as it was, the reaction solutionwas concentrated. The residuewas suspended ina small amount of methanol, and the solid was collected by filtration and washed with ethanol, to give the title compound (5.2 g, 72%) as a brown solid.

¹H NMR (400 MHz, DMSO-d₆) δ ppm 3.91 (3H, s), 7.00 (1H, d, J=8.8 Hz) 7.09 (2H, br s), 7.27–7.35 (3H, m), 7.42–7.48 (1H, m), 7.83 (1H, dd, J=2.6,8.8 Hz), 8.30 (1H, d, J=2.6 Hz).

(4) 6-Chloro-8-(3-fluorophenyl)-2-iodo-9-methoxy)-3-pyridyl)-9H-2-purine

Copper (I) iodide (2.1 g, 11.0 mmol), diiodomethane (4.4 ml, 54.5 mmol) and isoamyl nitrite (4.4 ml, 32.8 mmol) were added successively to a solution of the compound obtained in (3) tetrahydrofuran (80 ml) at room temperature, and the mixture was stirred at 70° C. for 2 hours. After cooling as it was, the insoluble matters were filtered off. The filtrate was diluted with ethyl acetate and IN hydrochloric acid, and the organic layer was washed with conc. ammonia water/saturated aqueous ammonium chloride solution (1:1) (×1) and a saturated aqueous ammonium chloride solution (×1), dried over anhydrous sodium sulfate and concentrated. The residue was suspended in diethyl ether, and the solid was collected by filtration and washed with diethyl ether, to give the title compound (2.98 g, 57%) as a reddish brown solid.

¹H NMR (400 MHz, DMSO-d₆) δ ppm 3.94 (3H, s), 7.06 (1H, d, J=8.8 Hz), 7.34–7.44 (3H, m), 7.48–7.55 (1H, m), 7.88 (1H, dd, J=2.8,8.8 Hz) 8.34 (1H, d, J=2.8 Hz).

(5) 8-(3-Fluorophenyl)-2-iodo-9-(6-methoxy-3-pyridyl)-9H-6-purineamine

A suspension of the compound (2.98 g, 61.9 mmol) obtained in (4) in 1,2-dimethoxyethane (60 ml)/conc. ammonia water (30 ml) was stirred for 6 hours in an autoclave at 70° C. After cooling as it was, the reaction solution was concentrated. The residue was suspended in methanol, and the solid was collected by filtration and washed with methanol, to give the title compound (2.69 g, 94%) as a colorless solid.

¹H NMR (400 MHz, DMSO-d₆) δ ppm 3.92 (3H, s), 7.00 (1H, d, J=9.0 Hz) 7.24–7.35 (3H, m), 7.42–7 49 (1H, m), 7.81 (1H, dd, J=2.6,9.0 Hz) 7.92 (2H! br s), 8.25 (1H, d, J=2.6 Hz).

Example 8

5-[6-Amino-2-bromo-8-(3-fluorophenyl)-9H-9-purinyl]-1, 2-pyridinone

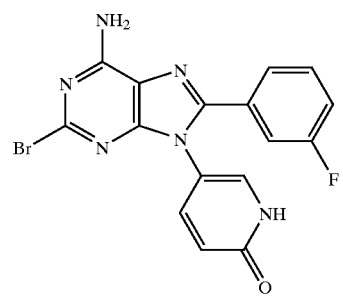

A suspension of the compound (100 mg, 0.216 mmol) in Example 7 in a conc. aqueous hydrobromic acid solution (2 ml) was stirred at 100° C. for 15 minutes. After cooling as it was, the reaction solution was diluted with water, and the solid was collected by filtration and washed with water and ether, to give the title compound (71 mg, 79%) as a colorless solid.

¹H NMR(40 DMHz,DMSO-d₆) δ ppm 6.45 (1H, d, J=9.6 Hz), 7.30–7.38 (1H, m), 7.38–7.46 (2H, m), 7.46–7.66 (2H, m), 7.73 (1H, d, J=2.8 Hz), 8.01 (2H,br s).

Example 9

5–16-Amino-8-(3-fluorophenyl)-2-propoxy-9H-9purinyll-1–2dihydro-2-pyridinone hydrochride

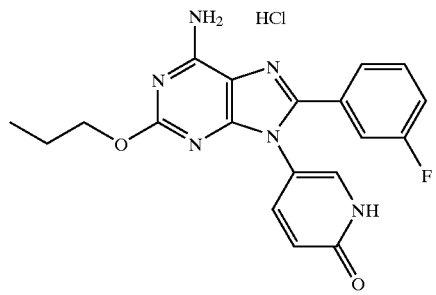

The compound (82 mg, 0.204 mmol) in Example 8 was added to a solution of sodium (30 mg, 1.30 mmol) in 1-propanol (3 ml) and heated under reflux for 4 hours. After cooling as it was, the reaction solution was diluted with a saturated aqueous ammonium chloride solution and ethyl acetate. The organic layer was washed with a saturated aqueous ammonium chloride solution (×1), dried over anhydrous sodium sulfate and concentrated. The residue was dissolved inmethanol-5N hydrochloric acid (3 drops) and

Example 10

8-(3-Fluorophenyl)-9-(6-methoxy-3-pyridyl)-2-(1-pentynyl)-9H-6-purineamine

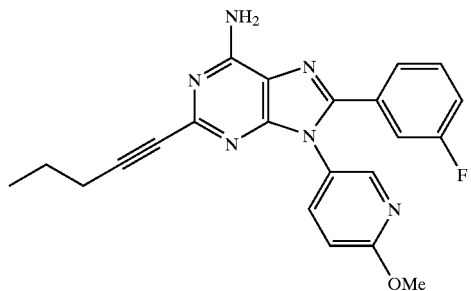

Triethylamine (0.2 ml, 1.43 mmol) was added dropwise to a suspension of the compound (200 mg, 0.433 mmol) in Example 7, copper (I) iodide (8 mg, 42.0 μmol), dichlorobis(triphenylphosphine) palladium (II) (30 mg, 42.7 μmol) and 1-pentyne (60 mg, 0.880 mmol) in N,N-dimethylformamide (3 ml) in a nitrogen atmosphere at room temperature, and the mixture was stirred for 18 hours. The reaction solution was diluted with a saturated aqueous ammonium chloride solution and ethyl acetate. The organic layer was washed with conc. ammonia water/saturated aqueous ammonium chloride solution (1:1) (×1) and a saturated aqueous ammonium chloride solution (×1), dried over anhydrous sodium sulfate and concentrated. The residue was suspended in diethyl ether, and the solid was collected by filtration and washed with diethyl ether, to give the title compound (148 mg, 85%) as a pale brown solid.

$^1$H NMR (400 MHz,DMSO-d$_6$) δ ppm 0.97 (3H, t, J=7.2 Hz), 1. 53 (2H, sex, J=7.2 Hz), 2.35 (2H, t, J=7.2 Hz), 3.92 (3H, s), 7.01 (1H, d, J=8.8 Hz), 7.26–7.38 (3H, m), 7.42–7.49 (1H, m), 7.61 (2H,br s), 7.80 (1H, dd, J=2.8,8.8 Hz), 8.24 (1H, d, J=2.8 Hz).

concentrated. The residue was crystallized from methanol/ether, and the solid was collected by filtration and washed with ether, to give the title compound (71 mg, 67%) as a colorless solid.

$^1$H NMR (400 MHz, DMSO-d$_6$) δ ppm; 6.45 (1H, d, J=9.6 Hz), 7.30–7.38 (1H, m), 7.38–7.46 (2H, m), 7.46–7.66 (2H, m), 7.73 (1H, d, J=2.8 Hz), 8.01 (2H, br s).

MS m/e (ESI):381 (MH$^+$)

Example 11

8-(3-Fluorophenlyl)-9-(6-methoxy-3-pyridyl)-2-pentlyl-9H-6-purineamine

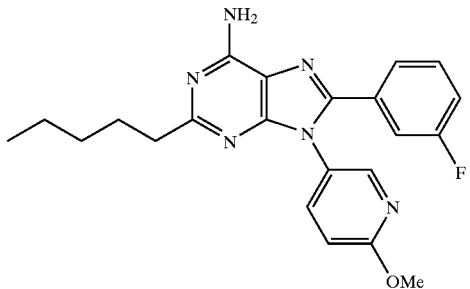

After 10% hydrous palladium-carbon (25 mg) was added to a solution of the compound (127 mg, 0.316 mmol) in Example 10 in methanol (20 ml) and stirred vigorously for 4.5 hours in a hydrogen atmosphere, at ordinary temperature and at normal pressure. After the palladium-carbon was filtered off, the filtrate was concentrated, to give the title compound (122 mg, 95%) as a brown solid.

$^1$H NMR (400 MHZ, CDC13) δ ppm 0.88 (3H, t, J=7.2 Hz), 1.27–1.40 (4H, m), 1.70–1.83 (2H, m), 2.75 (2H, t, J=7.6 Hz), 3.98 (3H,S) 5.87 (2H,br s), 6.85 (6 H , d, J=8.3 Hz), 7.06–7.12 (1H, m), 7.19–7.34 (3H,), 7.53 (1H, dd, J=2.8, 8.8 Hz), 8.13 (1H, d, J=2.8 Hz)

Example 12

5-[6-Amino-8-(3-fluorophenyl)-9-(6-methhoxy-3-pyridyl)-2-pentyl-9H-9-purinyl]-1,2-dihydro-2-peridinone hydrochloride

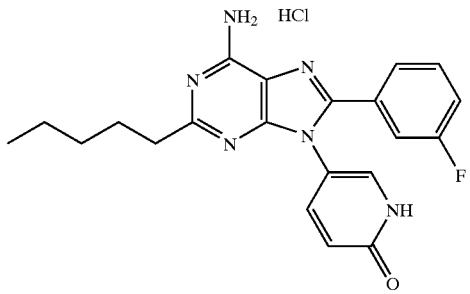

8-(3-Fluorophenyl)-9-(6-methoxy-3-pyridyl)-2-pentyl-9H-9H-6-purineamine obtained in Example 11 was treated in the same manner as in Example 2 and converted into the hydrochloride, to give the title compound.

$^1$H NMR (400 MHZ-DMSO-d$_6$) δ ppm 0.86 (3H, t, J=7.2 Hz), 1.25–1.37 (4H, m), 1.65–1.77 (2H, m), 2.80 (2H,t, J=7.6 Hz), 6. 47 (1H, d, J=9.6 Hz), 7.36–7.37 (3H, m), 7.51 (.H, dd, J=2. 8,9.6 Hz) 7.53–7.60 (1H,M), 7.76 (1H, d, J=2.8,9.6 Hz).

MS m/e (ESI):393 MH$^+$).

Example 13

N-[8-(3-Fluorophenyl)-9-(2-propinyl)-9H-6-purinyl]-N, N-dimethylamine hydrochloride

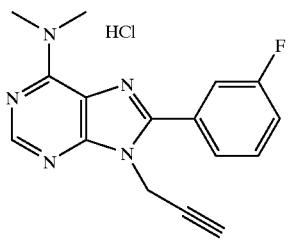

1) Synthesis of N4-(2-propenyl)-6-chloro-4,5-pyrimidine diamine

A solution of 8 g 5-amino-4,6-dichloropyrimidine, 5 ml propargylamine and 42 ml diisopropyl ethyl amine in 100 ml butanol was stirred for 6 hours and 10 minutes in a nitrogen atmosphere at 140° C. Ethyl acetate and H²O were added to the reaction mixture, and this mixture was filtered through Celite, and the residue was extracted with ethyl acetate. The organic layer was dried over magnesium sulfate, and the residue was purified by silica gel column chromatography (eluted with ethyl acetate:n-hexane=1:1), and the objective fractions were concentrated. The residue was crystallized from diethyl ether, to give the title compound (4.8 g, 54%) as pale brown crystals.

$^1$H NMR (400 MHz, CDCl$^3$) δ ppm; 2.26 (1H, t, J=2.4 Hz), 3.40 (2H, br s), 4.28 (2H, d, J=2.4 Hz), 4.98 (1H, br s), 8.10 (1H, s)

2) 6-Chloro-8-(3-fluorophenyl)-9-(2-propinyl)-9-purine

N4-(2-Propenyl)-6-chloro-4,5-pyrimidine diamine obtained in 1) and 3-fluorobenzoyl chloride were reacted in the same manner as in 2) in Example 1, to give the title compound.

3) N-[8-(3-Fluorophenyl)-9-(2-prpinyl)-9H-6-purinyl]-N,N-dimethylamine hydrochloride A solution of 150 mg 6-chloro-8-(3-fluorophenyl)-9-(2-propinyl)-9H-purine and 5 ml of 40% aqueous dimethylamine in 5 ml ethanol was stirred for 14 hours in an autoclave at 70° C. H$_2$O was added to the reaction mixture, and the resulting suspension was filtered and washed with diethyl ether, to give N-[8-(3-fluorophenyl)-9-(2-propinyl)-9H-6-purinyll-N,N-dimethylamine. 1 ml of 5 M aqueous hydrochloric acid was added to a suspension of this compound in methanol, and the solvent was evaporated from this methanol solution. The resulting suspension was filtered and washed with diethyl ether, to give the title compound (97 mg, 64%).

$^1$H NMR (400 MHz, DMSO-d$_6$) δ ppm 3.47 (1H, t, J=2.4 Hz), 3.56 (6H,brs), 5.16 (2H, d, J=2.4 Hz) 7.45–7.47 (1H, m), 7.63–7.69 (1H, m), 7.72–7.78 (2H, m), 8.39 (1H, s).

MS m/e (ESI):296 (MH$^+$)

The compounds in Examples 14 to 16 were obtained in a similar manner.

Example 14

8-(3-Fluorophenyl)-9-(2-propinyl)-6-tetrahydro-1H-1-pyroryl-9H-purine hydrochorinde

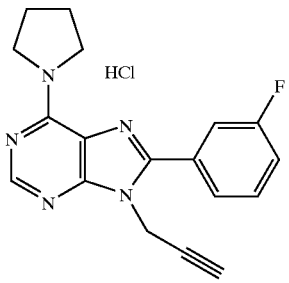

H NMR (400 MHz,DMSO-d$_6$) δ ppm 1.93–2.10 (4H, m), 3.51 (1H, t, J=2.4 Hz). 3.66–3.81 (2H, m), 4.15–4.30 (2H, m), 5.20 (2H, d, J=2.4 Hz), 7.42–7.49 (1H, m), 7.63–7.69 (1H, m) 7.73–7.78 (2H, m), 8.44 (1H, s).

MS m/e (ESI):322 (MH$^+$).

Example 15

N-Cyclopropyl-N-[(3-fluorophenyl)-9-(2-propinyl)-9H-6-purinyl]amine

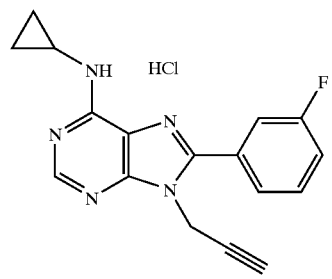

$^1$H NMR (400 MHz, DMSO-d$_6$) δ ppm; 0.74–0.89 (2H, m), 0.89–0.94 (2H, m), 2.80–2.97 (1H, m), 3.46 (1H, t, J=2.0 Hz), 5.15 (2H, d, J=2.0 Hz), 7.46–7.50 (1H, m), 7.65–7.76 (3H, m), 8.54 (1H, s)

MS m/e (ESI):308 (MH$^+$).

Example 16

8-(3-Fluorohpeyl)-9-(2-propinyl)-9H-6-purineamine hydrochloride

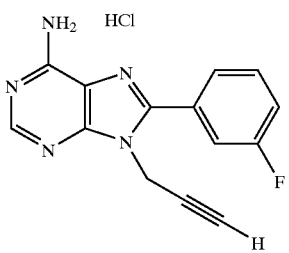

$^1$H NMR (400 MHz, DMSO-d$_6$) δ ppm; 3.52 (1H, t, J=2.4), 5.16 (2H, J=2.4), 7.47–7.51 (1H, m), 7.66–7.77 (3H, m), 8.45 (1H, s).

MS m/e (ESI): 267.92 (MH+)

Example 17

9-Allyl-8-(3-fluorophenyl)-9-6-purineamine hydrochloride

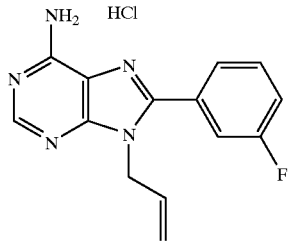

The title compound was obtained in the same treatment as in Example 13 except that allyl amine was used in place of propargylamine.

$^1$H NMR (400 MHz, DMSO-d$_6$) δ ppm; 4.83 (1H, dd, J=0.91, 17.2), 4.95 (2H, m), 5.16 (1H, dd, J=0.91, 10.4), 7.45–7.47 (1H, m) 7.61–7.65 (3H, m), 8.48 (1H, s).

MS m/e (ESI):269.91 (MH$^+$)

Example 18

9-(2-Butynyl)-8-(3-fluorophenyl)-9H-6-purineamine hydrochloride

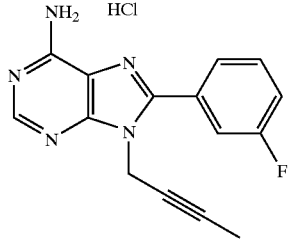

1) 2-Butynyl Methanesulfonate 305 ml methanesulfonyl chloride was added dropwise to a solution of 138 g 2-butyn-1-ol and 683 ml triethylamine in 2.7 L methylene chloride under ice-cooling, and the mixture was stirred at 0° C. for 1 hour and 40 minutes. Ice was added to the reaction solution under ice-cooling, and this mixture was extracted with methylene chloride. The organic layer was successively washed with 1M aqueous hydrochloric acid, a saturated aqueous sodium bicarbonate solution and brine, and the organic layer was dried over magnesium sulfate. This organic layer was filtered and then the solvent was evaporated, to give a dark brown oil (280 g, 96%).

2) 1-Bromo-2-butyne 493 g lithium bromide was added dropwise to a solution of 280 g 2-butynyl methanesulfonate in 3.5 L dimethylformamide under ice-cooling, and the mixture was stirred for 2 hours in a nitrogen atmosphere at room temperature. Ice was added to the reaction mixture under ice-cooling, and this mixture was extracted with diethyl ether. The aqueous layer was extracted again with diethyl ether, and the whole organic layer was washed with water and then with brine, and the organic layer was dried over magnesium sulfate. This organic layer was filtered and then the solvent was evaporated, to give a dark brown oil (137 g, 54%)

3) N,N-Diformyl-2-butyne 117 g diformylimide sodium salt was added dropwise to a solution of 137 g 1-bromo-2-butyne in 1.3 L dimethylformamide under ice-cooling, and stirred for 3 hours and 50 minutes in a nitrogen atmosphere at room temperature. Tetrahydrofuran was added to the reaction mixture at room temperature, and the resulting suspension was filtered to give crystals. The resulting crystals were washed with tetrahydrofuran. The whole filtrate was added to a mixture of ethyl acetate and water, followed by extracting. The aqueous layer was extracted again with ethyl acetate, and the whole organic layer was washed with water and brine, and dried over magnesium sulfate. This organic layer was filtered, and the solvent was evaporated, to give a dark brown oil (77 g, 60%)

4) 2-Butine-1-amine hydrochloride 77 g N,N-diformyl-2-butine and 390 ml of 10% hydrochloric acid-methanol solution were stirred at 65 ° C. for 15 minutes in a nitrogen atmosphere. The reaction mixture was cooled, diethyl ether was added thereto, the resulting suspension was filtered and washed with diethyl ether, to give 2-butyn-1-amine hydrochloride (26 g, 40%)

$^1$H NMR (400 MHz, DMSO-d$_6$) δ ppm; 1.85 (3H, t, J=2.6 Hz), 3.63 (2H, q, 5 Hz), 8.47 (2H, bs).

5) N1-[4-Chloro-6-(2-butynylamino)-5-pyrimidinyl]-3-fluorobenzamide 5.9 ml of 3-fluorobenzoyl chloride was added dropwise to a solution of 48.8 mmol N4-(2-butynyl)-6-chloro-4,5-pyrimidine diamine in 50 ml pyridine, and this mixture was stirred for 15 minutes in a nitrogen atmosphere at 0° C. and further stirred for 30 minutes at room temperature. Water was added to the reaction solution at room temperature, and the resulting mixture was extracted with ethyl acetate. The organic layer was successively washed with water and brine, and the whole aqueous layer was extracted again with ethyl acetate. The whole organic layer was dried over magnesium sulfate and filtered, followed by evaporating the solvent to give crystals. The resulting crystals were washed with diethyl ether and collected by filtration, to give 5.64 g of N1-[4-chloro-6-(2-butynylamino)-5-pyrimidinyll-3-fluorobenzamide as white crystals.

$^1$H NMR (400 MHz, DMSO-d$_6$)δppm; 3.07 (1H, t, J=2.4 Hz), 4.12–4.14 (2H, m), 7.45–7.50 (1H, m), 7.58–7.63 (1H, m), 7.80–7.87 (2H, m), 8.05–8.08 (1H, m), 8.34 (1H, 8).

Then, a suspension of 5.64 g N1-[4-chloro-6-(2-propinylamino)-5-pyrimidinyl]-3-fluorobenzamide in 56 ml phosphorus oxychloride was stirred at 120° C. for 7 hours. The phosphorus oxychloride was evaporated from the reaction solution, and ice-water was added to the residue. This mixture was neutralized with sodium bicarbonate, and the resulting mixture was extracted with ethyl acetate. The aqueous layer was filtered through Celite, and the filtrate was extracted again with ethyl acetate, and the whole organic layer was dried over magnesium sulfate. The residue was purified by silica gel short-column chromatography, and the resulting crystals were washed with diethyl ether and collected by filtration, to give 6-chloro-8-(3-fluorophenyl)-9-(2-butynyl)-9H-purine (2.08 g, 35%) as pale brown crystals.

$^1$H NMR (400 MHz, DMSO-d$_6$)δppm 3.56 (1H, t, J=2.6 Hz), 3.40 (2H, d, J=2.4 Hz), 7.53–7.58 (1H, m), 7.71–7.76 (1H, m), 7.82-7.87 (1H, m), 8.89 (1H, s).

MS m/e (ESI): 287 (MH$^+$).

The product was converted in a usual manner into its hydrochloride, to give 9-(2-butynyl)-8-(3-fluorophenyl)-9H-6-purineamine hydrochloride.

$^1$H NMR (400 MHz,DMSO-d$^6$) δ ppm 1.75 (3H,br s), 5.05 (2H, d, J=2.0 Hz) 7.41–7.50 (1H, m), 7.65–7.91 (5H, m), 8.29 (1H, s).

MS m/e (ESI): 282 (MH$^+$)

Example 19

5-[6-Amino-8-(3-fluorophenyl)-2-(3-hydroxy-3-methyl 1-butynyl)-9H-9-purinyl]-1,2-dihydro-2-pyridnone hydrochloride

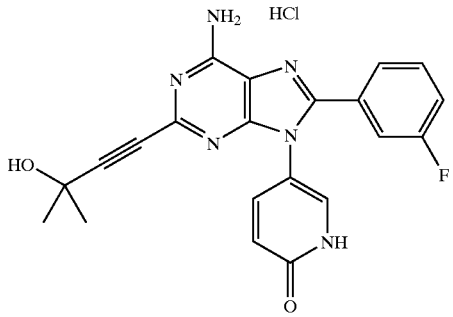

1) 2-(Allylxy)-5-nitropyridine 60 to 70% sodium hydride (3.0 g, 75.0 mmol) was added to a solution of allyl alcohol (8.6 g, 148 mmol) in N,N-dimethylformamide (100 ml) under ice-cooling in a nitrogen atmosphere and stirred. After foaming was confirmed to disappear, 2-bromo-5-nitropyridine (10.3 g, 50.7 mmol) was added thereto and stirred as such for 20 minutes. The reaction solution was diluted with a saturated aqueous ammonium chloride solution and extracted with ethyl acetate (×1). The organic layer was washed with a saturated aqueous ammonium chloride solution (×3), dried over anhydrous sodium sulfate and concentrated, to give the title compound 24 in crude form (9.9 g, quant.) as a dark brown solid.

$^1$H NMR (400 MHz,DMSO-d$^6$) δ ppm 4.96 (2H, dt, J=1.6, 5.6 Hz), 5.29 (1H, dq, J=1.6, 10.4 Hz), 5.41 (1H, dq, J=1.6, 17.2 Hz), 6.03–6.14 (1H, m), 7.08 (1H, d, J=9.2 Hz), 8.50 (1H, dd, J=2.8,9.2 Hz) 9.08 (1H, d, J=2.8 Hz).

2) 6-(Allyloxy)-3-pyridineamine

Zinc powder (20 g, 306 mmol) was added little by little to a suspension of the crude compound (9.9 g, 50.7 mmol) in 1) in ethanol (200 ml)/water (100 ml)/acetic acid (10 ml), and stirred for 30 minutes. After the insoluble matters were filtered off, the filtrate was diluted with ethyl acetate and a saturated aqueous ammonium chloride solution. The organic layer was washed with a saturated aqueous ammonium chloride solution (×1), 1 N aqueous sodium hydroxide (×1) and a saturated aqueous ammonium chloride solution (×1), dried over anhydrous sodium sulfate and concentrated, to give the title compound 25 in crude form (6.7 g, 88%) as a black brown liquid.

$^1$H NMR (400 MHz, DMSO-d$^6$) δ ppm: 4.64 (2H, dt, J=1.6, 5.2 Hz), 4.75 (2H, br s), 5.18 (1H, dq, J=1.6, 10.4 Hz), 5.32 (1H, dq, J=1.6, 17.2 Hz), 5.97–6.08 (1H, m), 6.57 (1H, d, J=8.8 Hz), 7.01 (1H, dd, J=2.8, 8.8 Hz), 7.48 (1H, d, J=2.8 Hz).

3) 5-[6-Amino-8-(3-fluorophenyl)-2-(3-hydroxy-3-methyl-1-butynyl)-9H-9-purinyl]-1,2-dihydro-2-pyridinone hydrochloride 10% hydrous palladium-carbon (10 mg) and p-toluenesulfonic acid monohydrate (12 mg, 0.063 mmol) were added to a solution of 4-[9-(6-allyloxypyridine-3-yl) amino-8-(3-fluorophenyl)-9H-purin-2-yl]-2-methylbut-3-yn-2-ol synthesized in the same methods as in Examples 7 and 10 (90 mg, 0.202 mmol) in ethanol (10 ml)-water (2 ml), and the mixture was heated under reflux. After 30 minutes, p-toluenesulfonic acid monohydrate (110 mg, 0.578 mmol) was added thereto, and 1.5 hours thereafter, 10% hydrous palladium-carbon (10 mg) and p-toluenesulfonic acid monohydrate (100 mg, 0.526 mmol) were additionally added thereto, and the mixture was heated under reflux for 3 days. After the palladium-carbon was filtered off, the filtrate was diluted with ethyl acetate and washed with a saturated aqueous ammonium chloride solution (×1). After extraction with 1N aqueous sodium hydroxide (×1), the aqueous layer was neutralized with 5N hydrochloric acid. The aqueous layer was extracted with ethyl acetate (×1), then dried over anhydrous sodium sulfate and concentrated. The residue was dissolved in methanol-5N hydrochloric acid (3 drops) and concentrated. The residue was crystallized from methanol/ethyl acetate/diethyl ether, and the solid was collected by filtration and washed with diethyl ether, to give the title compound 27 (18 mg, 20%) as a pale yellow solid.

$^1$H NMR (400 MHz, DMSO-d$_6$)δppm 1.45 (6H, s), 6.46 (1H, d, J=9.6 Hz), 7.31–7.38 (1H, m), 7.40–7.47 (2H, m), 7.47–7.56 (2Hmm), 7.73 (1H, d, J=2.8 Hz).

MS m/e (ESI):405 (MH$^+$).

Example 20

1-{2-[9-Allyl-6-amino-8-(3-fluorophenyl)-9H-2-purinyl]-1-ethynyl]}-1-cyclobutanol hydrochloride

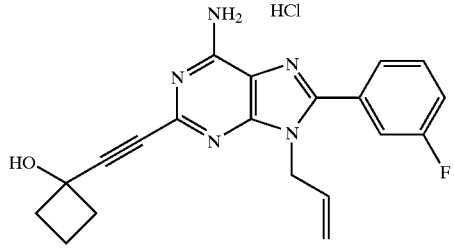

1) 1-{2-[9-Allyl-6-chloro-8-(3-fluorophenyl)-9H-2-purinyl]-1-ethynyl}-1-cyclobutanol Triethylamine (25.2 ml, 343 mmol) was added dropwise to a suspension of 9-allyl-6-chloro-8-(3-fluorophenyl)-2-iodo-9H-purine (50.0 g, 120.6 mmol), copper (I) iodide (1.1 g, 22 mmol), dichlorobis(triphenylphosphine) palladium (II) (4.2 g, 22 minol) and 1-(1-ethynyl)-1-cyclobutanol (12.7 g, 132 mmol) in tetrahydrofuran (500 ml) in a nitrogen atmosphere at room temperature, and the mixture was stirred for 2 hours. The reaction solution was diluted with a saturated aqueous ammonium chloride solution and ethyl acetate. The organic layer was washed with a saturated aqueous ammonium chloride solution (×1) and brine (×1), dried over anhydrous sodium sulfate and concentrated. The residue was suspended in diethyl ether, and the solid was collected by filtration and washed with diethyl ether, to give the title compound (45.0 g, 98%) as a pale brown solid.

¹H NMR (400 MHz, CDCl₃) δ ppm; 1.85–2.00 (2H, m), 2.32–2.42 (2H, m), 2.62–2.70 (2H, m), 5.00 (1H, d, J=15.0 Hz), 4.95–5.05 (2H, m) 5.32 (1H, d, J=10.4 Hz), 6.00–6.10 (2H, m), 7.24–7.35 (1H, m), 7.50–7.65 (3H, m).

2) 1-{2-[9-Allyl-6-amino-8-(3-fluoropheyl)-9H-2-purinyl]-1-ethyl}-1-cyclobutanol hydrochloride A suspension of 1-{2-[9-allyl-6-chloro-8-(3-fluorophenyl)-9H-2-purinyl]-1-ethynyl}-1-cyclobutanol (45 g, 116.8 mmol) in 1,2-dimethoxyethane (900 ml)/conc. ammonia water (450 ml) was stirred in an autoclave at 70° C. for 5 hours. After cooling as it was, the reaction solution was diluted with an aqueous saturated ammonium chloride solution (×1) and ethyl acetate. The organic layer was washed with a saturated aqueous ammonium chloride solution (×1), dried over anhydrous sodium sulfate, and concentrated. The residue was suspended in diethyl ether, and the solid was collected by filtration and washed with diethyl ether, to give the title compound in free form (31.3 g, 98%). This free compound was suspended in 300 ml ethanol, dissolved by adding 26 ml of 5N hydrochloric acid, and concentrated. The residue was washed with diethyl ether and dried, to give 30 g of the title compound (yield 64%)

¹H NMR (400 MHz, DMSO-d⁶) δ ppm; 1.72–1.83 (2H, m), 2.18–2.24 (2H, m), 2.33–2.40 (2H, m), 4.76 (1H, d, J=17.2 Hz), 4.86–4.92 (2H, m), 5.14 (1H, d, J=10.4 Hz), 5.95–6.05 (2H, m), 7.38–7.42 (1H, m), 7.58–7.65 (3H, m).

MS m/e (ESI):364.01 (MH⁺)

Example 21

5-[6-Amino-8-(2-furyl)-9H-9-purinyl]-1-methyl-1,2-dihydro-2-pyridinone hydrochoride

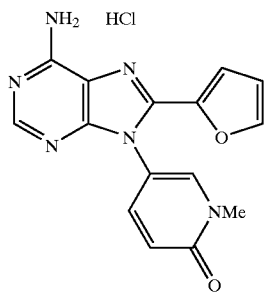

Sodiummethoxide (150 mg, 2.78 mmol) was added to a methanol (8 ml) suspension of 5-[6-amino-8-(2-furyl)-9H-9-purinyl]-1,2-dihydro-2-pyridinone (400 mg, 1.36 mmol) synthesized in the same method as in Example 1 (2), (3) and (4) and Example 2, and the mixture was stirred in a nitrogen atmosphere at room temperature. After 15 minutes, iodomethane (0.26 ml, 4.18 mmol) was added thereto and further stirred for 16.5 hours. The reaction solution was concentrated, and the residue was subjected to silica gel column chromatography (eluting solvent: hexane, hexane/ethyl acetate=40:1,20:1,10:1). The crude product was suspended in ethanol, and the solid was collected by filtration and washed with ethanol and diethyl ether, to give the title compound in free form (337 mg). The resulting free compound was dissolved in methanol-4N hydrochloric acid/ethyl acetate (0.4 ml) and concentrated. The residue was crystallized from methanol/ethyl acetate/diethyl ether, and the solid was collected by filtration and washed with diethyl ether, to give the title compound (270 mg, 58%) as a pale brown solid.

¹H NMR (400 MHz, DMSO-d₆) δ ppm; 3.50 (3H, s), 6.58 (1H, d, J=9.8 Hz), 6.68 (1H, dd, J=1.6, 3.6 Hz), 6.74 (1H, d, J=3.6 Hz), 7.60 (1H, dd, J=3.2, 9.8 Hz), 7.96 (1H, d, J=1.6 Hz), 8.24 (1H, d, J=3.2 Hz), 8.41 (1H, s)

MS m/e (ESI) 309 (MH⁺).

Example 22

5-[6-Aminon-8-(2-thienyl)-9H-9-purinyl]-1-methyl-1,2-dihydro-2-pyridinone hydochloride

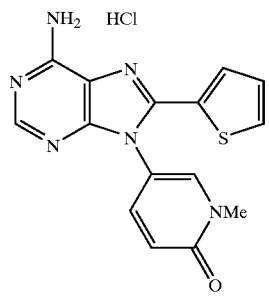

The title compound was synthesized in the same manner as in Example 1 (2), (3) and (4), and Examples 2 and 21.

¹H NMR (400 MHz, DMSO-d₆) δ ppm; 3.51 (3H, s), 6.61 (1H, d, J=9.6 Hz). 7.19 (1H, dd, J=3.8, 5.0 Hz), 7.41 (1H, dd, J=1.4, 3.8 Hz), 7.62 (1H, dd, J=2.8, 9.6 Hz), 7.83 (1H, dd, J =1.4, 5.0 Hz), 8.30 (1H, d, J=2.8 Hz), 8.45 (1H, s)

MS m/e (ESI) 325 (MH⁺)

Example 23

5-[6-Amino-8-(3-fluorophenyl)-9H-9-prrinyl]-1,4-dimethyl-1,2-dihydro-2-pyridinone hydrochloride

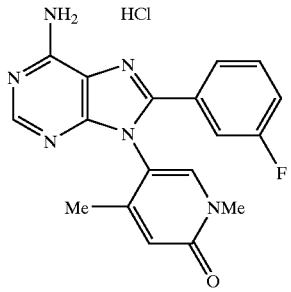

The title compound was synthesized in the same manner as in Examples 1,2 and 21.

¹H NMR (400 MHz, DMSO-d₆) δ ppm; 3.42 (3H, s), 6.46 (1H, s), 7.38–7.60 (4H, m), 8.13 (1H, s), 8.42 (1H, s)

MS m/e (ESI) 351 (MH⁺).

Example 24

5-[6-Amino-8-(3-fluorophenyl)-2-methyl-9H-9-purinyl]-1-menthyl-1,2-dihydro-2-pyridinone hydrochloride

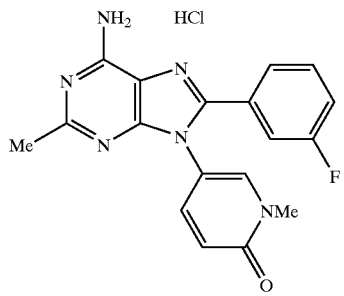

The title compound was synthesized in the same manner as in Examples 1,2 and 21.

$^1$H NMR (400 MHz, DMSO-d,) δ ppm; 2.54 (3H, s), 3.43 (3H, s), 6.51 (1H, d, J=10.0 Hz), 7.35–7.41 (1H, m), 7.44–7.57 (4H, m), 8.11 (1H, d, J=2.8 Hz)

MS m/e (ESI) 351 (MH$^+$).

Example 25

5-[6-Amino-8-(3-fluorophenyl)-9H-9-purinyl]1-ethyl-1,2-dihydron-2-pyridinone hydrochloride

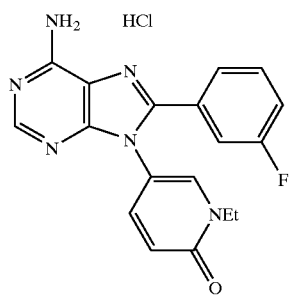

The title compound was synthesized in the same manner as in Example 21.

$^1$H NMR (400 MHz, DMSO-d,) δ ppm; 1.15 (3H, t, J=7.2 Hz), 3.89 (2H, q, J=7.2 Hz), 6.53 (1H, d, J=9.6 Hz), 7.38–7.43 (1H, m), 7.45–7.49 (2H, m), 7.53 (1H, dd, J=2.8, 9.6 Hz), 7.54–7.60 (1H, m), 8.10 (1H, d, J=2.8 Hz), 8.49 (1H, s)

MS m/e (ESI) 351 (MH$^+$)

Example 26

5-[6-(Cyclopropylamino)-8-(3-fluorophenyl)-9H-9-purinyl]-1-methlyl-1,2-dihydro-2-pyridinone

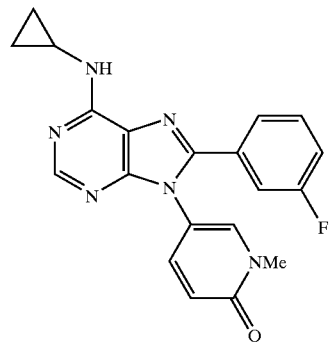

The title compound was synthesized in the same manner as in Examples 1 (4), 2 and 21.

$^1$H NMR (400 MHz, DMSO-d$_6$) δ ppm; 0.62–0.67 (2H, m), 0.72–0.80 (2H, m), 2.94–3.20 (1H, br), 3.43 (3H, s), 6.46 (1H, d, J=9.6 Hz), 7.28–7.34 (1H, m), 7.41–7.53 (4H, m), 8.09 (1H, d, J=2.8 Hz), 8.11–8.28 (1H, br), 8.24 (1H, br s)

MS m/e (ESI) 377 (MH$^+$).

Example 27

5-[6-(Cyclopropylamino)-8-(3-fluorophenyl)-9H-9-purinyl]-1-(2-hydroxyethyl)-1,2-dihydro-2-pyridinone

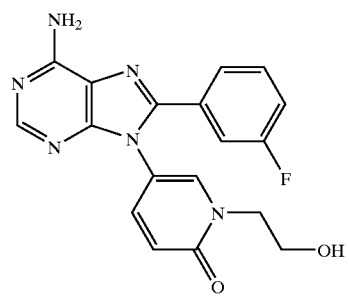

The title compound was synthesized in the same manner as in Example 21.

$^1$H NMR (400 MHz, DMSO-d$_6$) δ ppm; 3.58 (2H, q, J=5.2 Hz), 3.93 (2H, t, J=5.2 Hz), 4.86 (1H, t, J=5.2 Hz), 6.49 (1H, d, J =9.6 Hz), 7.29–7.36 (1H, m), 7.42–7.54 (6H, m), 7.94 (1H, d, J=2.8 Hz), 8.15 (1H, s)

MS m/e (ESI) 367 (MH$^+$)

Example 28

5-[6-(Cyclopropylamino)-8-(3-fluorophenyl)-9H-9-purinyl]-1-henzyl-1,2-dihydro-2-pyridinone

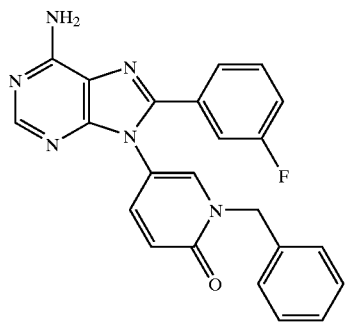

The title compound was synthesized in the same manner as in Example 21.

$^1$H NMR (400 MHz, DMSO-$d_6$) a ppm; 5.04 (2H, s), 6.57 (1H, d, J=9.6 Hz), 7.06–7.13 (2H, m), 7.26–7.44 (6H, m), 7.45–7.53 (3H, m), 7.63 (1H, dd, J=3.2, 9.6 Hz), 8.13 (1H, d, J=3.2 Hz), 8.16 (1H, s)

MS m/e (ESI) 413 (MH$^+$)

Example 29

1-Allyl-5-[6-amino-8-(3-fluorophenyl)-9H-9-purinyl]-1,2-dihydro-2-pyridinone

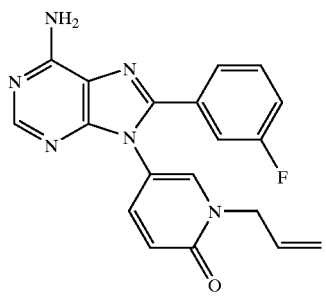

The title compound was synthesized in the same manner as in Example 21.

$^1$H NMR (400 MHz, DMSO-$d_6$) δ ppm; 4.49 (2H, d, J=5.2 Hz), 4.90 (1H, d, J=16.8 Hz), 5.10 (1H, d, J=6 10.4 Hz), 5.88 (1H, ddd, J=5.2, 10.4, 16.8 Hz), 6.54 (1H, d, J=9.6 Hz), 7.30–7.35 (1H, m), 7.41–7.53 (5H, m), 7.45–7.53 (3H, m), 7.56 (1H, dd, J=3.2, 9.6 Hz), 7.93 (1H, d, J=3.2 Hz), 8.16 (1H, s)

MS m/e (ESI) 363 (MH$^+$).

Example 30

2-[5-[6-Amino-8-(3-fluorophenyl)-9H-9-purinyl]-2-oxo-1,2-dihydro-2-pyridinyl] acetic acid

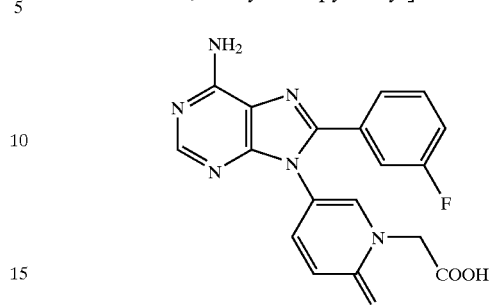

5N aqueous sodium hydroxide (2.0 ml, 10 mmol) was added to a solution, in methanol (6 ml)/tetrahydrofuran (6 ml)/water (10 ml), of ethyl 2-[5-[6-amino-8-(3-fluorophenyl)-9H-9-purinyl]-2-oxo-1,2-dihydro-2-pyridinyl] acetate (600 mg, 1.47 mmol) synthesized in the same manner as in Example 21, and the mixture was stirred at room temperature for 3 hours. The reaction solution was concentrated, dissolved in water and neutralized with 5N hydrochloric acid. The resulting crystals were collected by filtration and washed with water, to give the title compound (252 mg, 57%) as a colorless solid.

$^1$H NMR (400 MHz, DMSO-$d_6$) δ ppm; 4.61 (2H, s), 6.53 (1H, d, J=9.6 Hz), 7.29–7.35 (1H, m), 7.45–7.52 (5H, m), 7.55 (1H, dd, J=2.8, 9.6 Hz), 8.05 (1H, d, J=2.8 Hz), 8.16 (1H, s)

MS m/e (ESI) 381 (MH$^+$).

Example 31

2-[5-[6-Amino-8-(3-fluorophenyl)-9H-9-purinyl]-2-oxo-1,2-dihydro-2-pyridinyl] butyric acid

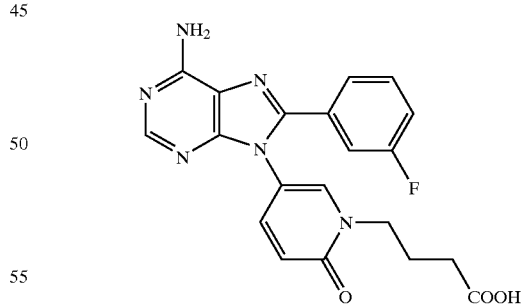

The title compound was synthesized in the same manner as in Examples 21 and 30.

$^1$H NMR (400 MHz, DMSO-$d_6$) δ ppm; 1.78 (2H, quint, J=7.2 Hz), 2.12 (2H, t, J=7.2 Hz), 3.89 (2H, t, J=7.2 Hz), 6.51 (1H, d, J=9.6 Hz), 7.28–7.34 (1H, m), 7.41–7.54 (6H, m), 7.99 (1H, d, J=2.8 Hz), 8.16 (1H, s)

MS m/e (ESI) 409 (MH$^+$).

Example 32

2-[5-[6-Amino-8-(3-fluorophenyl)-9H-9-purinyl]-2-oxo-1,2-dihydro-2-pyridinyl] acetamide

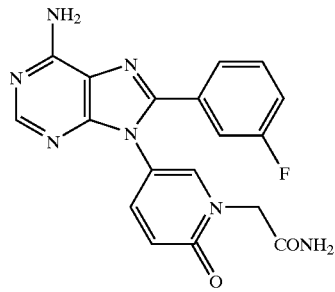

A suspension of 2-[5-[6-amino-8-(3-fluorophenyl)-9H-9-purinyl]-2-oxo-1,2-dihydro-2-pyridinyl]acetic acid (150 mg, 0.394 mmol), 1-hydroxybenzotriazole (180 mg, 1.18 mmol), ammonium chloride (105 mg, 1.96 mmol), 1-ethyl-3-(3'-dimethylaminopropyl) carbodiimide (184 mg, 1.19 mmol) and triethylamine (0.28 ml, 2.00 mmol) in N,N-dimethylformamide (3 ml) was stirred at room temperature for 20 hours. The reaction solution was concentrated, and the residue was subjected to silica gel column chromatography (eluting solvent: dichloromethane, dichloromethane/methanol=20:1, 10:1, 4:1). The crude product was suspended in ethanol, and the solid was collected by filtration and washed with ethanol, to give the title compound (96 mg, 64%) as a colorless solid.

$^1$H NMR (400 MHz, DMSO-d$_6$) δ ppm; 4.51 (2H, s), 6.48 (1H, d, J=9.6 Hz), 7.21 (1H, br s), 7.28–7.34 (1H, m), 7.45–7.54 (6H, m), 7.62 (1H, br 8), 7.98 (1H, d, J=2.8 Hz), 8.16 (1H, s)

MS m/e (ESI) 380 (MH+).

Example 33

5-{2-3-Fluorophenyl)-7,8-dihydro-3H-imidazo{2,1-i}purine-3-yl}-1,2-dihydro-2-pyridinone

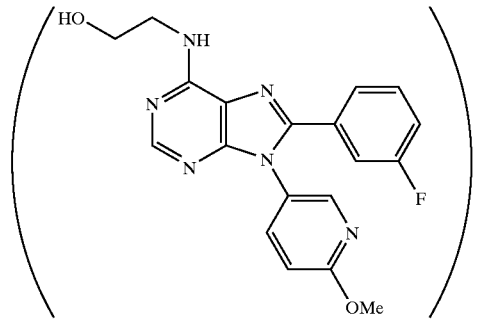

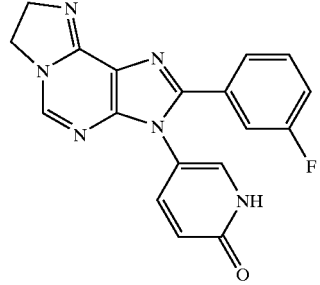

Thionyl chloride (1.1 ml, 15.1 mmol) was added to a suspension of 8-(3-fluorophenyl)-6-(2-hydroxyethylamino)-9-(6-methoxy-3-pyridyl)-9H-6-purine (800 mg, 2.10 mmol) synthesized in the same manner as in Example 1 (4) and Example 2 in 1,2-dichloroethane (20 ml), and the mixture was stirred at 80° C. for 9.5 hours. After cooling as it was, the reaction solution was concentrated and diluted with 1N hydrochloric acid and ethyl acetate. The aqueous layer was neutralized with 5N aqueous sodium hydroxide. The resulting crystals were collected by filtration and washed with water, to give 620 mg crude crystals. The resulting crude crystals were dissolved in conc. hydrochloric acid (10 ml) and heated under reflux for 8 hours. The reaction solution was left and cooled, and then neutralized with 5N aqueous sodium hydroxide. The resulting crystals were collected by filtration and washed with water, to give the title compound (210 mg, 29%) as a pale brown solid.

$^1$H NMR (400 MHz, DMSO-d$_6$) δ ppm; 3.95 (1H, t, J=9.4 Hz), 4.13 (1H, t, J=9.4 Hz), 6.43 (1H, d, J=9.2 Hz), 7.23–7.34 (1H, m), 7.33–7.40 (2H, m), 7.40–7.52 (2H, in), 7.68 (1H, d, J=2.8 Hz), 8.04 (1H, s)

MS m/e (ESI) 349 (MH$^+$).

Example 34

5-[6-Amino-8-(3-methylphenyl)-9H-9-purinyl]-1-methyl1,2-dihydro-2-pyridinone hydrochloride

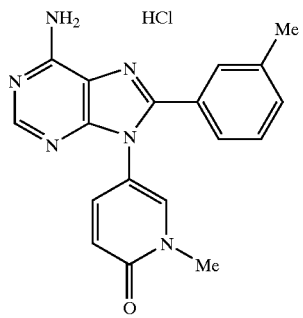

The title compound was synthesized in the same manner as in Example 1 (2), (3) and (4), and Examples 2 and 5.

$^1$H NMR (400 MHz, DMSO-d$_6$) δ ppm; 2.34 (3H, s), 3.45 (3H, s), 6.49 (1H, d, J=9.2 Hz), 7.32–7.40 (3H, m), 7.47 (1H, dd, J=9.2, 2.8 Hz), 7.61 (1H, s), 8.13 (1H, d, J=2.8 Hz), 8.38 (1H, s)

MS m/e (ESI) 333.01 (MH$^+$)

Example 35

5-[6-Amino-8-(3-methylphenyl)-9H-9-purinyl]-1-methyl-1,2-dihydro-2-pyridinone hydrochloride

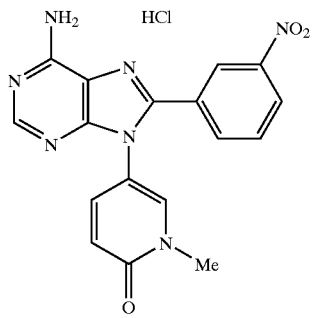

The title compound was synthesized in the same manner as in Example 1 (2), (3) and (4), and Examples 2 and 5.

$^1$H NMR (400 MHz, DMSO-$d_6$) δ ppm; 3.44 (3H, s), 6.51 (1H, d, J=9.6 Hz), 7.55 (1H, dd, J=9.6, 3.0 Hz), 7.79 (1H, t, J=8.0 Hz), 8.00–8.04 (1H, m), 8.16 (1H, d, J=3.0 Hz), 8.34 (1H, d, J=2.4 Hz), 8.36 (1H, s), 8.62 (1H, t, J=1.6 Hz)

MS m/e (ESI) 364.00 (MH$^+$).

Example 36

5-[6-Amino-8-(3-methylphenyl)-9H-9-purinyl]-1-methyl-1,2-dihydro-2-pyridinone dihydro chloride

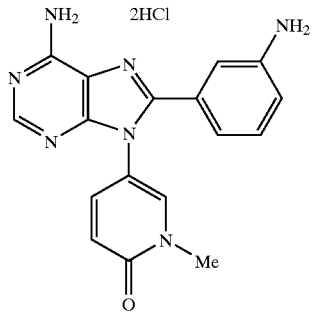

The free amine (371 mg) obtained in Example 35 was dissolved in THF (200 ml) and EtOH (200 ml), and 10% Pd—C (hydrous, 0.5 g) was added thereto, and the mixture was stirred for 2 hours in a hydrogen atmosphere at room temperature. The reaction mixture was filtered with Celite, and the filtrate was evaporated, to give 300 mg of the title compound in free form. This free amine (100 mg) was dissolved in methanol (2 ml), then 4N HCl/EtOAc (0.2 ml) was added thereto, and the precipitated crystals were collected by filtration, to give 84 mng of the title compound.

$^1$H NMR(400 MHz, DMSO-$d_6$) δ ppm; 3.47 (3H, s), 6.50 (1H, d, J=9.6 Hz) 7.21–7.27 (1H, m), 7.33–7.38 (1H, m), 7.42–7.53 (2H, m), 7.46 (1H, dd, J=9.6,2.6 Hz), 8.17 (1H, d, J=2.6 Hz), 8.49 (1H, s)

MS m/e (ESI) 334.02 (MH$^+$).

Example 37

N-[3-[Amino-9-(1-methyl-6-oxo-1,6-dihydro-3-pyridinyl)-9H-8-puridinyl]phenyl] methanesulfonamide hydrochloride

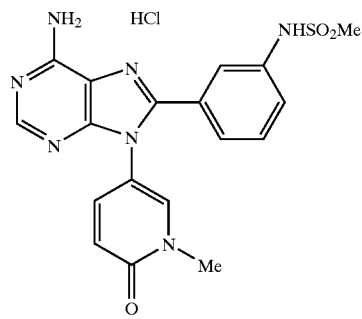

The free amine (100 mg) obtained in Example 36 was dissolved in pyridine (2 ml), and methanesulfonyl chloride (28 μl) was added thereto under ice-cooling and stirred at 0° C. overnight. The reaction solution was evaporated and purified by silica gel column chromatography, to give 90 mg of the title compound in free form. This free amine was dissolved in methanol (2 ml), then 4 N HCl/EtOAc (0.6 ml) was added thereto, and the precipitated crystals were collected by filtration, to give 55 mg of the title compound.

$^1$H NMR (400 MHz, DMSO-$d_6$) δ ppm; 2.93 (3H, s), 3.46 (3H, s), 6.48 (1H, d, j=9.6 Hz), 7.28–7.32 (1H, m), 7.42 (1H, dd, J=9.6, 3.0 Hz), 7.46–7.50 (2H, m), 7.59 (1H, s), 8.1:8 (1H, d, J=3.0 Hz) 8.45 (1H, s), 10.04 (1H, s)

MS m/e (ESI) 411.99 (MH$^+$).

Example 38

5-[6-Amino-8-(3-trifluoromethylphenyl)-9H-9-purinyl]-1-methyl]-1-methyl-1,2-dihydro-2-pyridinone hydrochloride

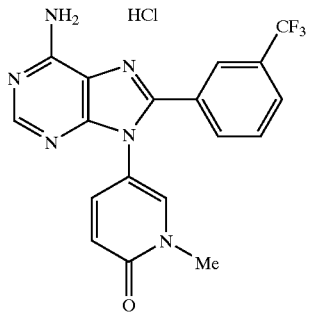

The title compound was synthesized in the same manner as in Example 1 (2), (3) and (4), and Examples 2 and 5.

$^1$H NMR (400 MHz, DMSO-$d_6$) δ ppm; 3.45 (3H, s), 6.53 (1H, d, J=9.6 Hz), 7.54 (1H, dd, J=9.6, 2.8 Hz), 7.75 (1H, t, J=2.8 Hz), 7.88–7.93 (2H, m), 8.10 (1H, s), 8.17 (1H, d, J=2.8 Hz), 8.43 (1H, s)

MS m/e (ESI) 387.00 (MH$^+$).

Example 39

5-[6-Amino-8-(3-chlorophenyl)-9H-9-purinyl]-1methyl-1,2-dihydro-2-pyridinone hydrochloride

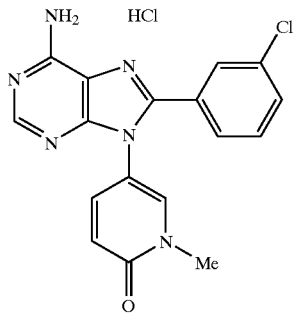

The title compound was synthesized in the same manner as in Example 1 (2), (3) and (4), and Examples 2 and 5.

$^1$H-NMR(400 MHz, DMSO-d$_6$) δ ppm; 3.43 (3H, s), 6.50 (1H, d, J=9.6 Hz), 7.47–7.61 (4H, m), 7.77–7.79. (1H, m), 8.12 (1H, d, J=2.8 Hz), 8.34 (1H, s).

MS m/e (ESI) 352.96 (MH$^+$).

Example 40

5-[6-Amino-8-(3-methoxyphenyl)-9H-9-purinyl]-1-methyl-1,2-dihydro-2-pyridinone hydrochloride

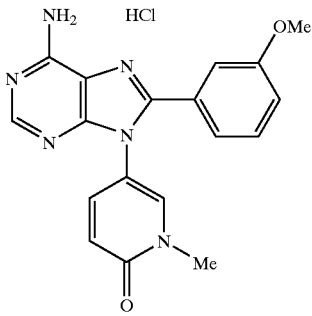

The title compound was synthesized in the same manner as in Example 1 (2), (3) and (4), and Examples 2 and 5.

$^1$H NMR (400 MHz, DMSO-d$_6$) δ ppm; 3.43 (3H, s), 3.73 (3H, s), 6.50 (1H, d, J=9.6 Hz), 7.06–7.11 (1H, m), 7.20–7.25 (2H, m), 7.38–7.43 (1H, m), 7.49 (1H, dd, J=9.6, 2.8 Hz), 8.14 (1H, d, J=2.8 Hz), 8.47 (1H, s)

MS m/e (ESI) 349.02 (MH$^+$).

Example 41

3-[6-Amino-9-(1-methyl-6-oxo-1,6-dihydro-3-pyridinyl)-9H-9-8-purinyl]benzonitrile hydrochloride

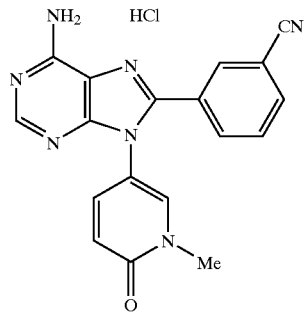

The title compound was synthesized in the same manner as in Example 1 (2), (3) and (4), and Examples 2 and 5.

$^1$H NMR (400 MHz, DMSO-d$_6$) δ ppm; 3.45 (3H, s), 6.51 (1H, d, J=10.0 Hz), 7.50 (1H, dd, J=10.0, 2.8 Hz), 7.72 (1H, t, J=8.0 Hz), 7.92–7.96 (1H, m), 7.99–8.03 (1H, m) 8.12–8.15 (1H, m) 8.14 (1H, d, J=2.8 Hz), 8.42 (1H, s)

MS m/e (ESI) 343.99 (MH$^+$).

Example 42

2-(3-Fluorophenyl)-1-(6-methoxy-3-pyridyl)-1H-imidazo[4,5-c]pyridine-4-amine

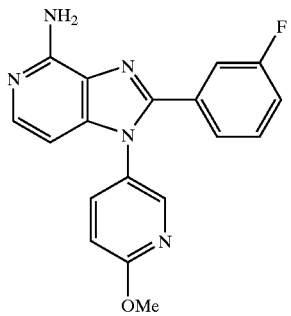

(1) 2,4-Dichloro-3-nitropyride

Phosphorus oxychloride (10 mL) was added to 2,4-dihydroxy-3-nitropyridine (2.5 g, 16 mmol) and stirred at 110° C. for 4 hours. The reaction solution was evaporated. Ethyl acetate and iced water were added to the residue, which were then filtered through Celite. The organic layer was washed with brine, dried over anhydrous magnesium sulfate, filtered through silica gel and concentrated, to give the title compound (2.7 g, 87%) as a brown solid.

2) N4-(6-Methoxy-3-pyridyl)-2-chloro-3-nitro4-pyridineamine

A mixture of the compound (10.4 g, 54 mmol) obtained in (1), 5-amino-2-methoxypyridine (9.6 g, 77 mmol), trimethylamine (5.4 g, 54 mmol) and ethanol (40 mL) was stirred for 2 days at room temperature. The reaction solution was evaporated, and ethyl acetate and water were added to the residue. The organic layer was washed with brine, dried over anhydrous magnesium sulfate and concentrated. The product was purified by silica gel column chromatography, to give the title compound (6.3 g, 42%).

¹H NMR (400 MHz, CDCl₃) δ ppm; 3.98 (3H, s), 6.63 (1H, d, J=6.4 Hz), 6.85 (1H, d, J=8.8 Hz), 7.46 (1H, dd, J=8.8, 2.8 Hz), 7.92–7.96 (1H, m), 7.99 (1H, dd, J=6.4, 0.8 Hz), 8.10 (1H, d, J=2.8 Hz).

(3) N4-(6-Methoxy-6-pyridyl)-2-chloro-3,4-pyridinediamine

The compound (1.0 g) obtained in (2) was suspended in water (10 mL) and ethanol (20 ml), and zinc powder (1.0 g) and acetic acid (1 mL) were added thereto and stirred for 4 hours at room temperature. The reaction solution was filtered through Celite and evaporated. Ethyl acetate and a saturated aqueous sodium bicarbonate solution were added to the residue, which were then filtered. The organic layer was washed with brine, dried over anhydrous magnesium sulfate, filtered with silica gel and concentrated, to give the title compound (0.85 g, 95%).

¹H NMR (400 MHz, CDCl₃) δ ppm; 3.95 (3H, s), 5.79 (1H, S), 6.59 (1H, d, J=5.6 Hz), 6.79 (1H, d, J=8.8 Hz), 7.42 (1H, dd, J=8.8,2.8 Hz), 7.70 (1H, d, J=5.6 Hz), 8.01 (1H, d, J=2.8 Hz).

(4) N1-[2-Chloro-4-[(6-methoxy-3-pyridyl)amino-3-pyridyl]-3-fluorobenzamide

The compound (1.0 g, 4.0 mmol) obtained in (3) was dissolved in pyridine (5 mL), and 3-fluorobenzoyl chloride (1.0 g) was added thereto under ice-cooling, and the mixture was stirred for 5 hours at room temperature. The reaction solution was evaporated, and the residue was diluted with ethyl acetate and washed with water and brine. The product was dried over anhydrous magnesium sulfate and concentrated. The product was purified by silica gel column chromatography, to give the title compound (1.2 g, 81%).

¹H NMR (400 MHz, CDCl₃) δ ppm; 3.95 (3H, s), 6.73 (1H, d, J=5.6 Hz), 6.79 (1H, d, J=8.4 Hz), 6.97 (1H, s), 7.31–7.37 (1H, m), 7.46 (1H, dd, J=8.4, 2.8 Hz), 7.51 (1H, m), 7.69–7.79 (2H, m), 7.95 (1H, s), 7.96 (1H, d, J=5.6 Hz), 8.07 (1H, d, J=2.8 Hz).

(5) 4-Chloro-2-(3-fluoropheyl)-1-(6-methoxy-3-pyridyl)-1H-imidazo [4,5-c]pyridine A mixture of the compound (980 mg, 2.6 mmol) obtained in (4), acetonitrile (20 mL) and phosphorus oxychloride (2 mL) was stirred at 80° C. for 3 hours. The reaction solution was evaporated, and the residue was diluted with ethyl acetate and washed with water and brine. The product was dried over anhydrous magnesium sulfate and concentrated. The product was purified by silica gel column chromatography, to give the title compound (680 mg, 73%)

¹H NMR (400 MHz, CDCl₃) δ ppm; 4.03 (3H, s), 6.91 (1H, dd, J=8.8,0.8 Hz), 7.11 (1H, d, J=5.6 Hz), 7.11–7.17 (1H, m), 7.33–7.40 (3H, m), 7.47 (1H, dd, J=8.8,2.8 Hz), 8.17 (1H, dd, J=2.8,0.8 Hz), 8.23 (1H, d, J=5.6 Hz).

(6) 2-(3Fluoropheyl)-1-(6-methoxy-3-pyridyl)-1H-imidazo [4,5-c]pyridine-4-amine

A mixture of the compound (1 g) obtained in (5) and an ammonia-ethanol solution (20 mL) was stirred at 150° C. for 4 days. The reaction solution was evaporated, and the residue was purified by silica gel column chromatography, to give the title compound (200 mg, 21%).

¹H NMR (400 MHz, CDCl₃) δ ppm; 4.02 (3H, s), 5.30 (2H, br), 6.55 (1H, dd, J=5.8 Hz), 6.88 (1H, d, J=8.8 Hz), 7.07–7.13 (1H, m), 7.24–7.35 (3H, m), 7.46 (1H, dd, J=8.8, 2.8 Hz), 7.88 (1H, d, J=5.8 Hz), 8.15 (1H, d, J=2.8 Hz)

MS m/e (ESI) 336.00 (MH⁺).

Example 43

5-[4-Amino-2-(3-fluorophenyl)-1H-imidazo[4,5-c]-pyridin-1-yl]-1,2-dihydro-2-pyridinone

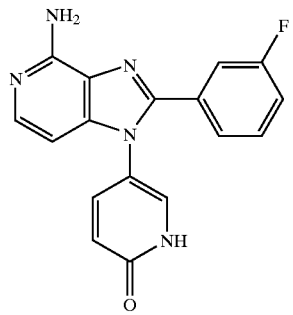

A mixture of 2-(3-fluorophenyl)-1-(6-methoxy-3-pyridyl)-1H-imidazo[4,5-clpyridine-4-amine (290 mL) obtained in Example 42 and conc. hydrochloric acid (10 mL) was stirred at 110° C. for 7.5 hours. The reaction solution was evaporated, and the residue was purified by NH-form silica gel column chromatography, to give the title compound (120 mg, 43%)

¹H NMR (400 MHz, DMSO-d₆) δ ppm; 6.39 (2H, br), 6.45 (1H, d, J=9.6 Hz), 6.49 (1H, d, J=5.8 Hz), 7.28–7.34 (1H, m), 7.40–7.54 (4H, m), 7.72 (1H, d, J=5.8 Hz), 7.77 (1H, d, J=2.8 Hz)

MS m/e (ESI) 321.94 (MH⁺).

Example 44

5-[4-Amino-2-(3-fluorophenyl)-1H-imidazo]4,5-c]pyridin-1-yl]1-methyl-1,2-dihydro-2-pyridinone

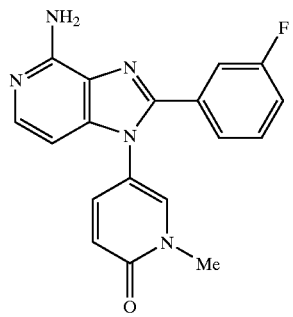

5-[4-Amino-2-(3-fluorophenyl)-1H-imidazo[4,5-c]pyridin-1-yl]-1,2-dihydro-2-pyridinone (100 mg) obtained in Example 43 was suspended in methanol (1 mL), and 28% sodium methoxide-methanol solution (20 mL) and methyl iodide. (20 mL) were added thereto and stirred for 1 day at room temperature. The reaction solution was evaporated, and the residue was purified by NH-form silica gel column chromatography, to give the title compound (27 mg, 26%).

¹H NMR (400 MHz, DMSO-d₆) δ ppm; 3.45 (3H, s), 6.40 (2H, br), 6.49 (1H, d, J=9.6 Hz), 6.56 (1H, d, J=5.8 Hz), 7.29–7.34 (1H, m), 7.44–7.53 (4H, m), 7.73 (1H, d, J=5.8 Hz), 8.17 (1H, d, J=2.8 Hz)

MS m/e (ESI) 335.98 (MH⁺).

Example 45

3-[6-Amino-8-(3-fluorophenyl)-9H-9-purinyl]-1-methyl-1,2-dihidro-2-pyridinone hydrochloride

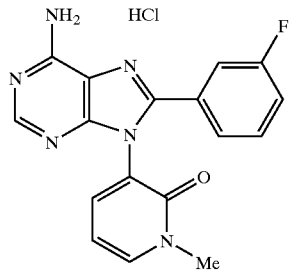

The title compound was obtained in the same manner as in Examples 1,2 and 5.

$^1$H NMR (400 MHz, DMSO-$d_6$) δ ppm; 3.46 (3H, s), 6.45 (1H, t, J=7.0 Hz), 7.30–7.53 (4H, m), 7.91 (1H, dd, J=7.2, 0.8 Hz), 7.97 (1H, dd, J=7.2, 0.8 Hz), 8.33 (1H, s)

MS m/e (ESI) 336.97 (MH$^+$).

Example 46

5-[-6-Amino-8-(3-fluorophenyl)-9H-9-purinyl]-1-methyl-1,2-dihydro-2-pyridinone

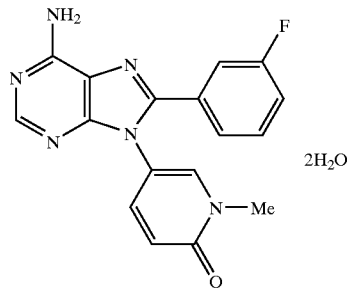

(1) 1-Methyl-5-nitro-2 (pyridone

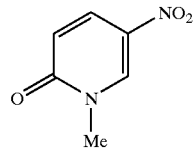

5-Nitro-2-hydroxypyridine (0.55 kg, 3.93 mol), DMSO (2.2 L) and $K_2CO_3$ (0.88 kg, 6.37 mol) were introduced successively into a flask and stirred until foaming was terminated. Further, pTsOMe (0.88 kg, 4.71 mol) was added dropwise thereto in a warm bath at 37° C. and stirred for 1 hour.

After 11 L water was added dropwise thereto, the reaction solution was ice-cooled, and the precipitated crystals were collected by filtration and dried in vacuo at 70° C., to give 516 g of the title compound (yield, 85%) as a yellow powder.

(2) 5-Amino-1-methyl-2 (1H)-pyridone oxalate

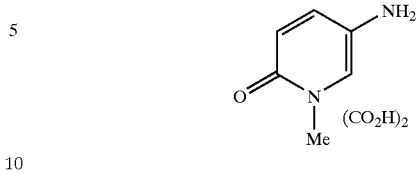

1-Methyl-5-nitro-2 (1H)-pyridone (250 g, 1.62 mol), 10% Pd—C (25 g, 0.1 w/w-%) and EtOH (2.5 L) were introduced into an autoclave and suspended. Hydrogen was introduced to keep 10 kg/cm$^2$, followed by leakage after 30 minutes, and the catalyst was separated off through Celite, and the resulting cake was further washed with EtOH (1.25 L).

A solution of oxalic acid (293 g, 3.2 mol) in EtOH (2.5 L) was added dropwise to the filtrate and stirred in an ice-cold bath, and the resulting crystals were collected by filtration and washed with EtOH (1 L). The crystals were air-dried at 60° C., to give 182.6 g of the title compound (yield 52.6%)

$^1$H NMR(DMSO-$d_6$) δ ppm 3.30 (s, 3H, N-Me), 6.25 (d, 1H, J=9.3 Hz,H-3), 6.91 (d, 1H, J=2.9 Hz, H-6), 7.07 (dd, 1H, J=9.3 Hz, 2.9 Hz, H-4).

m.p.: 224–226° C.

(3) 5-(5-Amino-6-chloropyrimidine-4-yl)minn-1l-methyl-1,2-dihydro-2-pyridinone

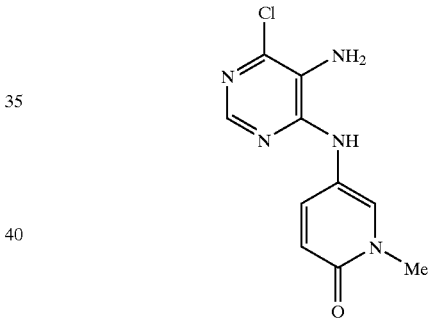

118.6 g of 5-amino-4,6-dichloropyrimidine, 170.0 g of 5-amino-1-methyl-2 (1H)-pyridone oxalate, 360 mL EtOH and 2.4 L purified water were introduced successively to a flask and heated for 17 hours at a bath temperature of 110° C.

The reaction solution was cooled in an ice-cold bath, and 200 mL ammonia water was poured there into and stirred for 1 hour, and the crystals were collected by filtration, washed with 750 mL water and air-dried at 60° C., to give 188.2 g of the title compound as crude material.

Then, this crude material, 188 g, was suspended in 1.9 L (10 vol.) water, and 100 mL ammonia water was added thereto and stirred. After 2 hours, the crystals were collected by filtration, washed with 1 L water and air-dried at 60° C. for 18 hours, to give 153.8 g of the title compound.

$^1$H NMR (DMSO-$d_6$) δ ppm; 3.42 (s, 3H, NMe-1'), 5.27 (brs, 2H, NH2-5) 6.40 (d, 1H, J=9.7 Hz, H-3'), 7.49 (dd, 1H, J=9.7 Hz, 2.4 Hz, H-4'), 7.77 (s, 1H, H-2), 7.98 (d, 1H, J=2.4 Hz, H-6'), 8.35 (s, 1H, NH-4)

m.p.: 258° C. (decomp.)

(4) 5-[6-Chloro-5-(3-fluorobzoyl)aminopyrimiidin-4-yl]amino-1,2-dihydro-2-pyridinone

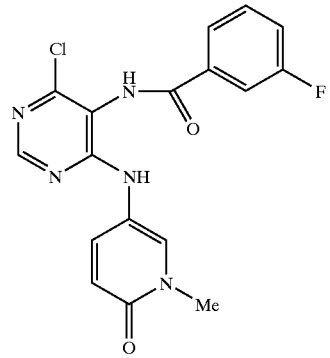

148.9 g 5-(5-amino-6-chloropyrimidine-4-yl)arnino-1-methyl-1,2-dihydro-2-pyridinone and 1490 mL (10 vol.) pyridine were introduced into a flask and ice-cooled, and 98.1 mL (1.38 eq.) of 3-fluorobenzoyl chloride was added dropwise thereto.

After 1 hour, 1490 mL (10 vol) was poured into the reaction solution, evaporated, and 500 mL DME and 1490 mL water (10 vol) were poured successively into the residue and stirred at room temperature. The resulting crystals were collected by filtration, washed with 1600 mL DME/H$_2$O=1/5 and air-dried at 70° C. for 24 hours, to give 196.4 g of 5-[6-chloro-5-(3-fluorobenzoyl) aminopyrimidin-4-yl] amino-1,2-dihydro-2-pyridinone.

$^1$H NMR (DMSO-d$_6$) δ ppm; 3.41 (s, 3H, NMe-1'), 6.38 (d, 1H, J=9.71 Hz, H-3'), 7.45–7.50 (m, 2H), 7.60 (dd, 1H, J-14.0 Hz, 7.0 Hz, H-5"), 7.78–7.90 (m, 3H), 8.30 (s, 1H, H-2), 9.09 (brs, 1H, NH-4), 10.08 (brs, 1H, NH-5)

m.p.: 173t (decomp.)

(4-2) 5-[Chloro-5-(3-fluorobenzoyl)aminopyridine-4-yl]amino-1,2-dihydro-2-pyridinone hydrochloride Acetonitrile (50 mL) was added to 5-[6-chloro-5-(3-fluorobenzoyl) aminopyrimidin-4-yl]amino-1,2-dihydro-2-pyridinone (2.0 g) and heated in an oil bath at 85° C., and the insoluble matters were subjected to hot-filtration. The filtrate was diluted with acetonitrile (110 mL) and heated again to form a solution, and 4N HCl (1.30 mL, 0.97 eq.) was added thereto. Further, additional acetonitrile (20 mL) was added thereto and the crystals were collected by filtration, washed with acetonitrile (20 mL) and air-dried at 60° C., to give a pale bluish white powder (1.59 g, yield 72.5%).

$^1$H NMR (DMSO-d$_6$) δ ppm 3.43 (s, 3H, NMe-1'), 6.43 (d, 1H, J=9.5 Hz, H-3'), 7.40–7.53 (m, 2H), 7.60 (dd, 1H, J=14.0 Hz, 8.0 Hz, H-5"), 7.77–7.93 (m, 3H), 8.31 (s, 1H, H-2), 9.16 (s, 1H, NH-4), 10.17 (s, 1H, NH-5)

m.p.: 193–195° C. (decomp.)

(5) 5-[6-Chloro-8-(3-fluorophenyl)-9-9-purinyl]-1-methyl-1,2-dihydro-2-pyridinone

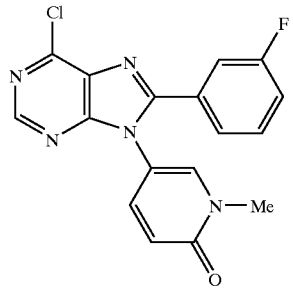

186.0 g 5-[6-chloro-5-(3-fluorobenzoyl)aminopyridin-4-yl]amino-1,2-dihydro-2-pyridinone, 1.9 L CH$_3$CN, 186.0 mL POCl$_3$ (2.0 mol, 1 vol=4 eq.) were introduced into a flask and heated under reflux for about 6 hours in an oil bath (bath temperature, 120° C.).

The reaction solution was concentrated, and 372 mL CH$_3$CN was added to and dissolved in it, and the solution was further evaporated. After it was concentrated, it was diluted with 1.9 L AcOEt, then 900mL of 30% aqueous K$_2$CO$_3$ solution was poured into it, and the mixture was partitioned by adding 1 L water and 1.9 L AcOEt. The organic layer was washed with 1.9 L water and evpoarated, to give 161.5 g (wet) 5-[6-chloro-8-(3-fluorophenyl)-9H-9-purinyl]-1-methyl-1,2-dihydro-2-pyridinone as a grayish green powder.

$^1$H NMR(DMSO-d$_6$) δ ppm 3.44 (s, 3H, NMe-1'), 6.52 (d, 1H, J=9.7 Hz, H-3'), 7.38–7.47 (m, 1H), 7.50–7.62 (m, 5H), 8.18 (d, 1H, J=2.8 Hz, H-6'), 8.80 (d, 1H, J=1.1 Hz, H-2)

m.p.: 219° C.

(5-2) 5-[6-Chloro-8-(3-fluorophenyl)-9H-9-purinyl]-1-methyl-1,2-dihydro-2-pyridinone 5-[6-Chloro-5-(3-fluorobenzoyl)aminopyrimidin-4-yl]amino-1,2-dihydro-2-pyridinone hydrochloride (5 g) and NMP (25 mL) were introduced into a flask and stirred at 110° C. for 4 hours. The reaction solution was extracted with ethyl acetate (100 mL) and 10% aqueous sodium bicarbonate solution (50 mL) After liquid partition, the organic layer was washed with brine (50 mL), and the organic layer inan amount of 1/5 of the original layer was used in the following crystallization.

After this organic layer was concentrated, DME (10 ML) was added to the concentrate which was then dissolved at 55° C. under stirring and crystallized by adding water (20mL). The crystals were collected by filtration and dried at 50° C.'for 16 hours, to give 0.64 g 5-[6-chloro-8-(3-fluorophenyl)-9H-9-purinyl]-1-methyl-1,2-dihydro-2-pyridinone as a slight brownish white compound (yield 73.8%).

(5-3) 5-[6-Chloro-8-(3-fluorophenyl)-9H-9-purinyl]-1-methyl-1,2-dihydro-2-pyridinone
*HCl-EtOAc method 5-[6-Chloro-5-(3-fluorobenzoyl)aminopyrimidin-4-yl]amino-1,2-dihydro-2-pyridinone (1 g, 2.7 mmol) was dissolved in NMP (10 mL), and 4N HCl/EtOAc (0.8 mL, 3.2 imol) was added thereto and stirred under heating at 110° C. for 14 hours. By analyzing the reaction solution in HPLC, it was confirmed that 5-[6-chloro-8-(3-fluorophenyl)-9H-9-purinyl]-1-methyl-1,2-dihydro-2-pyridinone (90.2%) was formed.

(5-4) 5-[6-Chloro-8-(3-fluorophenyl)-9H-9-purinyl]-1-methyl-1,2-dihydro-2-pyridinone

*Non-catalytic method

5-[6-Chloro-5-(3-fluorobenzoyl)aminopyrimidin-4-yl]amino-1,2-dihydro-2-pyridinone (1 g, 2.7 mmol) was dissolved in NMP (2 mL) and stirred under heating at 140° C. for 10 hours. By analyzing the reaction solution in HPLC, it was confirmed that 5-[6-chloro-8-(3-fluorophenyl)-9H-9-purinyl]-1-methyl-1,2-dihydro-2-pyridinone (91.3%) was formed.

(5-5) 5-[6–Chloro-8-(3-fluorophenyl)-9H-9-purinyl]-1-methyl-1,2-dihydro-2-pyridinone
(one-pot reaction: 5-(5-amino-6-chloropyrimidin-4-yl)amino-1-methyl-1,2-dihydro-2-pyridinone5-[6-chloro-5-(3-fluorobenzoyl) aminopyrimidin-4-yl]amino-1,2-dihydro-2-pyridinone →5-[6-chloro-8-(3-fluorophenyl)-9H-9-purinyl]-1-methyl-1,2-dihydro-2-pyridinone)

5-(5-Amino-6-chloropyrimidin-4-yl)amino-1-methyl-1,2-dihydro-2-pyridinone (1 g) and NMP (10 mL) were introduced into a flask and stirred at 40° C. 3-Fluorobenzoyl chloride (0.53 mL, 1.1 eq.) was added dropwise to this suspension, and after additional NMP (3.2 mL) was added thereto and stirred for about 1.5 hours, the reaction solution was elevated to 110° C. and stirred for 3 hours. Ethyl acetate (33 mL) and 10% aqueous sodiumbicarbonate solution (16.5 mL) were added to the reaction solution, and the organic layer was washed with brine (16.5 mL) and concentrated. The concentrate was dissolved by adding DME (16.5 mL) and stirring it at 55° C., and then crystallized by adding water (33 mL). The crystals were collected by filtration and dried at 50° C. for 4 hours, to give 0.94 g of 5-[6-chloro-8-(3-fluorophenyl)-9H-9-purinyl]-1-methyl-1,2-dihydro-2-pyridinone (two-steps, yield 66.7%)

(6) 5-[6-Amino-8-(3-fluorophenyl)-9H-9-purinyl]-1-methyl-1,2-dihydro-2-pyridinone

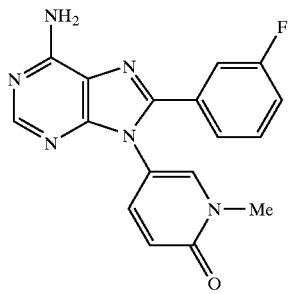

160.0 g crude crystals (wet) of 5-[6-chloro-8-(3-fluorophenyl)-9H-9-purinyl]-1-methyl-1,2-dihydro-2-pyridinone (content 96.0%; net weight, 155 g), 2600 mL DME and 1300 mL conc. ammonia water (28–30%) were introduced into an autoclave and heated at an external temperature of 750° C. After 1.5 hours, the external temperature was elevated to 90° C., and the mixture was stirred for 8.5 hours in total after heating was initiated.

6.5 L deionized water was added to the reaction solution which was then ice-cooled, and the precipitated crystals were collected by filtration, washed with 500 mL water and dried, to give 135.0 g of the title compound.

(7) 5-[6-Amino-8-(3-fluorophenyl)-9H-9-purinyl]-1-methyl-1,2-dihydro-2-pyridinone 2H$_2$O

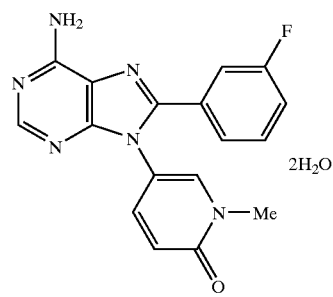

130 g crude crystals of 5-[6-amino-8-(3-fluorophenyl)-9H-9-purinyl]-1-methyl-1,2-dihydro-2-pyridinone, 1.3 L methanol-modified ethanol (mixture of EtOH/MeOH in a ratio of 2000 mL/50 g) and 1.3 L water were introduced into a flask and heated in a water bath at 90° C.

After the heater was turned off, the mixture was stirred at a decreasing temperature, and the precipitated crystals were collected by filtration and washed with 200 mL methanol-modifiedethanol. The product was dried under reduced pressure, to give 119.1 g of the title compound.

$^1$H NMR (DMSO-d$_6$) δ ppm; 3.43 (5, 3H, NMe-1), 6.46 (d, 1H. J=9.7 Hz, H-3'), 7.26–7.36 (m, 1H), 7.36–7.60 (m, 6H), 8.09 (d, 1H, J=2.8 Hz, H-6'), 8.14 (s, 1H, H-2)

m.p.: 244° C. (decomp.)

Example 47

6-Chloro-9-(2-chloro-4-pyridyl)-8-(3-fluorophenyl)-9H-purine

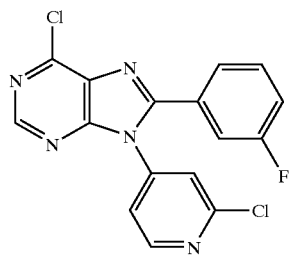

(1) N-(6-Chloro-5-nitro-4-pyrimidinyl)-N-(2-chloro-4-pyridyl)amine

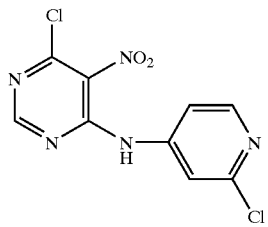

4-Amino-2-chloropyridine (8.0 g, 62.2 mmol) and triethylamine (8.7 mL) were added. successively to a suspension of 5-nitro-4,6-dichloropyrimidine (8.0 g, 41.2 mmol) in tetrahydrofuran (160 mL), and the mixture was heated under reflux for 4 hours. After cooling as it was, the reaction solution was diluted with ethyl acetate (160 ml) and washed with 160 ml water and brine, and the organic layer was dried over anhydrous magnesium sulfate. The solvent was evaporated, and the residue were suspended in diethyl ether, and the resulting solid was collected by filtration and air-dried, to give the title compound (2.2 g, 19%).

¹H NMR (400. MHz, CDCl₃) δ ppm; 7.39 (1H, dd, J=1.9, 5.5 Hz), 7.79 (1H, d, J=2.0 Hz), 8.31 (1H, d, J=5.6), 8.62 (1H, s), 9.14 (1H, bs)

(2) N4-(2-Chloro-4-pyridyl)-6-chloro-4,5-pyrimidine diamine

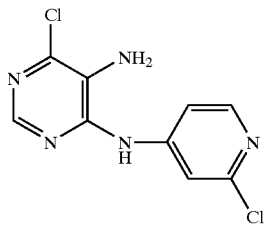

N-(6-Chloro-5-nitro-4-pyrimidinyl)-N-(2-chloro-4-pyridyl)amine (2.2 g, 7.6 mmol) was suspended in 44 ml ethanol and 4.4 ml acetic acid, and 2.2 g zinc powder was added little by little thereto at 0° C. The reaction solution was returned to room temperature and stirred for 1 hour, and then the insoluble matters were filtered off. The filtrate was concentrated and suspended in water, and the resulting solid was collected by filtration and air-dried, to give 2.5 g of the title compound in crude form.

¹H NMR (400 MHz, CDCl₃) δ ppm; 7.52 (1H, dd, J=2.0, 5.9), 7.84 (1H, J=2.0), 8.12 (1H, J=5.5), 8.13 (1H, S)

(3) N1-{4-Chloro-6-[(2-chloro-4-pyridyl)amino]-5-pyrimidinyl}-3-fluorobenzamide

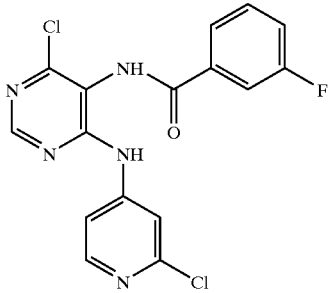

3-Fluorobenzoyl chloride (1.3 mL, 10.7 mmol) was added dropwise to a suspension of N4-(2-chloro-4-pyridyl)-6-chloro-4,5-pyrimidine diamine (2.5 g, 9.8 mmol) in pyridine (50 mL) over 5 minutes in a nitrogen atmosphere at 0 to 5° C., and the mixture was stirred as such for 12 hours. The reaction solution was diluted with water and ethyl acetate (100 mL). The organic layer was washed with 1N hydrochloric acid (×1). After the 1N hydrochloric acid layer was extracted with ethyl acetate (×2), the combined organic layers were washed with a saturated aqueous sodium bicarbonate solution (×1), dried over anhydrous sodium sulfate and concentrated. The residue was suspended in diethyl ether, and the solid was collected by filtration and washed with diethyl ether, to give the title compound (2.3 g, 62%) as a colorless solid.

¹H NMR (400 MHz, CDCl₃) δ ppm; 7.38–7.42 (2H, m), 7.56–7.62 (1H, m) 7.70–7.78 (3H, m), 7.99 (1H, bs), 8.27 (1H, d, J=5.7), 8.60 (1H, s)

Then, a suspension of N1-{4-chloro-6-[(2-chloro-4-pyridyl)amino]-5-pyrimidinyl}-3-fluorobenzamide (2.3 g, 6.1 mmol) in phosphorus oxychloride (75 mL) was heated under reflux for 1.5 hours in a nitrogen atmosphere. After cooling as it was, the reaction solution was evaporated. The residue was diluted with ethyl acetate (100 ml), washed with water (×3), a saturated aqueous sodium bicarbonate solution (×2) and brine (×1), dried over sodium sulfate anhydride and concentrated. The residue was suspended in diethyl ether, and the solid was collected by filtration and washed with diethyl ether, to give the title compound (1.0 g, 46%) as a colorless solid.

¹H NMR (400 MHZ, CDCl₃) δ ppm; 7.21 (1H, d, J=1.8, 5.3 Hz), 7.24–7.30 (2H, m), 7.39–7.48 (3H, m), 8.56 (1H, d, J=5.3 Hz), 8.79 (1H, s).

Example 48

9-(2-Chloro-4-pyridi)-8-(3-fluorophenyl)-9H-6-purineamine

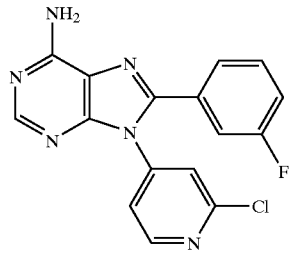

A suspension of 6-chloro-9-(2-chloro-4-pyridyl)-8-(3-fluorophenyl)-9H-purine (325 mg, 0.9 mmol) in Example 47 in 1,2-dimethoxyethane (10 mL)/conc. ammonia water (5 mL) was stirred for 11 hours in an autoclave at 80° C. After cooling as it was, the reaction solution was diluted with a saturated aqueous ammonium chloride solution and ethyl acetate. The organic layer was washed with a saturated aqueous ammonium chloride solution (×1), dried over anhydrous sodium sulfate and concentrated. The residue was suspended in diethyl ether, and the solid was collected by filtration and washed with diethyl ether, to give the title compound (229 mg, 75%) as a colorless solid.

¹H NMR (400 MHz, CDC₃) δ ppm; 5.75 (2H, br), 7.16–7.24 (2H, m), 7.31–7.41 (2H, m), 7.44 (1H, d, J=1.8 Hz), 8.41 (1H, s), 8.51 (1H, d, J=5.3 Hz), 8.14 (1H, s), 8.23 (1H, d, J=2.8 Hz)

Example 49

8-(3-Fluoropheyl)-9-{2-[(4-methnxyhonyl)oxy]-4-pyridyl}-9H-6-purineamine

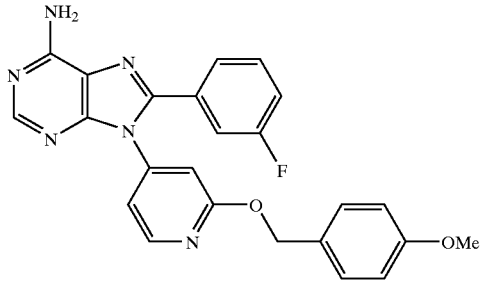

200 mg metal sodium was dissolved in 4-methoxybenzyl alcohol at 80° C., and 9-(2-chloro-4-pyridyl)-8-(3-fluorophenyl)-9H-6-purineamine (596 mg, 1.75 mmol) in Example 48 was added thereto and stirred for 1 hour. After cooling as it was, the reaction solution was diluted with water and extracted with ethyl acetate. The organic layer was dried over anhydrous magnesium sulfate and evaporated. The residue was suspended in a mixture of ethyl acetate and hexane, and the formed solid was collected by filtration and washed with diethyl ether, to give the title compound (690 mg, 89%) as a colorless solid.

$^1$H NMR (400 MHz, CDCl$_3$) δ ppm; 3.80 (3H, s), 5.34 (2H, s), 6.13 (2H, bs), 6.80–6.88 (2H, m), 6.90 (2H, d, J=8.1 Hz), 7.10–7.16 (1H, m), 7.23–7.35 (2H, m), 7.37 (2H, d, J=8.2 Hz), 8.28 (1H, d, J=5.3 Hz), 8.36 (1H, s).

Example 50

4-[6-Amino-8-(3-fluorophenyl)-9H-9-purinyl]-1,2-dlihydlro-2-pyridinone

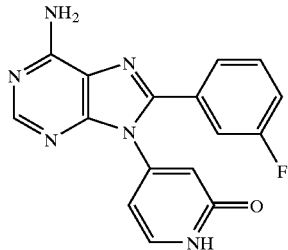

8-(3-Fluorophenyl)-9-{2–1 (4-methoxybenzyl)oxy]-4-pyridyl }-9H-6-purineamine (690 mg, 1.56 mmol) in Example 49 was dissolved in 3.5 ml trifluoroacetic acid and reacted at room temperature for 30 minutes. The reaction solution was diluted with water and the resulting precepitates were collected by filtration, washed with water and dried, to give the title compound (510 mg, 75%) as trifluoroacetate.

$^1$H NMR (400 MHz, CDCl$_3$) δ ppm; 6.15 (1H, d, J=5.1 Hz), 6.43 (1H, d, J=1.8 Hz), 7.32–7.54 (5H, m), 8.22 (1H, s).

Example 51

4-[6-Amino-8-(3-fluorophenyl)-9H-9-purinyl]-1-mothy-1,2 -dihydro-2-pyrinone

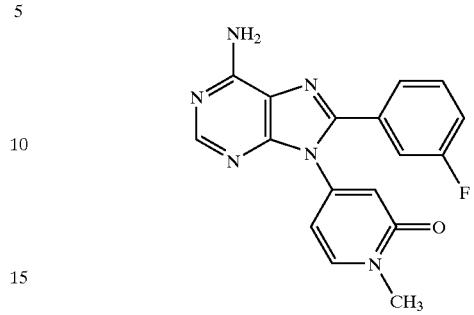

4-[6-Amino-8-(3-fluorophenyl)-9H-9-purinyl]-1,2-dihydro-2-pyridinone (50 mg, 0.16 mmol) in Example 50 was dissolved in 1 ml N,N-dimethylformamide, and 64 mg anhydrous potassium carbonate and 15 μl methyl iodide were added thereto and reacted at 60° C. for 2 hours. The reaction solution was cooled, then the insoluble matters were filtered off, and the filtrate was concentrated to dryness. The residue was purified by a silica gel column (eluted with ethyl acetate) and concentrated, to give the title compound (30 mg, 55%).

$^1$H NMR (400 MHz, CDCl$_3$) δ ppm; 3.53 (3H, s), 5.89 (2H, bs), 6.20 (1H, dd, J=2.2, 7.1 Hz), 6.46 (1H, d, J=2.3 Hz), 7.38 (1H, d, J=7.1 Hz), 8.32 (1H, s).

MS m/e (FAB) 337 (MH$^+$).

Example 52

8-(3-Fluorophenyl)-9-(4-pyritdyl)-9H-6-purineamine

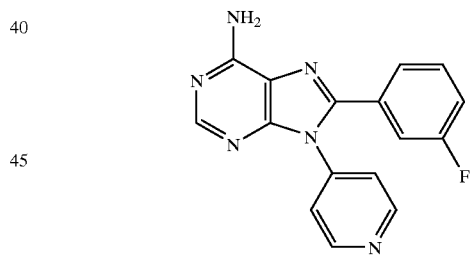

9-(2-Chloro-4-pyridyl)-8-(3-fluorophenyl)-9H-6-purineamine (50 'mg, 0.15 mmol) in Example 48 was dissolved in 5 ml methanol and 5 ml tetrahydrofuran, and 8.2 mg potassium hydroxide and 50 mg of 10% palladium carbon were added thereto. The mixture was stirred for 1 hour in a hydrogen atmosphere at room temperature. The reaction mixture was diluted with ethyl acetate, the catalyst was filtered off, and the filtrate was evaporated. The residue was suspended in water, and the resulting precipitates were collected by filtration, to give the title compound (35 mg, 77%)

$^1$H NMR (400 MHz, CDCl$_3$) b ppm; 5.82 (2H, br), 7.08–7.14 (2H, m) 7.22–7.32 (4H, m), 8.33 (1H, s), 8.71 (2H, d, J=6.0 Hz).

MS m/e (FAB) 306 (MH$^+$)

Example 53

5-[8-3 (Fluorophenyl)-9H-9-purinyl]-1-methyl-1,2-dihydro-2-pyridinoen

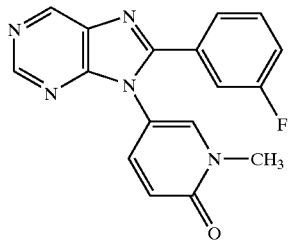

5-[6-Amino-8-(3-fluorophenyl)-9H-9-purinyl]-1-methyl-1,2-dihydro-2-pyridinone (1.0 g, 3.0 mmol) in Example 46 was dissolved in 20 ml tetrahydrofuran, and 1.2 ml isoamyl nitrite was added thereto and heated for 2 hour under reflux. The reaction solution was cooled and evaporated, and the residue was purified by a silica gel column. The desired product was eluted with ethyl acetate and then the solvent was removed, to give the title compound (340 mg, 35%)

$^1$H NMR (400 MHz, CDCl$_3$) ppm 3.62 (3H, s), 6.68 (1H, d, J=9.7), 7.21 (1H, dd, J=2.9, 9.7), 7.23–7.27 (1H, m), 7.41–7.49 (2H, m) 7.53–7.57 (1H, m)), 7.58 (1H, d, J=2.8), 9.00 (1H, s), 9.23 (1H, s)

MS m/e (ESI) 322 (MH$^+$)

Example 54

N-[9-(6-Chloro-3-pyridazinyl)-8-(3-fluorophenyl)-9H-purinyl]-N,N-dimethylamine

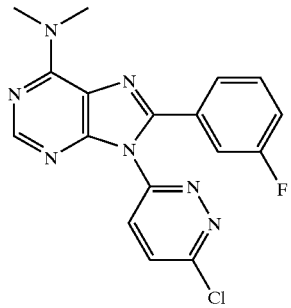

(1) 2-[(6-Chloro-5-nitro-4-prymidinyl)amino]ethyl cryanide

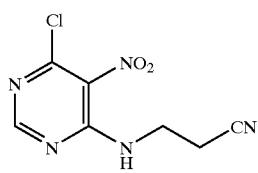

A mixture of 2-cyanoethylamine (15.9 g, 62.2 mmol), acetic acid (13 mL) and 30 ml methanol at 0° C. was added at room temperature to a suspension of 5-nitro-4,6-dichloropyrimidine (20.0 g, 0.10 mol) in tetrahydrofuran (400 mL), and the mixture was stirred at room temperature for 1 hour. The reaction solution was diluted with water and ethyl acetate (400 ml) and washed with 400 ml water and brine, and the organic layer was dried over anhydrous magnesium sulfate. The solvent was evaporated, then the residue was suspended in diethyl ether, and the resulting solid was collected by filtration and air-dried, to give the title compound (18.7 g, 79%).

$^1$H NMR (400 MHz, CDCl$_3$) δ ppm; 2.80 (2H, t, J=6.6 Hz), 3.94 (2H, q, J=6.6 Hz), 7.81 (1H, bs), 8.46 (1H, s)

(2) 2-[(5-Amino-6-Chloro-4-pyrimidinyl)amino]ethyl cyanide

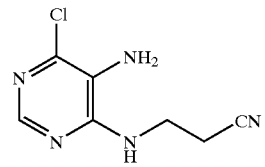

2-[(6-Chloro-5-nitro-4-pyrimidinyl)amino]ethyl cyanide (18.7 g, 82.2 mmol) was dissolved in 180 ml ethanol, 180 ml water and 18 ml acetic acid, and zinc powder was added slowly thereto at 0° C. The reaction solution was returned to room temperature and stirred for 30 minutes. Then, the insoluble matters were filtered off, and the filtrate was evaporated. The residue was diluted with ethyl acetate and washed with water and brine, and the organic layer was dried over anhydrous magnesium sulfate and concentrated. The residue was suspended in diethyl ether, and the precipitated solid was collected by filtration to give the title compound which was then washed with diethyl ether to give the title compound (44.6 g, 51%).

$^1$H NMR (400 MHz, CDCl$_3$) δ ppm; 2.80 (2H, t, J=6.2 Hz), 3.80 (2H, q, J=6.2 Hz), 5.30 (1H, bs), 8.10 (1H, s)

(3) N1-{4-Chloro-6-[(2-cyanoethyl)-5-pyrimidinyl}-3-fluorobenzamide

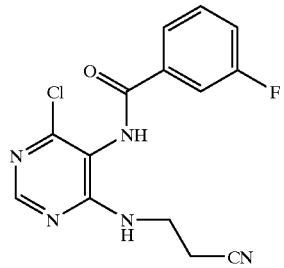

2-[(5-Amino-6-chloro-4-pyrimidinyl)amino]ethyl cyanide (10.0 g, 45.2 mmol) was dissolved in 63 ml pyridine, then 4.3 ml 3-fluorobenzoyl chloride was added thereto at 0° C., and the reaction solution was stirred at room temperature for 12 hours. The reaction solution was diluted with ethyl acetate and washed with water and brine, and the organic layer was dried over anhydrous magnesium sulfate. After the solvent was removed, the residue was suspended in diethyl ether, and the precipitated solid was collected by filtration and washed with diethyl ether, to give 8.9 g of the title compound (yield 87%).

$^1$H NMR (400 MHz, CDCl$_3$) δ ppm; 2.73 (2H, t, J=6.6 Hz), 3.80 (2H, q, J=6.4, Hz), 6.28 (1H, bs), 7.30–7.54 (1H, m), 7.47–7.53 (1H, m), 7.62–7.70 (2H, m), 7.80 (1H, d, bs), 8.37 (1H, s).

(4) 2-[6-Chloro-8-(3-fluoropthenyl)-9H-9-purinyl]ethyl cyanide

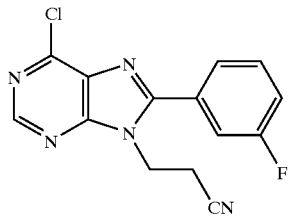

A suspension of N1-{4-chloro-6-[(2-cyanoethyl)amino]-5-pyrimidyl}-3-fluorobenzamide (8.9 g, 27.9 mmol) in phosphorus oxychloride (140 mL) was heated under reflux for 1.5 hours in a nitrogen atmosphere. After cooling as it was, the reaction solution was evaporated. The residue was diluted with ethyl acetate (100 ml), washed with water (×3), a saturated aqueous sodium bicarbonate solution (×2) and brine (×1), dried over anhydrous sodium sulfate and concentrated. The residue was suspended in diethyl ether, and the solid was collected by filtration and washed with diethyl ether, to give the title compound (4.1 g, 49%) as a colorless solid.

$^1$H NMR (400 MHz, CDCl$_3$) δ ppm; 3.04 (2H, t, J=6.8 Hz), 4.59 (2H, t, J=6.8 Hz), 7.26–7.32 (1H, m) 7.45–7.57 (3h, m), 8.72 (1H, s).

(5) 2-[-6-(Dimethylamino)-8-(3-fluoropheyl)-9H-9-purinyl]ethyl cyanide

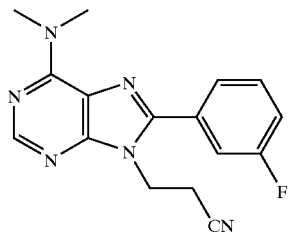

40% aqueous dimethylamine solution at 0° C. was added at room temperature to a solution of 2-[6-chloro-8-(3-fluorophenyl)-9H-9-purinyl]ethyl cyanide (1.5 g, 4.9 mmol) in tetrahydrofuran (30 mL) and stirred at room temperature for 1 hour. The reaction solution was diluted with water and ethyl acetate and washed with water and brine, and the organic layer was dried over anhydrous magnesium sulfate. After evaporation, the residue was suspended in diethyl ether, and the precipitated solid was collected by filtration and washed with ether, to give the title compound (740 mg, 48%).

$^1$H NMR (400 MHz, DMSO-d$_6$) δ ppm; 3.07 (2H, t, J=6.6 Hz), 3.32 (6H, s), 4.50 (2H, t, J=6.6 Hz), 7.40–7.46 (1H, m), 7.60-7.66 (3H, m), 8.28 (1H, s)

(6) N-[8-(3-Fluoropheny)-9H-6-puirinyl]-N,N-dimethylamine

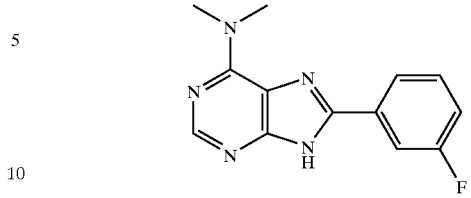

Sodium hydride, 14.1 mg (60% in mineral oil) at 0° C. was added to a solution of 2-[6-(dimethylamino)-8-(3-fluorophenyl)-9H-9-purinyl]ethyl cyanide (100 mg, 0.32 mmol) in N,N-dimethylformamide and stirred at room temperature for 1 hour. 5 ml saturated aqueous ammonium chloride solution was added to the reaction solution which was then diluted with ethyl acetate and washed with water and brine, and the organic layer was dried over anhydrous magnesium sulfate. The solvent was evaporated, and diethyl ether was added to the residue, and the precipitated solid was collected by filtration, to give the title compound (80 mg, 96%).

$^1$H NMR (400 MHz, DMSO-d$_6$) δ ppm; 3.30 (6H, s), 7.28–7.36 (1H, m) 7.54–7.60 (1H, m), 7.88–8.00 (2H, m), 8.20 (1H, s).

Then, N-[8-(3-fluorophenyl)-9H-6-purinyl]—N,N-dimethylamine (309 mg, 1.20 mmol) was dissolved in 15 ml N,N-dimethylformamide, and 2 g potassium carbonate and 1.1 g 3,6-dichloropyridazine were added thereto and stirred at 80° C. for 2 hours. The reaction solution was cooled and diluted with 100 ml ethyl acetate, and the insoluble matters were filtered off. The filtrate was concentrated to dryness, and the residue was purified by a silica gel column. The product was eluted with ethyl acetate and evaporated, to give the desired title compound (80 mg, 18%).

$^1$H NMR (400 MHz, CDCl$_3$) δ ppm 3.50 (3H, s), 4.11 (3H, s), 7.01–7.08 (1H, m), 7.36–7.42 (1H, m), 7.83 (1H, d, J=9.2 Hz), 8.00-8.04 (1H, m), B.08–8.12 (1H, m), 9.21 (1H, s), 9.36 (1H, d, J=9.3 Hz).

MS m/e (ESI) 370 (MH$^+$).

Example 55

N-[8-(3-Fluorophenyl)-9-(6-methoxy-3-pyridazinyl)-9H-6-purinyl]-N,N-dimethylamine

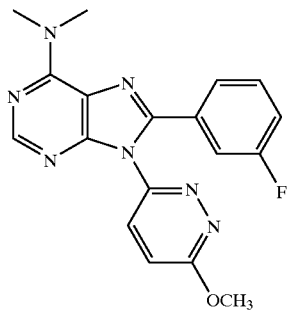

N-[9-(6–Chloro-3-pyridazinyl)-8-(3-fluorophenyl)-9H-6-purinyl ]-N,N-dimethylamine (50 mg, 0.18 mmol) in Example 54 was dissolved in 5 ml anhydrous methanol, and sodium methoxide (15 mg, 0.28 mmol) was added thereto and heated under reflux for 2 hours. The reaction solution was cooled, evaporated and suspended in water, and the precipitated solid were separated by filtration, to give the title compound (35 mg, 52%) as a colorless solid.

¹H NMR (400 MHz, CDCl₃) δ ppm 3.40 (3H, s), 4.04 (3H, s), 4.15 (3H, s), 6.92–6.98 (1H, m), 7.23 (1H, d, J=9.5 Hz), 7.28–7.34 (1H, m), 7.93–7.97 (1H, m), 8.0–8.06 (1H, m), 8.91 (1H, d, J=9.5 Hz), 8.93 (1H, s).

Example 56

5-[6-Amino-8-(3-fluorophenyl)-2-(3-hydroxy-3-methyl-1-butynyl)-9H-9-purinyl]-1-methyl-1,2-dihydro-2-pyridinone

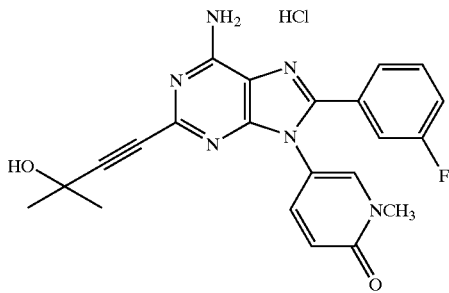

The compound obtained in Example 19 was treated in the same manner as in Example 21, to give the title compound.

¹H NMR (400 MHz, CDCl₃) δ ppm 1.63 (6H, s), 3.60 (3H, s), 6.20–6.40 (2H, br), 6.62 (2H, dd, J=1.6, 9.3 Hz), 7.10–7.20 (2H, m), 7.30–7.44 (3H, m), 7.57 (1H, bs).

MS m/e (FAB) 419 (MH⁺).

Example 57

5-{6-Amino-8-(3-fluorophenyl)-2-[2-(1-hydroxycyclobutyl)-1-ethynyl]-9H-9-purinyl}-1-methyl-1,2-dihydro-2-pyridinone hydrochloride

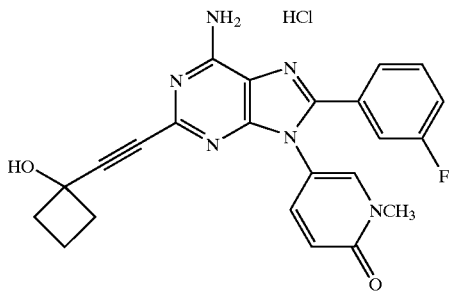

Using 5-{6-amino-8-(3-fluorophenyl)-2-[2-(1-hydroxycyclobutyl)-1-ethynyl]-9H-9-purinyl}-1,2-dihydro-2-pyridinone as a starting material, the title compound was obtained by treatment in the same manner as in Example 21.

¹H NMR (400 MHz, CDCl₃) δ ppm; 1.75–1.83 (2H, m), 2.21–2.30 (2H, m), 2.50–2.60 (2H, m), 3.54 (3H, s), 6.10 (2H, bs), 6.56 (2H, d, J=9.7 Hz), 7.07 (1H, dd, J=2.9, 9.7 Hz), 7.08–7.14 (1H, m), 7.26–7.38 (3H, m), 7.50 (1H, d, J=2.4 Hz).

MS m/e (FAB) 431 (MH+).

Example 58

9-(6-Methoxy-3-pyridyl)-8-(2-pyridyl)-9H-6-purineamine

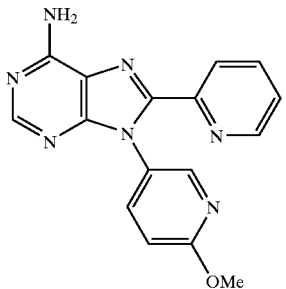

(1) N4-(6-Methoxy-3-pyridyl)-6-chloro-4,5-pyrimidine diamine

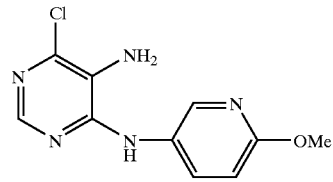

40 mL conc. aqueous hydrochloric acid was added dropwise to 40 g of 5-amino-4,6-dichloropyrimidine and 60.5 g of 5-amino-2-methoxypyridine in 800 ml mixture of ethanol and water (1/1) at room temperature. This mixture was stirred at 130° C. for 7 hours and 20 minutes, and 800 mL water was added to the reaction mixture at room temperature. The resulting suspension was filtered to give crude crystals, and then the crude crystals were subjected to re-crystallization from dimethylformamide and water, to give the title compound (32.7 g, 53% y) as greenish brown crystals.

(2) 5-(6-Chloro-9H-9-purinyl)-2-pyridyl methyl ether

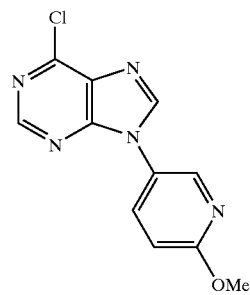

10.8 mL conc. aqueous hydrochloric acid was added dropwise to a suspension of 32.7 g of N4-(6-methoxy-3-pyridyl)-6-chloro-4,5-pyrimidine diamine in 400 mL dimethylformamide at room temperature, and this mixture was stirred at room temperature for 40 minutes and further stirred at 100° C. for 20 minutes. The reaction mixture was cooled as it was to room temperature, and the resulting suspension was filtered to give crude crystals which were then subjected to re-crystallization from dimethylformamide and water, to give 25 g of the title compound as gray crystals (74% y.).

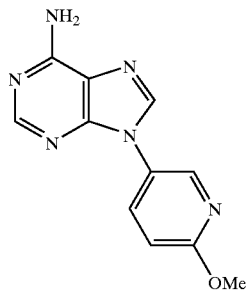

A mixture of 25 g of 5-(6-chloro-9H-9-purinyl)-2-pyridyl methyl ether, 250 mL conc. ammonia water and 500 mL dimethoxyethane was stirred at 70° C. for 4 hours, and the resulting suspension was filtered, to give 21.2 g of the title compound as white crystals (91% y.).

(4) 8-Bromo-9-(6-methoxy-3-pyridyl)-9H-6-purineamine

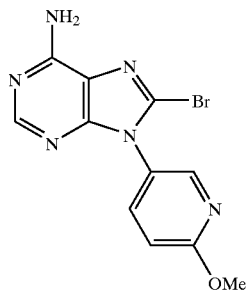

9.03 mL bromine was added dropwise to 21.2 g of 9-(6-methoxy-3-pyridyl)-9H-6-purineamine in a mixture (1.6 L) of dimethylformamide and water in a ratio of 1/1 at room temperature. This mixture was stirred at room temperature for 7 hours and 25 minutes, and the reaction mixture was filtered to give yellow crystals. A suspension of the resulting yellow crystals in a mixture (600 mL) of methanol and tetrahydrofuran in a ratio of 1/1 was stirred at room temperature overnight, and the suspension was filtered to give 12.3 g of the title compound as white crystals (44% y.).

Then, a solution of 500 mg of 8-bromo-9-(6-methoxy-3-pyridyl)-9H-6-prinamine, 1.15 g of tri-n-butyl (2-pyridyl) tin, 180 g of tetrakis(triphenylphosphine) palladium (0), and a solution of 814 µL N,N-diisopropylethylamine in xylene (15 mL) were stirred at 150° C. for 24 hours and 40 minutes. A small amount of methylene chloride and methanol was added to the reaction mixture, and this mixture was filtered through Celite. The filtrate was purified by short-column chromatography, to give 351 mg of the desired compound as brown crystals (71% y.).

Example 59

5-[6-Amino-8-(2-pyridyl)-9H-9-purinyl]-2-pyridinol

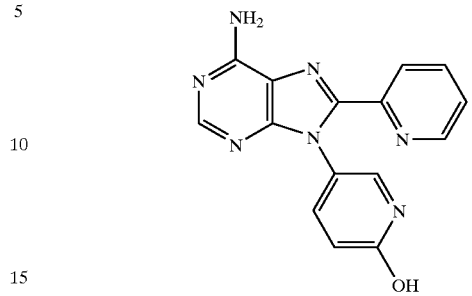

A mixture of 350 mg of 9-(6-methoxy-3-pyridyl)-8-(2-pyridyl)-9H-6-purineamine and 6 mL conc. aqueous hydrochloric acid was stirred at 105° C. for 1 hour and 45 minutes. From the resulting yellowish brown oily material, the solvent was evaporated, whereby yellowish brown crystals were obtained. The resulting crystals were collected by filtration with ethanol, to give 77 mg of the title compound as brown crystals (23% y.).

Example 60

5-[6-Amino-8-(2-pyridyl)-9H-9-purinyl]-1-methyl-1,2-dihydro-2-pyridinone

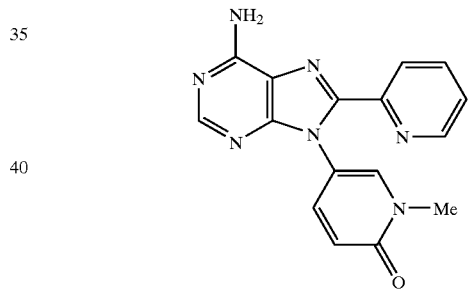

A solution of 150 mg of 5-[6-amino-8-(2-pyridyl)-9H-9-purinyl ]-2-pyridinol, 133 mg of sodium methoxide and 306 µL methyl iodide in 20 mL mixture of methanol and tetrahydrofuran in a ratio of 1/1 was stirred at room temperature for 2 hours and 35 minutes and then at 60° C. for 45 minutes. Ethyl acetate and water were added to the reaction mixture, and this mixture was extracted once with ethyl acetate. The organic layer was washed with brine, and the whole aqueous layer was extracted twice with ethyl acetate. The whole organic layer was dried over magnesium sulfate and filtered, and from the resulting residues, the solvent was evaporated, to give 90 mg of the title compound as brown crystals (58% y.).

$^1$H NMR (400 MHz, DMSO-d$_6$) δ ppm; 3.44 (1H, s), 6.43 (1H, d, J=9.2 Hz), 7.42–7.47 (2H, m), 7.53 (2H, brs), 7.96–8.02 (2H, m), 8.16-8.12 (2H, m), 8.49–8.50 (2H, m)

MS m/e (ESI) (MH$^+$).

Example 61

2-(3-Fluoropheyl)-3-(6-methoxy-3-pyridyl)-3H-imidazo]4,5-b]pyridine

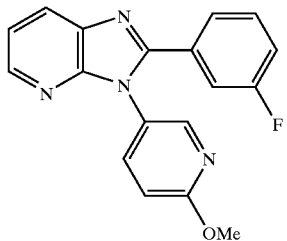

(1) N-(6-Methoxy-3-pyridyl)-N-(3-nitro-2-pyridyl)amine

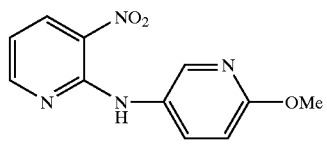

A solution of 15 g of 2-chloro-3-nitropyridine, 11.7 g of 5-amino-2-methoxypyridine and 26.1 g of potassium carbonate in 150 mL dimethylformamide was stirred at room temperature for 4 hours and 25 minutes and further stirred at 70° C. for 3 hours and 10 minutes. Ethyl acetate and water were added to the reaction mixture, and the mixture was extracted once with ethyl acetate. The organic layer was washed 3 times with a saturated aqueous ammonium chloride solution and once with brine, and dried over sodium sulfate. The residue was purified crudely by short-column chromatography. From and the resulting black brown oil was extracted with diethyl ether to give 9.10 g of the title compound as reddish brown crystals (39% y.).

(2) N2-(6-Methoxy-3-pyrdyl)-2,3-pyridinediamine

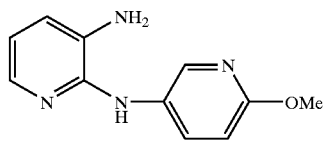

A solution of 9.10 g of N-(6-methoxy-3-pyridyl)-N-(3-nitro-2-pyridyl)amine and 1 g of 10% palladium carbon powder in a mixed solvent (200 mL) of methanol and ethyl acetate in a ratio of 1/1 was stirred at room temperature for 12 hours and 20 minutes in a hydrogen atmosphere. The reaction mixture was filtered through Celite, and the residue was purified by short-column chromatography to give crude crystals. The resulting crude crystals were collected by filtration, to give 4.52 g of the title compound as brown crystals (57% y.).

Then, a solution of 2.5 g of N2-(6-methoxy-3-pyridyl)-2,3-pyridine diamine, 1.24 mL 3-fluorobenzaldehyde and 3.3 mL acetic acid in 25 mL methanol was stirred at room temperature for 50 minutes. From the reaction mixture, the solvent was evaporated, and the residue was subjected 3 times to azeotropic distillation with toluene to give orange crystals. A suspension of 2.06 g of iron (III) chloride anhydride in 25 mL ethanol was added to the resulting crystals at room temperature and stirred at 95° C. for 1.5 hours. Ethyl acetate and a saturated aqueous ammonium chloride solution were added to the reaction mixture, and this mixture was filtered through Celite. The residues were extracted once with ethyl acetate, and the organic layer was washed twice with a saturated aqueous ammonium chloride solution and once with brine in this order. From the residues, the solvent was evaporated, and the resulting brown oil was purified by short-column chromatography, to give 1.80 g of the title compound as dark green crystals (48% y.).

Example 62

5-[2-(3-Fluoropheyl)-3H-imidazo[4,5-b]pyridin-3-yl]-2-pyridinol

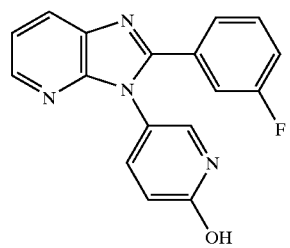

A mixture of 1.80 g of 2-(3-fluorophenyl)-3-(6-methoxy-3-pyridyl) -3H-imidazo[4,5-b]pyridine and 20 mL of 47% hydrobromic acid was stirred at 100° C. for 3 hours and 35 minutes. The reaction mixtures was evaporated, to give a brown oil. This oil was subjected 3 times to azeotropic distillation with toluene, and the resulting brown oil was subjected to crystallization from methanol, to give 1.07 g of the title compound as greenish brown crystals (63% y.).

Example 63

5-[2-(3-Fluorophenyl)-3H-imidazo[4,5-b]pyridin-3-yl]-1-methyl-1,2-dihydro-2-pyridinone

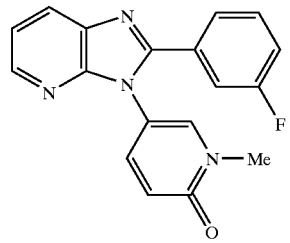

A solution of 250 mg of 5-[2-(3-fluorophenyl)-3H-imidazo [4,5-b]pyridin-3-yl]-2-pyridinol, 177 mg of sodium methoxide and 306 µL methyl iodide in a mixture (10 mL) of methanol and tetrahydrofuran in a ratio of 1/1 was stirred at room temperature for 1 day. Ethyl acetate and a saturated aqueous ammonium chloride solution were added thereto and the mixture was extracted 3 times with ethyl acetate. The organic layer was washed once with brine and dried over magnesium sulfate followed by distilling the solvent away under reduced pressure, to give crude crystals. The resulting crude crystals were collected by filtration with diethyl ether, to give 160 mg of the title compound as brown crystals (61% y.).

¹H NMR (400 MHz, DMSO-d₆) δ ppm; 3.46 (1H, s), 6.51 (2H, d, J=9.6 Hz), 7.38–7.44 (2H, m), 7.55–7.59 (4H, m), 8.18 (1H, s), 8.23 (1H, d, J=8.0 Hz), 8.39 (1H, d, J=4.8 Hz)

MS m/e (ESI) (MH⁺).

What is claimed is:

1. A compound, a pharmacologically acceptable salt thereof or hydrates thereof, which is represented by the formula (I):

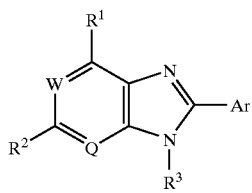

wherein R¹ represents 1) hydrogen, 2) hydroxyl, 3) a halogen atom, 4) an optionally substituted C1–C8 alkyl group or 5) formula —NR⁴R⁵, wherein R⁴ and R⁵ are the same as or different from each other and each represents hydrogen, a C1–C8 alkyl group, a C3–C8 cycloalkyl group, or a C2–C5 saturated cyclic amino group which is formed with the nitrogen to which they bind, whereupon this ring may contain oxygen, sulfur or nitrogen other than the nitrogen and may be substituted with a C1–C4 alkyl group which may be substituted with a halogen atom; R² represents 1) hydrogen, 2) a halogen atom, 3) formula —NR⁶R⁷, wherein R⁶ and R⁷ are the same as or different from each other and each represents hydrogen, a C2–C5 acyl group, a C1–C8 alkyl group or a C3–C8 cycloalkyl group, or R⁶ and R⁷ represent a C2–C5 saturated cyclic amino group which is formed with the nitrogen to which they bind, whereupon this ring may contain oxygen, sulfur or nitrogen other than said nitrogen and may be substituted with a C1–C4 alkyl group which may be substituted with a halogen atom), 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group, 6) a C1–C8 alkyl group which may be substituted with a halogen atom, hydroxyl or a C1–C4 alkyl group or 7) a C1–C8 alkoxy group which may be substituted with a halogen atom, hydroxyl or a C1–C4 alkyl group; R³ represents 1) a C3–C8 alkynyl group which may be substituted with a halogen atom, hydroxyl or a C1–C4 alkyl group, 2) a C3–C8 alkenyl group which may be substituted with a halogen atom, hydroxyl or a C1–C4 alkyl group, 3) an optionally substituted heteroaryl group wherein the heteroaryl group is selected from the group consisting of a pyrrole group, a pyrazolyl group, an imidazolyl group, a triazolyl group, a tetrazolyl group, a thiazolyl group, a pyridyl group, a pyrimidyl group and a pyrazinyl group, 4) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 5) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group or 6) a dihydroxo- or tetrahydrodioxopyrazinyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group; Ar represents 1) an optionally substituted aryl group, 2) an optionally substituted heteroaryl group, wherein the heteroaryl group is selected from the group consisting of a pyrrole group, a pyrazolyl group, an imidazolyl group, a triazolyl group, a tetrazolyl group, a thiazolyl group, a pyridyl group, a pyrimidyl group and a pyrazinyl group, 3) an oxopyridyl group which may be substituted with a halogen atom or a C1–C6 alkyl group, and whose nitrogen atom is further substituted with a C1–C6 alkyl group or a C3–C6 cycloalkyl group or 4) an oxopyrimidyl group which may be substituted with a halogen atom or a C1–C6 alkyl group, and whose nitrogen atom is further substituted with a C1–C6 alkyl group or a C3–C6 cycloalkyl group; and Q and W represent N.

2. The compound according to claim 1, a pharmacologically acceptable salt thereof or hydrates thereof, wherein R² is a hydrogen atom.

3. The compound according to claim 1 or 2, a pharmacologically acceptable salt thereof or hydrates thereof, wherein R³ represents 1) an optionally substituted heteroaryl group, 2) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 3) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl, or an optionally protected carboxyl group, b-2) an optionally substituted C3–C6 cycloalkyl-C1–C4 alkyl group or b-3) a C3–C6 cycloalkyl group, or 4) a dihydroxo or tetrahydrodioxopyrazinyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group, or b-3) a C3–C6 cycloalkyl group.

4. The compound according to claim 1, a pharmacologically acceptable salt thereof or hydrates thereof, wherein R³ represents 1) an optionally substituted pyridyl group, 2) an optionally substituted pyrimidyl group, 3) a 1,2-dihydro-2-oxopyridyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group; b-2) an optionally substituted C3–C6 cycloalkyl-C1–C4 alkyl group; or b-3) an optionally substituted C3–C6 cycloalkyl group, or 4) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group; b-2) an optionally substituted C3–C6 cycloalkyl-C1–C4 alkyl group; or b-3) a C3–C6 cycloalkyl group.

5. The compound according to claim 1, a pharmacologically acceptable salt thereof or hydrates thereof, wherein Ar is an optionally substituted aryl.

6. The compound according to claim 1, a pharmacologically acceptable salt thereof or hydrates thereof, wherein Ar is a phenyl substituted with a halogen atom.

7. The compound according to claim 1, a pharmacologically acceptable salt thereof or hydrates thereof, wherein $R^1$ is represented by the formula —$NR^4R^5$, wherein $R^4$ and $R^5$ are the same as or different from each other and each represents hydrogen, a C1–C8 alkyl group or a C3–C8 cycloalkyl group, or a C2–C5 saturated cyclic amino group which is formed with a nitrogen atom to which they bind, whereupon this ring may contain oxygen, sulfur or nitrogen other than the nitrogen and may be substituted with a C1–C4 alkyl group which may be substituted with a halogen atom.

8. The compound according to claim 1, a pharmacologically acceptable salt thereof or hydrates thereof, wherein $R^1$ is amino.

9. The compound according to claim 1, a pharmacologically acceptable salt thereof or hydrates thereof, wherein $R^1$ is amino; $R^2$ is hydrogen; and $R^3$ is 1) a pyridyl group which may be substituted with hydroxyl or a C1–C6 alkyl group or 2) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group; b-2) an optionally substituted C3–C6 cycloalkyl-C1–C4 alkyl group; or b-3) an optionally substituted C3–C6 cycloalkyl group.

10. The compound according to claim 1, a pharmacologically acceptable salt thereof or hydrates thereof, wherein $R^1$ is amino, $R^2$ is hydrogen, and $R^3$ is a 1,2-dihydro-2-oxopyridyl group whose nitrogen may be substituted with a C1 to C6 alkyl group which may be substituted with a halogen atom.

11. The compound according to claim 1, a pharmacologically acceptable salt thereof or hydrates thereof, wherein R. is amino, $R^2$ is a C2 alkynyl group which is substituted with a hydroxy-C4–C6 cycloalkyl group, $R^3$ is a C3 alkenyl group, and Ar is a phenyl substituted with a halogen atom.

12. The compound according to claim 1, which is selected from the following group:
1) 5-[6-amino-8-(3-fluorophenyl)-9H-9-purinyl]-1-methyl-1,2-dihydro-2-pyridiwnone, and
2) 1-(2-[6-amino-8-(3-fluoropiienyl)-9-(2-propenyl)-9H-2-purinyl ]-1ethynyl}-1-cyclobutanol,
a pharmacologically acceptable salt thereof or hydrates thereof.

13. A process for producing an acylaminopyridine compound-represented by the following formula:

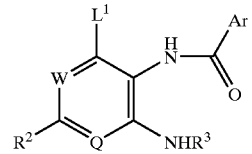

(A3)

(wherein $L^1$, $R^2$, $R^3$, Ar, Q and W have the same meanings as defined below, respectively), a salt thereof or hydrates thereof, which comprises allowing an aminopyrimidine compound (A2) represented by the following formula:

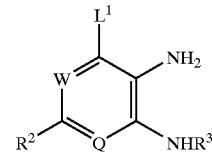

(A2)

(wherein $L^1$ represents a halogen atom; $R^2$ represents 1) hydrogen, 2) a halogen atom, 3) formula —$NR^6R^7$ (wherein $R^6$ and $R^7$ are the same as or different from each other and represent hydrogen, a C2–C5 acyl group, a C1–C8 alkyl group or a C3–C8 cycloalkyl group, or $R^6$ and $R^7$ represent a C2–C5 saturated cyclic amino group which is formed with a nitrogen atom to which they bind, whereupon this ring may contain an oxygen atom, a sulfur atom or a nitrogen atom other than the nitrogen atom and may be substituted with a C1–C4 alkyl group which may be substituted with a halogen atom), 4) a C2–C8 alkynyl group which may be substituted with a halogen atom, hydroxyl, a C1–C4 alkyl group or a C3–C6 cycloalkyl group, 5) a C3–C8 alkenyl group which may be substituted with a halogen atom, hydroxyl or a C1–C4 alkyl group, 6) a C1–C8 alkyl group which may be substituted with a halogen atom, hydroxyl or a C1–C4 alkyl group, or 7) a C1–C8 alkoxy group which may be substituted with a halogen atom, hydroxyl or a C1–C4 alkyl group; $R^3$ represents 1) a C3–C8 alkynyl group which may be substituted with a halogen atom, a hydroxyl group or a C1–C4 alkyl group, 2) a C3–C8 alkenyl group which may be substituted with a halogen atom, a hydroxyl group or a C1–C4 alkyl group, 3) a C1–C8 alkyl group which may be substituted with a halogen atom, a hydroxyl group or a C1–C4 alkyl group, 4) an optionally substituted aryl group, 5) an optionally substituted heteroaryl group, wherein the heteroaryl group is selected from the group consisting of a pyrrole group, a pyrazolyl group, an imidazolyl group, a triazolyl group, a tetrazolyl group, a thiazolyl group, a pyridyl group, a pyrimidyl group and a pyrazinyl group, 6) a 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 7) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group or 8) a dihydroxo or tetrahydrodioxopyrazinyl group which may be substituted with a) a halogen atom or a C1–C6 alkyl group and whose nitrogen atom is further substituted with b-1) a C1–C6 alkyl group which may be substituted with a halogen atom, hydroxyl or an optionally protected carboxy, b-2) an optionally substituted C3–C6 cycloalkyl-C1–C4 alkyl group, or b-3) a C3–C6 cycloalkyl group; and Q and W represent N, to react with an acyl compound represented by the formula ArCOX (wherein X represents a halogen atom; and Ar represents 1) an optionally substituted aryl group, 2) an optionally substituted heteroaryl group, wherein the heteroaryl group is selected from the group consisting of a pyrrole group, a pyrazolyl group, an imidazolyl group, a triazolyl group, a tetrazolyl group, a thiazolyl group, a pyridyl group, a pyrimidyl group and a pyrazinyl group, 3) an oxopyridyl group which may be substituted with a halogen atom or a C1–C6 alkyl group and whose nitrogen atom is substituted with a C1–C6 alkyl group or a C3–C6 cycloalkyl group, or 4) an oxopyrimidyl group which may be substituted with a halogen atom or a C1–C6 alkyl group and whose nitrogen atom is substituted with a C1–C6 alkyl group or a C3–C6 cycloalkyl group).

14. The process for producing an acylaminopyrimidine compound (A3), a salt thereof or hydrates thereof according to claim 13, wherein $R^3$ is an N-C1–C8 alkyl-2-oxopyrimidinyl group.

15. A process for producing an imidazopyrimidine compound (C3), a salt thereof or hydrates thereof represented by the formula:

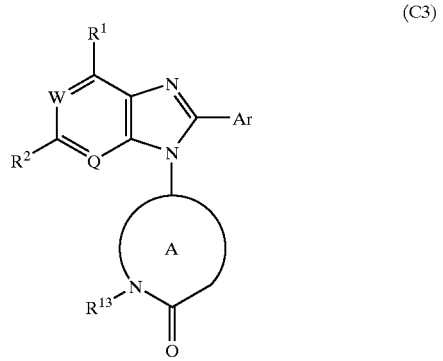

(C3)

wherein $R^{13}$ means a C1–C6 alkyl group which may be substituted with a halogen atom, hydroxyl or an optionally protected carboxyl group, an optionally substituted C3–C6 cycloalkyl-C1–C4 alkyl group, or an optionally substituted C3–C6 cycloalkyl group; and $R^1$, the formula:

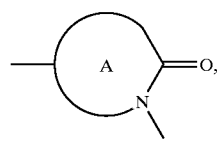

on formula C3, represents 1,2-dihydro-2-oxopyridyl group which may be substituted with a) a halogen atom or a C1–C6 alkyl group, and whose nitrogen atom may further be substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) an optionally substituted C3–C6 cycloalkyl group, 5) a dihydroxopyrimidyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group or 6) a dihydroxo- or tetrahydrodioxopyrazinyl group which may be substituted with a) a halogen atom or a C1–C6 alkyl group, and whose nitrogen atom is further substituted with b-1) a C1–C6 alkyl group which may be substituted with a halogen atom, hydroxyl or an optionally protected carboxyl group, b-2) an optionally substituted C3–C6 cycloalkyl-C1–C4 alkyl group or b-3) a C3–C6 cycloalkyl group;

$R^2$, Ar, Q and W have the same meanings as defined above, respectively, which comprises alkylating an imidazopyrimidine compound (C2) represented by the following formula:

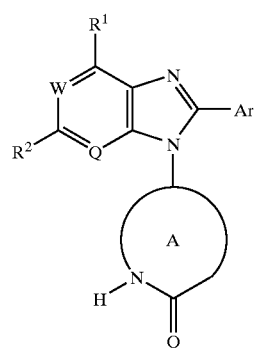

(C2)

wherein $R^1$ represents 1) hydrogen, 2) hydroxyl, 3) a halogen atom, 4) an optionally substituted C1–C8 alkyl group or 5) formula —$NR^4R^5$, wherein $R^4$ and $R^5$ are the same as or different from each other and each represents hydrogen, a C1–C8 alkyl group or a C3–C8 cycloalkyl group, or a C2–C5 saturated cyclic amino group which is formed with a nitrogen atom to which they bind, whereupon this ring may contain oxygen, sulfur or nitrogen other than the nitrogen atom and may be substituted with a C1–C4 alkyl group which may be substituted with a halogen atom; the formula:

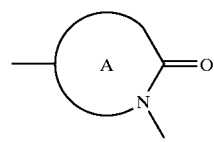

on formula (C2), is as defined above but the nitrogen is substituted by hydrogen; and $R^2$, Ar, Q and W have the same meanings as defined above, respectively.

16. A method of treating diabetes mellitus, which comprises administering an effective amount of the compound according to claim 1, a pharmacologically acceptable salt thereof or hydrates thereof to an individual in need thereof for treating diabetes mellitus.

17. A method of treating diabetic complications, which comprises administering an effective amount of the compound according to claim 1, a pharmacologically acceptable salt thereof or hydrates thereof to an individual in need thereof for treating diabetic complications.

18. A method of treating diseases against which the compound according to claim 1, a pharmacologically acceptable salt thereof or hydrates thereof is effective.

19. A method of treating diabetic retinopathy, which comprises administering an effective amount of the compound according to claim 1 to a patient in need thereof for treating diabetic retinopathy.

20. An adenosine A2 receptor antagonist comprising the compound according to claim 1, a pharmacologically acceptable salt thereof or hydrates thereof.

21. A pharmaceutical composition comprising the compound according to claim 1, a pharmacologically acceptable salt thereof or hydrates thereof and a pharmacologically acceptable carrier.

22. A method of treating diabetes mellitus; diabetic complications; diabetic retinopathy; diseases against which the compound according to claim 1, a pharmacologically acceptable salt thereof or hydrates thereof is effective; or diseases against which an adenosine A2 receptor antagonism is effective, by administering a pharmacologically effective amount of the compound according to claim 1, a pharmacologically acceptable salt thereof or hydrates thereof.

23. The method of claim 16 wherein an effective amount of compound is 0.03 to 1000 mg per day.

24. The method of claim 17 wherein an effective amount of compound is 0.03 to 1000 mg per day.

25. The method of claim 19 wherein an effective amount of compound is 0.03 to 1000 mg per day.

26. The method of claim 16 wherein an effective amount of compound is 0.1 to 500 mg per day.

27. The method of claim 17 wherein an effective amount of compound is 0.1 to 500 mg per day.

28. The method of claim 19 wherein an effective amount of compound is 0.1 to 500 mg per day.

29. The method of claim 16 wherein an effective amount of compound is 0.1 to 100 mg per day.

30. The method of claim 17 wherein an effective amount of compound is 0.1 to 500 mg per day.

31. The method of claim 19 wherein an effective amount of compound is 0.1 to 500 mg per day.

32. The method of claim 16 wherein an effective amount of compound is administered by injection and the injection amount is 1 $\mu$g/Kg.

33. The method of claim 17 wherein an effective amount of compound is administered by injection and the injection amount is 1 $\mu$/Kg.

34. The method of claim 19 wherein an effective amount of compound is administered by injection and the injection amount is 1 $\mu$g/Kg.

* * * * *